(12) United States Patent
Astles et al.

(10) Patent No.: US 6,479,519 B1
(45) Date of Patent: Nov. 12, 2002

(54) SUBSTITUTED ANILIDES

(75) Inventors: Peter Charles Astles, Dagenham (GB); David Edward Clark, Dagenham (GB); Alan John Collis, Dagenham (GB); Paul Joseph Cox, Dagenham (GB); Paul Robert Eastwood, Dagenham (GB); Neil Victor Harris, Dagenham (GB); Justine Yeun Quai Lai, Dagenham (GB); Andrew David Morley, Dagenham (GB); Barry Porter, Dagenham (GB)

(73) Assignee: Aventis Pharma Limited, West Malling Kent (GB)

( * ) Notice: Subject to any disclaimer, the term of this patent is extended or adjusted under 35 U.S.C. 154(b) by 0 days.

(21) Appl. No.: 09/558,812

(22) Filed: Apr. 26, 2000

Related U.S. Application Data

(63) Continuation of application No. PCT/GB98/03294, filed on Nov. 2, 1998
(60) Provisional application No. 60/069,695, filed on Dec. 16, 1997, and provisional application No. 60/104,287, filed on Oct. 14, 1998.

(51) Int. Cl.[7] ............ C07C 275/38; C07C 275/40; C07D 213/75; A61K 31/17; A61P 19/02
(52) U.S. Cl. ............ 514/332; 514/352; 514/598; 526/346; 544/332; 544/336; 546/265; 546/309; 568/49; 568/50; 568/51; 568/52; 568/53; 568/54; 568/55
(58) Field of Search ................ 514/183, 241, 514/247, 255.06, 256, 275, 332, 352, 598; 526/346; 544/179, 210, 224, 322, 329, 332, 336; 546/265, 309; 568/49, 50, 51, 52, 53, 54, 55

(56) References Cited

U.S. PATENT DOCUMENTS

| | | | |
|---|---|---|---|
| 5,780,483 A | 7/1998 | Widdowson et al. | 514/311 |
| 6,352,977 B1 * | 3/2002 | Astles et al. | 514/18 |

FOREIGN PATENT DOCUMENTS

| | | |
|---|---|---|
| WO | WO 95/20578 | 8/1993 |
| WO | WO 94/22807 | 10/1994 |
| WO | WO 96/22966 | 8/1996 |
| WO | WO 97/36859 | 10/1997 |
| WO | WO 97/36862 | 10/1997 |
| WO | WO 97/40028 | 10/1997 |
| WO | WO 97/49399 | 12/1997 |
| WO | WO 97/49400 | 12/1997 |
| WO | WO 98/04247 | 2/1998 |

* cited by examiner

*Primary Examiner*—Mukund J. Shah
*Assistant Examiner*—Thomas McKenzie
(74) *Attorney, Agent, or Firm*—Ronald G. Ort

(57) ABSTRACT

The invention is directed to physiologically active compounds of formula (I):

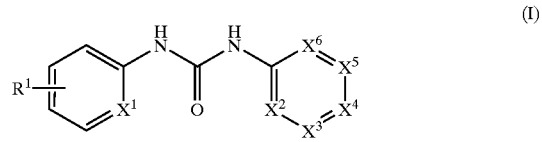

wherein:

$R^1$ is hydrogen, halogen, hydroxy, lower alkyl or lower alkoxy;

$X^1$, $X^2$ and $X^6$ independently represent N or $CR^{10}$; and one of $X^3$, $X^4$ and $X^5$ represents $CR^{11}$ and the others independently represents N or $CR^{10}$;

where $R^{10}$ is hydrogen, amino, halogen, hydroxy, lower alkyl, lower alkoxy, lower alkylthio, lower alkylsulphinyl, lower alkylsulphonyl, nitro or trifluoromethyl; and $R^{11}$ represents a group —$L^1$—$Ar^1$—$L^2$—Y; and the corresponding N-oxides, and their prodrugs; and pharmaceutically acceptable salts and solvates of such compounds and their N-oxides and prodrugs. Such compounds have valuable pharmaceutical properties, in particular the ability to regulate the interaction of VCAM-1 and fibronectin with the integrin VLA-4 ($\alpha4\beta1$).

81 Claims, No Drawings

SUBSTITUTED ANILIDES

This application is a continuation of PCT/GB98/03294, filed Nov. 2, 1998, which claims priority from GB Application No. 9723072.6, filed Oct. 31, 1997, GB Application No. 9814276.3, filed Jul. 1, 1988, U.S. Application No. 60/069,695, filed Dec. 16, 1997, and U.S. Application No. 60/104,287, filed Oct. 14, 1998.

This invention is directed to substituted anilides, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g. fibronectin, vitronectin and VCAM-1) and their integrin receptors [e.g. VLA-4 ($\alpha_4\beta_1$)]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called $\alpha$ and $\beta$. There are at least twelve different $\alpha$-subunits ($\alpha 1$–$\alpha 6$, $\alpha$-L, $\alpha$-M, $\alpha$-X, $\alpha$-IIb, $\alpha$-V and $\alpha$-E) and at least nine different $\beta$ ($\beta 1$–$\beta 9$) subunits. The integrin family can be subdivided into classes based on the $\beta$ subunits, which can be associated with one or more $\alpha$-subunits. The most widely distributed integrins belong to the $\beta 1$ class, also known as the very late antigens (VLA). The second class of integrins are leukocyte specific receptors and consist of one of three $\alpha$-subunits ($\alpha$-L, $\alpha$-M or $\alpha$-X) complexed with the $\beta 2$ protein. The cytoadhesins $\alpha$-IIb$\beta 3$ and $\alpha$-V$\beta 3$, constitute the third class of integrins.

The present invention principally relates to agents which modulate the interaction of the ligand VCAM-1 with its integrin receptor $\alpha 4\beta 1$ (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin $\alpha 4\beta 1$ mediates both cell-cell and cell-matrix interactions. Cells expressing $\alpha 4\beta 1$ bind to the carboxy-terminal cell binding domain of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-$\gamma$, TNF-$\alpha$ and LI-1$\beta$.

Regulation of $\alpha 4\beta 1$ mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which $\alpha 4\beta 1$ binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J.Clin.lnvest., 1994, 94, pages 655–662). In the oxazalone-sensitised model of inflammation (contact hypersensitivity response) in mice, intravenous administration of anti-$\alpha 4$ specific monoclonal antibodies significantly inhibited (50–60% reduction in the ear swelling response) the efferent response (P. L. Chisholm et al. J.lmmunol., 1993, 23, pages 682–688).

We have now found a novel group of substituted anilides which have valuable pharmaceutical properties, in particular the ability to regulate the interaction of VCAM-1 and fibronectin with the integrin VLA-4 ($\alpha 4\beta 1$).

Thus, in one aspect, the present invention is directed to compounds of general formula (I):

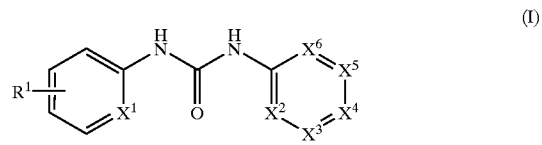

wherein:

$R^1$ is hydrogen, halogen, hydroxy, lower alkyl or lower alkoxy;

$X^1$, $X^2$ and $X^6$ independently represent N or $CR^{10}$; and one of $X^3$, $X^4$ and $X^5$ represents $CR^{11}$ and the others independently represents N or $CR^{10}$ [where $R^{10}$ is hydrogen, amino, halogen, hydroxy, lower alkyl, lower alkoxy, lower alkylthio, lower alkylsulphinyl, lower alkylsulphonyl, nitro or trifluoromethyl; and $R^{11}$ represents a group —$L^1$—$Ar^1$—$L^2$—Y in which:

$L^1$ represents a —$R^2$—$R^3$— linkage, where $R^2$ is a straight or branched $C_{1-6}$alkylene chain, a straight or branched $C_{2-6}$alkenylene chain or a straight or branched $C_{2-6}$alkynylene chain, and $R^3$ is a direct bond, cycloalkylene, heterocycloalkylene, arylene, heteroaryldiyl, —C(=Z)—$NR^4$—, —$NR^4$—C(=Z)—, —$Z^1$—, —C(=O)—, —C(=$NOR^4$)—, —$NR^4$—C(=Z)—$NR^4$—, —$SO_2$—$NR^4$—, —$NR^4$—$SO_2$—, —O—C(=O)—, —C(=O)—O—, —$NR^4$—C(=O)—O— or —O—C(=O)—$NR^4$— (where $R^4$ is a hydrogen atom or a lower alkyl group; Z is O or S; $Z^1$ is O, $S(O)_n$ or $NR^4$ and n is zero or an integer 1 or 2); but excluding compounds where an oxygen, nitrogen or sulphur atom in $R^3$ is attached directly to a carbon carbon multiple bond in $R^2$;

$Ar^1$ is arylene or heteroaryldiyl;

$L^2$ represents:

(i) a direct bond;
(ii) an alkylene, alkenylene, alkynylene, cycloalkenylene, cycloalkylene, heteroaryldiyl, heterocycloalkylene or arylene linkage each optionally substituted by (a) an acidic functional group (or corresponding protected derivative), $R^5$, —ZH, —$ZR^5$, —C(=O)—$R^5$, —N($R^{12}$)—C(=O)—$R^{13}$, —N($R^{12}$)—C(=O)—O$R^{13}$, —N($R^{12}$)—$SO_2$—$R^{13}$, —N$Y^1Y^2$, or —[C(=O)—N($R^6$)—C($R^4$)($R^7$)]$_p$—C(=O)—N$Y^1Y^2$, or by (b) alkyl substituted by an acidic functional group (or corresponding protected derivative), or by —ZH, —$ZR^5$, —C(=O)—N$Y^1Y^2$ or —N$Y^1Y^2$;
(iii) a —[C(=O)—N($R^6$)—C($R^4$)($R^7$)]$_p$— linkage;
(iv) a —$Z^2$—$R^9$— linkage;
(v) a —C(=O)—$CH_2$—C(=O)— linkage;
(vi) a —$R^9$—$Z^2$—$R^9$— linkage; or
(vii) a —C($R^4$)($R^8$)—[C(=O)—N($R^6$)—C($R^4$)($R^7$)]$_p$— linkage;
{in which
$R^5$ is alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl, or heterocycloalkylalkyl;
$R^6$ is hydrogen, $R^5$ or alkyl substituted with alkoxy, cycloalkyl, hydroxy, mercapto, alkylthio or —N$Y^1Y^2$;
$R^7$ and $R^8$ are each independently selected from hydrogen or a group consisting amino acid side chains and corresponding protected derivatives, an acidic functional group (or corresponding protected derivative), $R^5$, —$ZR^5$, —C(=O)—$R^5$, or —C(=O)—N$Y^1Y^2$, or alkyl substituted by an acidic functional group (or corresponding protected derivative)or by $R^5$, —$ZR^5$, —N$Y^1Y^2$, —NH—C(=O)—$R^5$, —C(=O)—$R^2$—$NH_2$, —C(=O)—$Ar^1$—$NH_2$, —C(=O)—$R^2$—$CO_2H$, or —C(=O)—N$Y^1Y^2$;
or $R^6$ and $R^7$ or $R^6$ and $R^8$ together with the atoms to which they attached form a 3- to 6-membered heterocycloalkyl ring;
$R^9$ is $C_{1-6}$alkylene, optionally substituted by $R^5$;
$R^{12}$ is hydrogen, alkyl, aryl, arylalkyl, cycloalkyl, cycloalkylalkyl, heteroaryl, heteroarylalkyl, heterocycloalkyl or heterocycloalkylalkyl;
$R^{13}$ is alkyl, aryl, cycloalkyl, heteroaryl or heterocycloalkyl, or alkyl substituted by aryl, an acidic functional group (or corresponding protected derivative), cycloalkyl, heteroaryl, heterocycloalkyl, —ZH, —$ZR^5$, —C(=O)—N$Y^1Y^2$ or —N$Y^1Y^2$;
$Y^1$ and $Y^2$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —N$Y^1Y^2$, or one or more —$CO_2R^{12}$ or —C(=O)—N$Y^1Y^2$ groups; or the group —N$Y^1Y^2$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), $R^{13}$; (ii) may also contain a further heteroatom selected from O, S, $SO_2$, or $NY^3$ [where $Y^3$ is hydrogen, alkyl, aryl, arylalkyl, —C(=O)—$R^{14}$, —C(=O)—O$R^{14}$ or —$SO_2R^{14}$ (in which $R^{14}$ is alkyl, aryl, arylalkyl, cycloalkyl, cycloalkylalkyl, heteroaryl, heteroarylalkyl, heterocycloalkyl or heterocycloalkylalkyl)]; and (iii) may also be fused to additional aryl, heteroaryl, heterocycloalkyl or cycloalkyl rings to form a bicyclic or tricyclic ring system;
$Z^2$ is O S(O)$_n$, $NR^4$, $SONR^4$, C(=O)$NR^4$ or C(=O); and
p is zero or an integer 1 to 4}; and
Y is carboxy (or an acid bioisostere) or —C(=O)—N$Y^1Y^2$];
and the corresponding N-oxides, and their prodrugs; and pharmaceutically acceptable salts and solvates (e.g. hydrates) of such compounds and their N-oxides and prodrugs; excluding the compounds (2-{2-[4-(3-(2-methylphenyl)ureido)-phenyl]-acetylamino}-thiazol-4-yl)-acetic acid, 2-phenylacetylamino-3-{4-[4-(3-(2-methylphenyl)ureido)-benzyloxy]-phenyl}-propionic acid, 2-phenylacetylamino-3-(4{2-[4-(3-(2-methylphenyl)ureido)-phenyl]-ethoxy}-phenyl)-propionic acid, 2-benzylsulphonylamino-3-{4-[4-(3-(2-methylphenyl)ureido)-benzyloxy]-phenyl}-propionic acid, (butane-1-sulphonylamino)-{2-[4-(3-(2-methylphenyl)-ureido)-benzyl]-benzofuran-6-yl}-acetic acid, 3-(benzylaminocarbonyl)-(4{2-[4-(3-(2-methylphenyl) ureido)-phenyl]-ethoxy}-benzyl)-propionic acid and 2-benzyloxycarbonylamino-3-(5-{3-[4-(3-(2-methylphenyl) ureido)-phenyl]-propyl}-thiophene-2-yl)-propionic acid; and with the proviso that $L^1$ cannot represent $C_{1-6}$alkylene-C(=O)—NH— or $C_{1-6}$alkylene when $Ar^1$ represents optionally substituted phenylene, Y represents —$CO_2H$, —$SO_3H$, —$PO_4H_2$ or tetrazole, and $L^2$ represents (i) a direct bond, (ii) an alkylene or alkenylene linkage each optionally substituted by (a) alkyl, alkenyl, alkynyl, cycloalkyl, cycloalkenyl, aryl, arylalkyl, heteroaryl, heteroarylalkyl or heterocycloalkyl, or by (b) alkyl substituted by alkoxy, hydroxy, arylalkyoxy, heteroarylalkyloxy, alkylthio, carboxy, alkoxycarbonyl, or —C(=O)—$NH_2$, (iii) a —[C(=O)—N($R^6$)—C($R^4$)($R^7$)]$_p$— linkage in which $R^4$ is hydrogen or lower alkyl, $R^6$ is hydrogen, alkyl, alkenyl, alkynyl, cycloalkyl, cycloalkylalkyl, cycloalkenyl, cycloalkenylalkyl, aryl, arylalkyl, heteroaryl, heteroarylalkyl, heterocycloalkyl, heterocycloalkylalkyl or alkyl substituted by alkoxy, hydroxy or alkylthio, $R^7$ is hydrogen, alkyl, alkenyl, alkynyl, cycloalkyl, cycloalkylalkyl, cycloalkenyl, cycloalkenylalkyl, aryl, arylalkyl, heteroaryl, heteroarylalkyl, heterocycloalkyl, heterocycloalkylalkyl or alkyl substituted by alkenyl, alkynyl, alkoxy, hydroxy, arylalkyloxy, heteroarylalkyloxy, alkylthio, carboxy, alkoxycarbonyl or carboxamide, and p is one, (iv) a —$Z^2$—$R^9$— linkage in which $Z^2$ is O, S, $NR^4$, $SO_2NR^4$ or C(=O)$NR^4$ and $R^9$ is $C_{1-4}$alkylene, optionally substituted by alkyl, alkenyl, alkynyl, cycloalkyl, cycloalkylalkyl, cycloalkenyl, cycloalkenylalkyl, aryl, arylalkyl, heteroaryl, heteroarylalkyl or heterocycloalkyl, or (v) a —$CH_2$—$Z^2$—$R^9$— linkage in which $Z^2$ is O, $NR^4$ or C(=O)$NR^4$ and $R^9$ is $C_{1-4}$alkylene, optionally substituted by alkyl, alkenyl, alkynyl, cycloalkyl, cycloalkylalkyl, cycloalkenyl, cycloalkenylalkyl, aryl, arylalkyl, heteroaryl, heteroarylalkyl, heterocycloalkyl or heterocycloalkylalkyl.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21,p283 "Bioisosterism In Drug Design"; Yun, Hwahak Sekye, 1993,33,p576–579 "Application Of Bioisosterism To New Drug Design"; Zhao, Huaxue Tongbao, 1995,p34–38 "Bioisosteric Replacement And Development Of Lead Compounds In Drug Design"; Graham, Theochem, 1995,343,p105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "corresponding protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups, ethers of hydroxy groups, thioethers of mercapto groups and N-benzyl derivatives of imidazoles.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxyalkoxy" means an alkyl-O-alkyl-O— group wherein the alkyl groups independently are as defined above. Examples of alkoxyalkoxyl include methoxymethoxy, methoxyethoxy, ethoxyethoxy and the like.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is $C_{1-4}$alkyl.

"Alkylsulphonyl" means an alkyl-SO$_2$— group in which the alkyl group is as previously described. Preferred alkylsulphonyl groups are those in which the alkyl group is $C_{1-4}$alkyl.

"Alkylsulphonylcarbamoyl" means an alkyl-SO$_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include ethynylene and propynylene.

"Amino acid side chains" means the substituent found on the carbon between the amino and carboxy groups in α-amino acids. For examples of "corresponding protected derivatives" of amino acid side chains, see T. W. Greene and P. G. M. Wuts in "Protective Groups in Organic Chemistry" John Wiley and Sons, 1991.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^4Y^5N—$, $Y^4Y^5NCO—$, $Y^4Y^5NSO_2—$ (where $Y^4$ and $Y^5$ are independently hydrogen, alkyl, aryl, arylalkyl, heteroaryl and heteroarylalkyl), $Y^4Y^5N—C_{2-6}alkylene-Z^3—$ {where $Z^3$ is O, $NR^6$ or $S(O)_n$}, $alkylC(=O)—Y^4N—$, $alkylSO_2—Y^4N—$ or alkyl optionally substituted with aryl, heteroaryl, hydroxy, or $Y^4Y^5N—$. When $L^2$ contains an optionally substituted aryl group, this may particularly represent optionally substituted phenyl.

"Arylalkenyl" means an aryl-alkenyl group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl-group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl-group in which the aryl and alkynyl are as previously described. Exemplary arylalkynyl groups include phenylethynyl and 3-phenylbut-2-ynyl.

"Arylene" means an optionally substituted bivalent radical derived from an aryl group. Exemplary arylene groups include optionally substituted phenylene, naphthylene and indanylene. When $Ar^1$ is arylene this may particularly represent an optionally substituted phenylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of azaheteroaryl groups include pyridyl, pyrimidinyl, quinolinyl, isoquinolinyl, quinazolinyl, imidazolyl, and benzimidazolyl.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl-group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from an unsaturated monocyclic hydrocarbon of about 3 to about 10 carbon atoms by removing a hydrogen atom from each of two different carbon atoms of the ring. Exemplary cycloalkenylene radicals include cyclopentenylene and cyclohexenylene.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above. When $L^2$ contains an optionally substituted heteroaryl group this may particularly represent an optionally substituted "azaheteroaryl" group.

"Heteroarylalkenyl" means a heteroaryl-alkenyl-group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl-group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from an aromatic monocyclic or multicyclic organic moiety of about 5 to about 10 ring members in which one or more of the ring members is/are element(s) other than carbon, for example nitrogen, oxygen or sulphur, and optionally substituted by one or more "aryl group substituents" as defined above. When $Ar^1$ is a heteroaryldiyl radical this may particularly represent an optionally substituted pyridindiyl.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms selected from O, S or $NY^6$ (where $Y^6$ is hydrogen, alkyl, arylalkyl, and aryl); (ii) an optionally substituted partially saturated multicyclic heterocarbocyclic moiety in which an aryl (or heteroaryl ring) and a heterocycloalkyl group are fused together to form a cyclic structure (examples of such groups include chromanyl, dihydrobenzofuranyl, indolinyl and pyrindolinyl groups, "Heterocycloalkylalkyl" means a heterocycloalkyl-alkyl-group in which the heterocycloalkyl and alkyl moieties are as previously described.

"Heterocycloalkylene" means a bivalent radical derived from a saturated monocyclic hydrocarbon of about 5 to about 7 atoms, which contains one or more heteroatoms selected from O, S or $NY^6$ (where $Y^6$ is hydrogen, alkyl, arylalkyl, and aryl) and optionally substituted by oxo, by removing a hydrogen atom from each of two different carbon atoms of the ring, or when $NY^6$ is NH by removing a hydrogen atom from one carbon atom of the ring and a hydrogen atom from the NH, or when the ring contains two $NY^6$ heteroatoms and $NY^6$ is NH by removing a hydrogen atom from both nitrogen atoms.

"$Y^4Y^5N$—" means a substituted or unsubstituted amino group, wherein $Y^4$ and $Y^5$ are as previously described. Exemplary groups include amino ($H_2N$—), methylamino, ethylmethylamino, dimethylamino and diethylamino.

"$Y^4Y^5NCO$—" means a substituted or unsubstituted carbamoyl group, wherein $Y^4$ and $Y^5$ are as previously described. Exemplary groups are carbamoyl ($H_2NCO$—) and dimethylcarbamoyl ($Me_2NCO$—).

"$Y^4Y^5NSO_2$—" means a substituted or unsubstituted sulphamoyl group, wherein $Y^4$ and $Y_5$ are as previously described. Exemplary groups are sulphamoyl ($H_2NSO_2$—) and dimethylsulphamoyl ($Me_2NSO_2$—).

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent hydrogen, especially when $X^1$ represents C—$R^{10}$ where $R^{10}$ is lower alkyl, lower alkoxy, lower alkylthio, lower alkylsulphinyl or lower alkylsulphonyl.

$R^1$ may also particularly represent halogen, especially fluoro and chloro.

$R^1$ may also particularly represent lower alkyl (e.g. methyl), especially when $X^1$ represents N.

$R^1$ may also particularly represent lower alkoxy (e.g. methoxy), especially when $X^1$ represents N.

$X^1$ may particularly represent $CR^{10}$, especially where $R^{10}$ is lower alkyl or lower alkoxy (e.g. methyl or methoxy).

$X^1$ may also particularly represent N.

$X^2$ may particularly represent $CR^{10}$, especially where $R^{10}$ is lower alkyl (e.g. methyl), lower alkoxy (e.g. methoxy), lower alkylthio (e.g. methylthio), lower alkylsulphinyl (e.g. methylsulphinyl) or lower alkylsulphonyl (e.g. methylsulphonyl).

$X^3$ may particularly represent CH.

$X^3$ may also particularly represent N.

$X^6$ may particularly represent $CR^{10}$ and is preferably CH.

One of $X^4$ and $X^5$ may particularly represent $CR^{11}$ and the other represents $CR^{10}$, especially CH.

Within $R^{11}$ the moiety $L^1$ may particularly represent a —$R^2$—$R^3$— linkage where $R^2$ represents a straight or branched $C_{1-6}$alkylene chain, especially a straight or branched $C_{1-4}$alkylene chain, and $R^3$ represents (a) —C(=Z)—$NR^4$—, preferably —C(=O)—NH—, or (b) —$Z^1$—, preferably —O—.

Within $R^{11}$ the moiety $Ar^1$ may particularly represent (a) an optionally substituted arylene, such as optionally substituted m- or p-phenylene, preferably optionally substituted p-phenylene or (b) an optionally substituted heteroaryldiyl, such as optionally substituted pyridindiyl, preferably a p-pyridindiyl, more preferably a pyridin-2,5-diyl. Preferred optional substituents include $C_{1-4}$alkyl, especially methyl, and $C_{1-4}$alkoxy, especially methoxy.

Within $R^{11}$ the moiety $L^2$ may particularly represent (a) a direct bond (b) an optionally substituted alkylene linkage, especially optionally substituted ethylene (c) an unsubstituted alkenylene linkage, especially vinylene or (d) a —$Z^2$—$R^9$— linkage, such as —O—$CH_2$—, —S(O)$_n$—$CH_2$—, —S(O)$_n$—$CH_2$—$CH_2$—, or especially —NH—$CH_2$—. Preferred optional substituents within (b) include lower alkyl (e.g. methyl), aryl, heteroaryl, —N($R^{12}$)—C(=O)—$R^{13}$, —N($R^{12}$)—C(=O)—$OR^{13}$, —N($R^{12}$)—$SO_2$—$R^{13}$, —$NY^1Y^2$ and —[C(=O)—N($R^6$)—C($R^4$)($R^7$)]$_p$—C(=O)—$NY^1Y^2$. $L^2$ is preferably a group

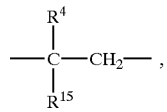

where $R^4$ is hydrogen or lower alkyl (e.g. methyl) and $R^{15}$ represents lower alkyl (e.g. methyl), or where $R^4$ is hydrogen and $R^{15}$ represents aryl, heteroaryl, —N($R^{12}$)—C(=O)—$R^{13}$, —N($R^{12}$)—C(=O)—$OR^{13}$, —N($R^{12}$)—$SO_2$—$R^{13}$, —$NY^1Y^2$ or —[C(=O)—N($R^6$)—C($R^4$)($R^7$)]$_p$—C(=O)—$NY^1Y^2$. $L^2$ is more preferably a group

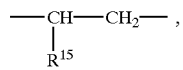

particularly

where $R^{15}$ represents —N($R^{12}$)—C(=O)—$R^{13}$, —N($R^{12}$)—C(=O)—$OR^{13}$, —N($R^{12}$)—$SO_2$—$R^{13}$ or —$NY^1Y^2$.

Within $R^{11}$ the moiety Y may particularly represent carboxy or an acid bioisostere.

It is to be understood that this invention covers all appropriate combinations of the particular and preferred groupings referred to herein.

A particular group of compounds of the invention are compounds of formula (Ia):

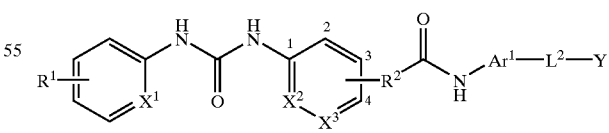

(Ia)

in which $R^1$, $R^2$, $L^2$, $X^1$, $X^2$, $X^3$ and Y are as hereinbefore defined, $Ar^1$ is arylene and —$R^2$—C(=O)—NH—$Ar^1$—$L^2$—Y is attached at the ring 3 or 4 position, and their prodrugs and pharmaceutically acceptable salts, and solvates (e.g. hydrates) of compounds of formula (Ia) and their prodrugs.

Compounds of formula (Ia) in which $R^1$ represents hydrogen are preferred.

Compounds of formula (Ia) in which $R^2$ represents a straight or branched $C_{1-6}$alkylene chain, especially a straight or branched $C_{1-4}$alkylene chain, more especially methylene, are preferred.

Compounds of formula (Ia) in which $Ar^1$ represents an optionally substituted arylene, especially optionally substituted m- or p-phenylene, more especially optionally substituted p-phenylene, are preferred. Preferred substituents for $Ar^1$ include $C_{1-4}$alkyl and $C_{1-4}$alkoxy, especially methyl and methoxy.

Compounds of formula (Ia) in which $L^2$ represents an optionally substituted alkylene linkage, especially ethylene or substituted ethylene, are preferred. Preferred optional substituents include lower alkyl (e.g. methyl), aryl, heteroaryl, $—N(R^{12})—C(=O)—R^{13}$, $—N(R^{12})—C(=O)—OR^{13}$, $—N(R^{12})—SO_2—R^{13}$, $—NY^1Y^2$ or $—[C(=O)—N(R^6)—C(R^4)(R^7)]_p—C(=O)—NY^1Y^2$. Compounds of formula (Ia) in which $L^2$ is a

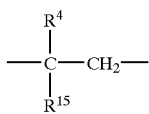

linkage, where $R^4$ is hydrogen or lower alkyl (e.g. methyl) and $R^{15}$ represents lower alkyl (e.g. methyl), or where $R^4$ is hydrogen and $R^{15}$ represents aryl, heteroaryl, $—N(R^{12})—C(=O)—R^{13}$, $—N(R^{12})—C(=O)—OR^{13}$, $—N(R^{12})—SO_2—R^{13}$, $—NY^1Y^2$ and $—[C(=O)—N(R^6)—C(R^4)(R^7)]_p—C(=O)—NY^1Y^2$ are particularly preferred. Compounds of formula (Ia) in which $L^2$ represents a

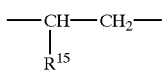

linkage, particularly

where $R^{15}$ represents $—N(R^{12})—C(=O)—R^{13}$, $—N(R^{12})—C(=O)—OR^{13}$, $—N(R^{12})—SO_2—R^{13}$ or $—NY^1Y^2$ are especially preferred.

Compounds of formula (Ia) in which $X^1$ represents $CR^{10}$, especially where $R^{10}$ is lower alkyl or lower alkoxy (e.g. methyl or methoxy), are preferred.

Compounds of formula (Ia) in which $X^2$ represents CR10, especially where $R^{10}$ is lower alkyl (e.g. methyl), lower alkoxy (e.g. methoxy), lower alkylthio (e.g. methylthio), lower alkylsulphinyl (e.g. methylsulphinyl) or lower alkylsulphonyl (e.g. methylsulphonyl), are also preferred.

Compounds of formula (Ia) in which $X^3$ represents CH are also preferred.

Compounds of formula (Ia) in which Y represents carboxy are preferred.

The group $—R^2—C(=O)—NH—Ar^1—L^2—Y$ may preferably be attached at the ring 4 position.

A preferred group of compounds of the invention are compounds of formula (Ia) in which: $R^1$ is hydrogen; $R^2$ is a straight or branched $C_{1-4}$alkylene chain, (especially methylene), $Ar^1$ is an optionally substituted arylene [especially p-phenylene, and methyl(or methoxy) substituted p-phenylene]; $L^2$ is a substituted alkylene linkage [especially

where $R^{15}$ represents $—N(R^{12})—C(=O)—R^{13}$, $—N(R^{12})—C(=O)—OR^{13}$, $—N(R^{12})—SO_2—R^{13}$ or $—NY^1Y^2$]; $X^1$ and $X^2$ represent $CR^{10}$ (especially where $R^{10}$ is methyl, methoxy, methylthio, methylsulphinyl or methylsuphonyl); $X^3$ represents CH; Y represents carboxy; and the group $—R^2—C(=O)—NH—Ar^1—L^2—Y$ is attached at the ring 4 position; and the corresponding N-oxides, and their prodrugs; and pharmaceutically acceptable salts and solvates (e.g. hydrates) of such compounds and their N-oxides and prodrugs.

Compounds of formula (Ia) in which $R^{15}$ represents $—N(R^{12})—C(=O)—R^{13}$, especially where $R^{12}$ is hydrogen or lower alkyl (e.g. methyl) and $R^{13}$ is lower alkyl (e.g. methyl), aryl (e.g. optionally substituted phenyl), heteroaryl (e.g. optionally substituted pyridyl, optionally substituted thienyl, optionally substituted isoxazolyl, optionally substituted pyridazyl), heterocycloalkyl (e.g. tetrahydropyran-4-yl), alkyl substituted by carboxy (e.g. $—CH_2—CH_2—CO_2H$ and $—CH_2—CH_2—CH_2—CO_2H$), alkyl substituted by $—NY^1Y^2$ (e.g. aminomethyl and morpholin-1-ylmethyl) or alkyl substituted by alkoxyalkoxy (e.g. $—CH_2—O—CH_2—CH_2—O—CH_3$) are preferred.

Compounds of formula (Ia) in which $R^{15}$ represents $—N(R^{12})—C(=O)—OR^{13}$, especially where $R^{12}$ is hydrogen or lower alkyl (e.g. methyl) and $R^{13}$ is lower alkyl (e.g. ethyl) or alkyl substituted by aryl (e.g. benzyl), are also preferred.

Compounds of formula (Ia) in which $R^{15}$ represents $—N(R^{12})—SO_2—R^{13}$, especially where $R^{12}$ is hydrogen or lower alkyl (e.g. methyl) and $R^{13}$ is lower alkyl (e.g. methyl), aryl [e.g. optionally substituted phenyl or optionally substituted naphthyl (especially dimethylaminonaphth-1-yl)]), heteroaryl (e.g. optionally substituted pyridyl or optionally substituted imidazolyl), are also preferred.

Compounds of formula (Ia) in which $R^{15}$ represents $—NY^1Y^2$, especially where $Y^1$ and $Y^2$ represent hydrogen are also preferred.

Compounds of formula (Ia) in which $R^{15}$ represents $—NY^1Y^2$, especially where $Y^1$ is hydrogen and $Y^2$ is or lower alkyl (e.g. propyl), or alkyl substituted by aryl (e.g. $—CH_2$-Ph, $—CH(CH_3)$-Ph or $—CH_2—CH_2$-Ph), are also preferred.

Particularly preferred compounds of formula (Ia) are those in which $R^{15}$ is $—NH_2$,

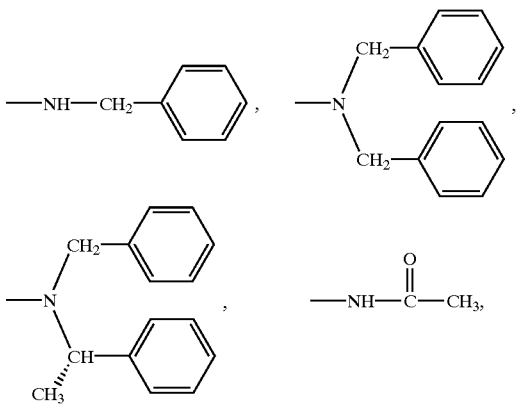

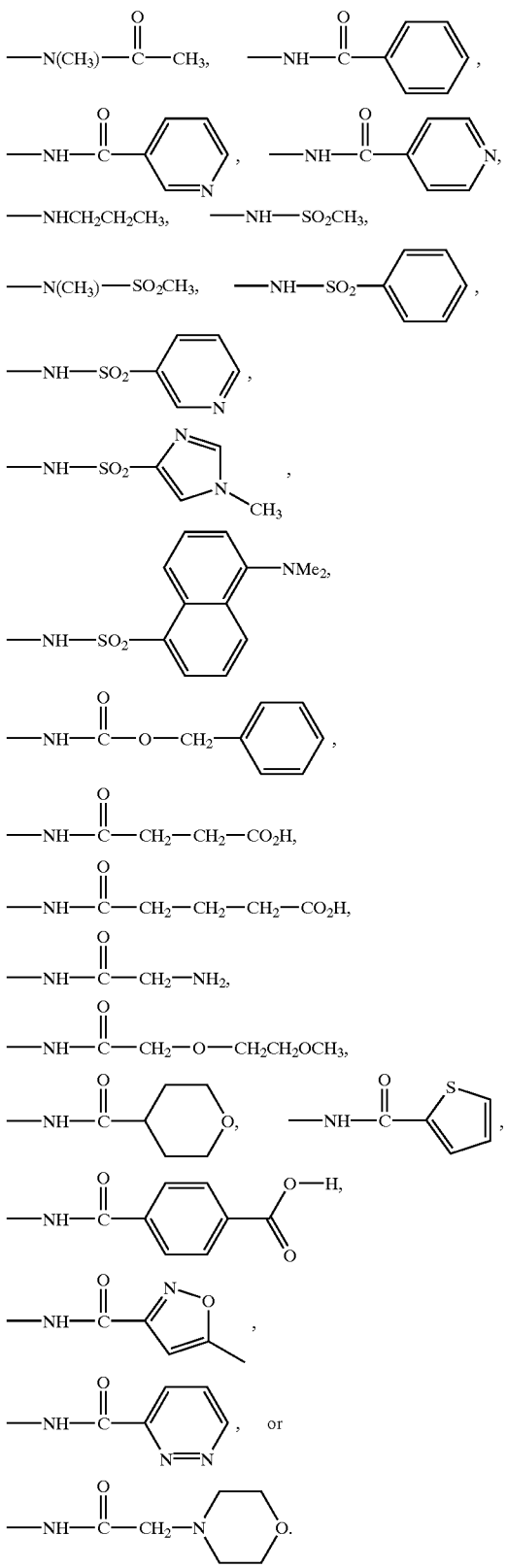

A further particular group of compounds of the invention are compounds of formula (Ib):

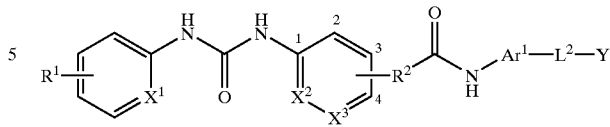

in which $R^1$, $R^2$, $L^2$, $X^1$, $X^2$, $X^3$ and Y are as hereinbefore defined, $Ar^1$ is heteroaryldiyl and —$R^2$—C(=O)—NH—$Ar^1$—$L^2$—Y is attached at the ring 3 or 4 position, and their prodrugs and pharmaceutically acceptable salts, and solvates (e.g. hydrates) of compounds of formula (Ib) and their prodrugs.

Compounds of formula (Ib) in which $R^1$ represents hydrogen are preferred.

Compounds of formula (Ib) in which $R^2$ represents a straight or branched $C_{1-6}$alkylene chain, especially a straight or branched $C_{1-4}$alkylene chain, more especially methylene, are preferred.

Compounds of formula (Ib) in which $Ar^1$ represents an optionally substituted heteroaryldiyl, especially optionally substituted pyridindiyl, more especially optionally substituted p-pyridindiyl, preferably pyridin-2,5-diyl, are also preferred. Preferred substituents include $C_{1-4}$alkyl and $C_{1-4}$alkoxy, especially methyl and methoxy.

Compounds of formula (Ib) in which $L^2$ represents an optionally substituted alkylene linkage, especially ethylene or substituted ethylene, are preferred. Preferred optional substituents include lower alkyl (e.g. methyl), aryl, heteroaryl, —N($R^{12}$)—C(=O)—$R^{13}$, —N($R^{12}$)—C(=O)—O$R^{13}$, —N($R^{12}$)—$SO_2$—$R^{13}$, —$NY^1Y^2$ or —[C(=O)—N($R^6$)—C($R^4$)($R^7$)]$_p$—C(=O)—$NY^1Y^2$. Compounds of formula (Ib) in which $L^2$ is a

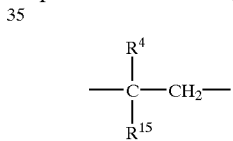

linkage, where $R^4$ is hydrogen or lower alkyl (e.g. methyl) and $R^{15}$ represents lower alkyl (e.g. methyl), or where $R^4$ is hydrogen and $R^{15}$ represents aryl, heteroaryl, —N($R^{12}$)—C(=O)—$R^{13}$, —N($R^{12}$)—C(=O)—O$R^{13}$, —N($R^{12}$)—$SO_2$—$R^{13}$, —$NY^1Y^2$ and —[C(=O)—N($R^6$)—C($R^4$)($R^7$)]$_p$—C(=O)—$NY^1Y^2$ are particularly preferred. Compounds of formula (Ib) in which $L^2$ represents a

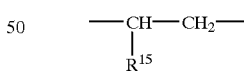

linkage, particularly

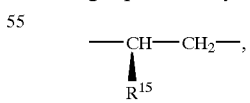

where $R^{15}$ represents —N($R^{12}$)—C(=O)—$R^{13}$, —N($R^{12}$)—C(=O)—O$R^{13}$, —N($R^{12}$)—$SO_2$—$R^{13}$ or —$NY^1Y^2$ are especially preferred.

Compounds of formula (Ib) in which $X^1$ represents $CR^{10}$, especially where $R^{10}$ is lower alkyl or lower alkoxy(e.g. methyl or methoxy), are preferred.

Compounds of formula (Ib) in which $X^2$ represents $CR^{10}$, especially where $R^{10}$ is lower alkyl (e.g. methyl), lower alkoxy (e.g. methoxy), lower alkylthio (e.g. methylthio), lower alkylsulphinyl (e.g. methylsulphinyl) or lower alkylsulphonyl (e.g. methylsulphonyl), are also preferred.

Compounds of formula (Ib) in which $X^3$ represents CH are also preferred.

Compounds of formula (Ib) in which Y represents carboxy are preferred.

The group —$R^2$—C(=O)—NH—$Ar^1$—$L^2$—Y may preferably be attached at the ring 4 position.

A preferred group of compounds of the invention are compounds of formula (Ib) in which: $R^1$ is hydrogen; $R^2$ is a straight or branched $C_{1-4}$alkylene chain, (especially methylene), $Ar^1$ is an optionally substituted heteroaryldiyl, (especially pyridin-2,5-diyl); $L^2$ is an optionally substituted alkylene linkage (especially an ethylene, or a

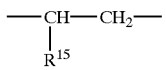

linkage, particularly

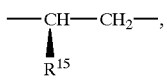

where $R^{15}$ represents methyl, aryl, heteroaryl, —N($R^{12}$)—C(=O)—$R^{13}$, —N($R^{12}$)—C(=O)-O$R^{13}$, —N($R^{12}$)—SO$_2$—$R^{13}$, —N$Y^1Y^2$ and —[C(=O)—N($R^6$)—C($R^4$)($R^7$)]$_p$—C(=O)—N$Y^1Y^2$ [especially —N($R^{12}$)—C(=O)—$R^{13}$, —N($R^{12}$)—C(=O)—O$R^{13}$, —N($R^{12}$)—SO$_2$—$R^{13}$ or —N$Y^1Y^2$]; $X^1$ and $X^2$ represent C$R^{10}$ (especially where $R^{10}$ is methyl, methoxy, methylthio, methylsulphinyl or methylsuphonyl); $X^3$ represents CH; Y represents carboxy; and the group —$R^2$—C(=O)—NH—$Ar^1$—$L^2$—Y is attached at the ring 4 position; and the corresponding N-oxides, and their prodrugs; and pharmaceutically acceptable salts and solvates (e.g. hydrates) of such compounds and their N-oxides and prodrugs.

Compounds of formula (Ib) in which $R^{15}$ represents —N($R^{12}$)—C(=O)—$R^{13}$, especially where $R^{12}$ is hydrogen or lower alkyl (e.g. methyl) and $R^{13}$ is lower alkyl (e.g. methyl), aryl (e.g. optionally substituted phenyl), heteroaryl (e.g. optionally substituted pyridyl, optionally substituted thienyl, optionally substituted isoxazolyl, optionally substituted pyridazyl), heterocycloalkyl (e.g. tetrahydropyran-4-yl), alkyl substituted by carboxy (e.g. —CH$_2$—CH$_2$—CO$_2$H and —CH$_2$—CH$_2$—CH$_2$—CO$_2$H), alkyl substituted by —N$Y^1Y^2$ (e.g. aminomethyl and morpholin-1-ylmethyl) or alkyl substituted by alkoxyalkoxy (e.g. —CH$_2$—O—CH$_2$—CH$_2$—O—CH$_3$) are preferred.

Compounds of formula (Ib) in which $R^{15}$ represents —N($R^{12}$)—C(=O)—O$R^{13}$, especially where $R^{12}$ is hydrogen or lower alkyl (e.g. methyl) and $R^{13}$ is lower alkyl (e.g. ethyl) or alkyl substituted by aryl (e.g. benzyl), are also preferred.

Compounds of formula (Ib) in which $R^{15}$ represents —N($R^{12}$)—SO$_2$—$R^{13}$, especially where $R^{12}$ is hydrogen or lower alkyl (e.g. methyl) and $R^{13}$ is lower alkyl (e.g. methyl), aryl [e.g. optionally substituted phenyl or optionally substituted naphthyl (especially dimethylaminonaphth-1-yl)], heteroaryl (e.g. optionally substituted pyridyl or optionally substituted imidazolyl), are also preferred.

Compounds of formula (Ib) in which $R^{15}$ represents —N$Y^1Y^2$, especially where $Y^1$ and $Y^2$ represent hydrogen are also preferred.

Compounds of formula (Ib) in which $R^{15}$ represents —N$Y^1Y^2$, especially where $Y^1$ is hydrogen and $Y^2$ is or lower alkyl (e.g. propyl), or alkyl substituted by aryl (e.g. —CH$_2$-Ph or —CH$_2$—CH$_2$-Ph), are also preferred.

Compounds of formula (Ib) in which $R^{15}$ represents —N$Y^1Y^2$, especially where both $Y^1$ and $Y^2$ represent alkyl substituted by aryl (e.g. —CH$_2$-Ph or —CH(CH$_3$)-Ph), are also preferred.

Particularly preferred compounds of formula (Ib) are those in which $R^{15}$ is —NH$_2$,

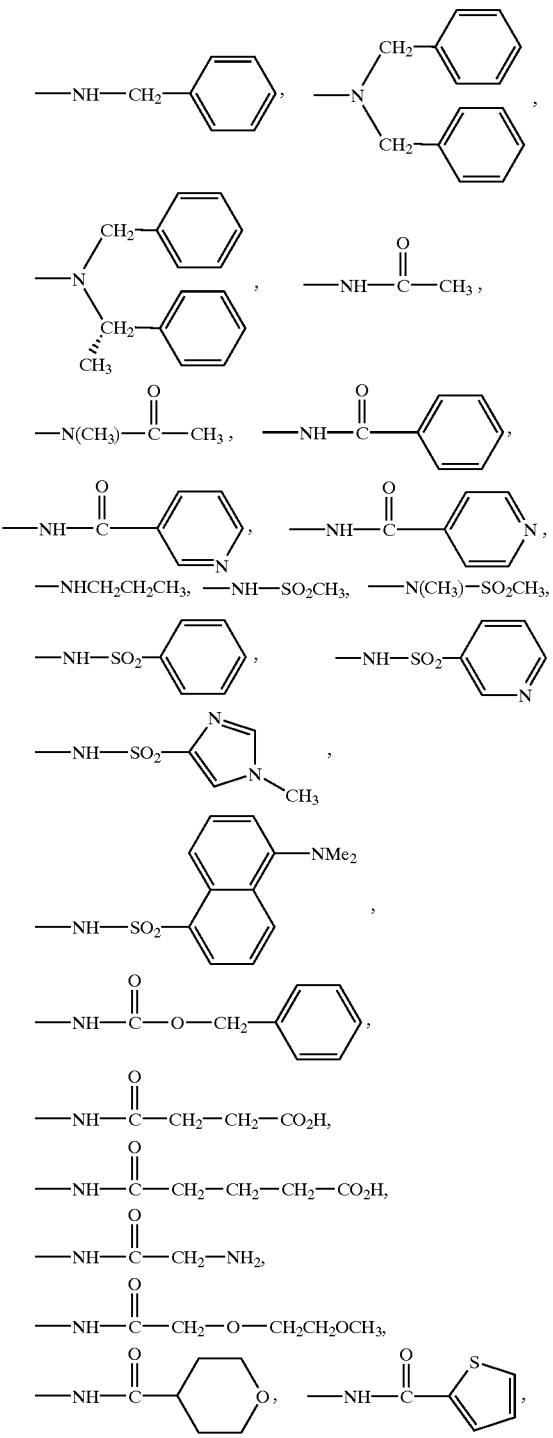

-continued

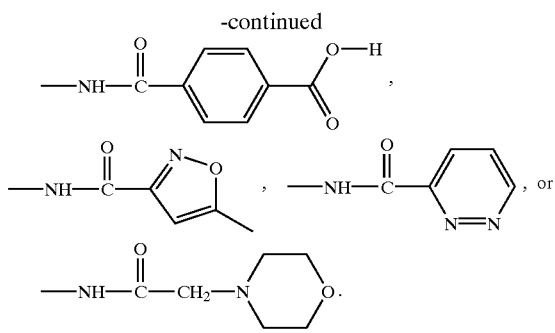

Particular compounds of the invention are selected from the following:

(5-{4-[3-(2-methylphenyl)ureido]-phenylacetylamino}pyrid-2-yl)-thioacetic acid;
3-(5-{3-methoxy-4-[3-(2-methylphenyl)ureido]-phenylacetylamino}pyrid-2-yl)-propanoic acid;
3-(5-{3-methoxy-4-[3-(2-methylphenyl)ureido]-phenylacetylamino}pyrid-2-yl)-2-methyl-propanoic acid;
3-(6-{3-methoxy-4-[3-(2-methylphenyl)ureido]-phenylacetylamino}pyrid-3-yl)-propanoic acid;
3-acetylamino-3-(6-{2-[3-methoxy-4-(3-(2-methylphenyl)ureido)phenyl]-acetylamino})-pyridin-3-yl)-propionic acid;
3-(3,4-dimethoxy-benzoylamino)-3-(6-{2-[3-methoxy-4-(3-(2-methylphenyl)ureido)phenyl]-acetylamino})-pyridin-3-yl)-propionic acid;
N-[2-carboxy-1-(6-{2-[3-methoxy-4-(3-(2-methylphenyl)ureido)phenyl]-acetylamino}-pyridin-3-yl)-ethyl]-terephthalamic acid;
3-benzoylamino-3-(6-{2-[3-methoxy-4-(3-(2-methylphenyl)ureido)phenyl]-acetylamino}-pyridin-3-yl)-propionic acid;
3-(6-{2-[3-methoxy-4-(3-(2-methylphenyl)ureido)phenyl]-acetylamino}-pyridin-3-yl)-3-[(tetrahydro-pyran-4-carbonyl)-amino]-propionic acid;
3-(6-{2-[3-methoxy-4-(3-(2-methylphenyl)ureido)phenyl]-acetylamino}-pyridin-3-yl)-[(pyridazine-3-carbonyl)-amino]-propionic acid;
3-(6-{2-[3-methoxy-4-(3-(2-methylphenyl)ureido)phenyl]-acetylamino}-pyridin-3-yl)-3-[(thiophene-2-carbonyl)-amino]-propionic acid;
N-[2-carboxy-1-(6-{2-[3-methoxy-4-(3-(2-methylphenyl)ureido)phenyl]-acetylamino}-pyridin-3-yl)-ethyl]-succinamic acid;
4-[2-carboxy-1-(6-{2-[3-methoxy-4-(3-(2-methylphenyl)ureido)phenyl]-acetylamino}-pyridin-3-yl)-ethylcarbamoyl]-butyric acid;
3-(2-amino-acetylamino)-3-(6-{2-[3-methoxy-4-(3-(2-methylphenyl)ureido)phenyl]-acetylamino}-pyridin-3-yl)-propionic acid;
3-(6-{2-[3-methoxy-4-(3-(2-methylphenyl)ureido)phenyl]-acetylamino}-pyridin-3-yl)-3-(2-morpholin-4-yl-acetylamino)-propionic acid;
3-[2-(2-methoxy-ethoxy)-acetylamino]-3-(6-{2-[3-methoxy-4-(3-(2-methylphenyl)ureido)phenyl]-acetylamino}-pyridin-3-yl)-propionic acid;
3-methanesulfonylamino-3-(6-{2-[3-methoxy-4-(3-(2-methylphenyl)ureido)phenyl]-acetylamino}-pyridin-3-yl)-propionic acid;
3-(6-{2-[3-methoxy-4-(3-(2-methylphenyl)ureido)phenyl]-acetylamino}-pyridin-3-yl)-3-(pyridine-3-sulfonylamino)-propionic acid;
3-(6-{2-[3-methoxy-4-(3-(2-methylphenyl)ureido)phenyl]-acetylamino}-pyridin-3-yl)-3-(1-methyl-5H-imidazole-4-sulfonylamino)-propionic acid;

3-acetylamino-3-[6-({[3-methoxy-4-(3-(2-methylphenyl)ureido)phenyl]-acetyl}-methyl-amino)-pyridin-3-yl]-propionic acid;
3-(3,4-dimethoxy-benzoylamino)-3-[6-({[3-methoxy-4-(3-(2-methylphenyl)ureido)phenyl]-acetyl}-methyl-amino)pyridin-3-yl]-propionic acid;
N-{2-carboxy-1-[6-({[3-methoxy-4-(3-(2-methylphenyl)ureido)phenyl]-acetyl}-methyl-amino)-pyridin-3-yl]-ethyl}-terephthalamic acid;
3-benzoylamino-3-[6-({[3-methoxy-4-(3-(2-methylphenyl)ureido)phenyl]-acetyl}-methyl-amino)-pyridin-3-yl]-propionic acid;
3-[6-({[3-methoxy-4-(3-(2-methylphenyl)ureido)phenyl]-acetyl}-methyl-amino)-pyridin-3-yl]-3-[(tetrahydro-pyran-4-carbonyl)-amino]-propionic acid;
3-[6-({[3-methoxy-4-(3-(2-methylphenyl)ureido)phenyl]-acetyl}-methyl-amino)-pyridin-3-yl]-3-[(pyridazine-3-carbonyl)-amino]-propionic acid;
3-[6-({[3-methoxy-4-(3-(2-methylphenyl)ureido)phenyl]-acetyl}-methyl-amino)-pyridin-3-yl]-3-[(thiophene-2-carbonyl)-amino]-propionic acid;
N-{2-carboxy-1-[6-({[3-methoxy-4-(3-(2-methylphenyl)ureido)phenyl]-acetyl}-methyl-amino)-pyridin-3-yl]-ethyl}-succinamic acid;
4-{2-carboxy-1-[6-({[3-methoxy-4-(3-(2-methylphenyl)ureido)phenyl]-acetyl}-methyl-amino)-pyridin-3-yl]-ethylcarbamoyl}-butyric acid;
3-(2-amino-acetylamino)-3-[6-({[3-methoxy-4-(3-(2-methylphenyl)ureido)phenyl]-acetyl}-methyl-amino)-pyridin-3-yl]-propionic acid;
3-[6-({[3-methoxy-4-(3-(2-methylphenyl)ureido)phenyl]-acetyl}-methyl-amino)-pyridin-3-yl]-3-(2-morpholin-4-yl-acetylamino)-propionic acid;
3-[2-(2-methoxy-ethoxy)-acetylamino]-3-[6-({[3-methoxy-4-(3-(2-methylphenyl)ureido)phenyl]-acetyl}-methyl-amino)-pyridin-3-yl]-propionic acid;
3-methanesulfonylamino-3-[6-({[3-methoxy-4-(3-(2-methylphenyl)ureido)phenyl]-acetyl }-methyl-amino)-pyridin-3-yl]-propionic acid;
3-[6-({[3-methoxy-4-(3-(2-methylphenyl)ureido)phenyl]-acetyl}-methyl-amino)-pyridin-3-yl]-3-(pyridine-3-sulfonylamino)-propionic acid;
3-[6-({[3-methoxy-4-(3-(2-methylphenyl)ureido)phenyl]-acetyl}-methyl-amino)-pyridin-3-yl]-3-(1-methyl-5H-imidazole-4-sulfonylamino)-propionic acid;
3-(acetyl-methyl-amino)-3-(6-{2-[3-methoxy-4-(3-(2-methylphenyl)ureido)phenyl]-acetylamino}-pyridin-3-yl)-propionic acid;
3-[(3,4-dimethoxy-benzoyl)-methyl-amino]-3-(6-{2-[3-methoxy-4-(3-(2-methylphenyl)ureido)-phenyl]-acetylamino}-pyridin-3-yl)-propionic acid;
N-[2-carboxy-1-(6-{2-[3-methoxy-4-(3-(2-methylphenyl)ureido)phenyl]-acetylamino}-pyridin-3-yl)-ethyl]-N-methyl-terephthalamic acid;
3-(benzoyl-methyl-amino)-3-(6-{2-[3-methoxy-4-(3-(2-methylphenyl)ureido)phenyl]-acetylamino}-pyridin-3-yl)-propionic acid;
3-(6-{2-[3-methoxy-4-(3-(2-methylphenyl)ureido)phenyl]-acetylamino}-pyridin-3-yl)-3-[methyl-(tetrahydro-pyran-4-carbonyl)-amino]-propionic acid;
3-(6-{2-[3-methoxy-4-(3-(2-methylphenyl)ureido)phenyl]-acetylamino}-pyridin-3-yl)-3-[methyl-(pyridazine-3-carbonyl)-amino]-propionic acid;
3-(6-{2-[3-methoxy-4-(3-(2-methylphenyl)ureido)phenyl]-acetylamino}-pyridin-3-yl)-3-[methyl-(thiophene-2-carbonyl)-amino]-propionic acid;
N-[2-carboxy-1-(6-{2-[3-methoxy-4-(3-(2-methylphenyl)ureido)phenyl]-acetylamino}-pyridin-3-yl)-ethyl]-N-methyl-succinamic acid;

4-{[2-carboxy-1-(6-{2-[3-methoxy-4-(3-(2-methylphenyl)ureido)phenyl]-acetylamino}-pyridin-3-yl)-ethyl]-methyl-carbamoyl}-butyric acid;

3-(aminoacetyl-methyl-amino)-3-(6-{2-[3-methoxy-4-(3-(2-methylphenyl)ureido)phenyl]-acetylamino}-pyridin-3-yl)-propionic acid;

3-(6-{2-[3-methoxy-4-(3-(2-methylphenyl)ureido)phenyl]-acetylamino}-pyridin-3-yl)-3-[methyl-(morpholin-4-yl-acetyl)-amino]-propionic acid;

3-{[(2-methoxy-ethoxy)-acetyl]-methyl-amino}-3-(6-{2-[3-methoxy-4-(3-(2-methylphenyl)ureido)phenyl]-acetylamino}-pyridin-3-yl)-propionic acid;

3-(methanesulfonyl-methyl-amino)-3-(6-{2-[3-methoxy-4-(3-(2-methylphenyl)ureido)phenyl]-acetylamino}-pyridin-3-yl)-propionic acid;

3-(6-{2-[3-methoxy-4-(3-(2-methylphenyl)ureido)phenyl]-acetylamino)}-pyridin-3-yl)-3-[methyl-(pyridine-3-sulfonyl)-amino]-propionic acid;

3-(6-{2-[3-methoxy-4-(3-(2-methylphenyl)ureido)phenyl]-acetylamino}-pyridin-3-yl)-3-[methyl-(1-methyl-5H-imidazole-4-sulfonyl)-amino]-propionic acid;

3-acetylamino-3-(6-{2-[4-(3-(2-methylphenyl)ureido)phenyl]-acetylamino}-pyridin-3-yl)-propionic acid;

3-(3,4-dimethoxy-benzoylamino)-3-(6-{2-[4-(3-(2-methylphenyl)ureido)phenyl]-acetylamino}-pyridin-3-yl)-propionic acid;

N-[2-carboxy-1-(6-{2-[4-(3-(2-methylphenyl)ureido)phenyl]-acetylamino}-pyridin-3-yl)-ethyl]-terephthalamic acid;

3-benzoylamino-3-(6-{2-[4-(3-(2-methylphenyl)ureido)phenyl]-acetylamino}-pyridin-3-yl)-propionic acid;

3-[(tetrahydro-pyran-4-carbonyl)-amino]-3-(6-{2-[4-(3-(2-methylphenyl)ureido)phenyl]-acetylamino}-pyridin-3-yl)-propionic acid;

3-[(pyridazine-3-carbonyl)-amino]-3-(6-{2-[4-(3-(2-methylphenyl)ureido)phenyl]-acetylamino}-pyridin-3-yl)-propionic acid;

3-[(thiophene-2-carbonyl)-amino]-3-(6-{2-[4-(3-(2-methylphenyl)ureido)phenyl]-acetylamino}-pyridin-3-yl)-propionic acid;

N-[2-carboxy-1-(6-{2-[4-(3-(2-methylphenyl)ureido)phenyl]-acetylamino}-pyridin-3-yl)-ethyl]-succinamic acid;

4-[2-carboxy-1-(6-{2-[4-(3-(2-methylphenyl)ureido)phenyl]-acetylamino}-pyridin-3-yl)-ethylcarbamoyl]-butyric acid;

3-(2-amino-acetylamino)-3-(6-{2-[4-(3-(2-methylphenyl)ureido)phenyl]-acetylamino}-pyridin-3-yl)-propionic acid;

3-(2-morpholin-4-yl-acetylamino)-3-(6-{2-[4-(3-(2-methylphenyl)ureido)phenyl]-acetylamino}-pyridin-3-yl)-propionic acid;

3-[2-(2-methoxy-ethoxy)-acetylamino]-3-(6-{2-[4-(3-(2-methylphenyl)ureido)phenyl]-acetylamino}-pyridin-3-yl)-propionic acid;

3-methanesulfonylamino-3-(6-{2-[4-(3-(2-methylphenyl)ureido)phenyl]-acetylamino}-pyridin-3-yl)-propionic acid;

3-(pyridine-3-sulfonylamino)-3-(6-{2-[4-(3-(2-methylphenyl)ureido)phenyl]-acetylamino}-pyridin-3-yl)-propionic acid;

3-(1-methyl-5H-imidazole-4-sulfonylamino)-3-(6-{2-[4-(3-(2-methylphenyl)ureido)phenyl]-acetylamino}-pyridin-3-yl)-propionic acid;

3-(acetyl-methyl-amino)-3-[6-({[3-methoxy-4-(3-(2-methylphenyl)ureido)phenyl]-acetyl}-methyl-amino)-pyridin-3-yl]-propionic acid;

3-[(3,4-dimethoxy-benzoyl)-methyl-amino]-3-[6-({[3-methoxy-4-(3-(2-methylphenyl)ureido)phenyl]-acetyl}-methyl-amino)-pyridin-3-yl]-propionic acid;

N-{2-carboxy-1-[6-({[3-methoxy-4-(3-(2-methylphenyl)ureido)phenyl]-acetyl}-methyl-amino)-pyridin-3-yl]-ethyl}-N-methyl-terephthalamic acid;

3-(benzoyl-methyl-amino)-3-[6-({[3-methoxy-4-(3-(2-methylphenyl)ureido)phenyl]-acetyl}-methyl-amino)pyridin-3-yl]-propionic acid;

3-[6-({[3-methoxy-4-(3-(2-methylphenyl)ureido)phenyl]-acetyl}-methyl-amino)-pyridin-3-yl]-3-[methyl-(tetrahydro-pyran-4-carbonyl)-amino]-propionic acid;

3-[6-({[3-methoxy-4-(3-(2-methylphenyl)ureido)phenyl]-acetyl}-methyl-amino)-pyridin-3-yl]-3-[methyl-(pyridazine-3-carbonyl)-amino]-propionic acid;

3-[6-({[3-methoxy-4-(3-(2-methylphenyl)ureido)phenyl]-acetyl}-methyl-amino)-pyridin-3-yl]-3-[methyl-(thiophene-2-carbonyl)-amino]-propionic acid;

N-{2-carboxy-1-[6-({[3-methoxy-4-(3-(2-methylphenyl)ureido)phenyl]-acetyl}-methyl-amino)-pyridin-3-yl]-ethyl}-N-methyl-succinamic acid;

4-({2-carboxy-1-[6-({[3-methoxy-4-(3-(2-methylphenyl)ureido)phenyl]-acetyl}-methyl-amino)-pyridin-3-yl]-ethyl}-methyl-carbamoyl)-butyric acid;

3-(aminoacetyl-methyl-amino)-3-[6-({[3-methoxy-4-(3-(2-methylphenyl)ureido)phenyl]-acetyl}-methyl-amino)pyridin-3-yl]-propionic acid;

3-[6-({[3-methoxy-4-(3-(2-methylphenyl)ureido)phenyl]-acetyl}-methyl-amino)-pyridin-3-yl]-3-[methyl-(morpholin-4-yl-acetyl)-amino]-propionic acid;

3-{[(2-methoxy-ethoxy)-acetyl]-methyl-amino}-3-[6-({[3-methoxy-4-(3-(2-methylphenyl)ureido)phenyl]-acetyl}-methyl-amino)-pyridin-3-yl]-propionic acid;

3-(methanesulfonyl-methyl-amino)-3-[6-({[3-methoxy-4-(3-(2-methylphenyl)ureido)phenyl]-acetyl}-methyl-amino)-pyridin-3-yl]-propionic acid;

3-[6-({[3-methoxy-4-(3-(2-methylphenyl)ureido)phenyl]-acetyl}-methyl-amino)-pyridin-3-yl]-3-[methyl-(pyridine-3-sulfonyl)-amino]-propionic acid;

3-[6-({[3-methoxy-4-(3-(2-methylphenyl)ureido)phenyl]-acetyl}-methyl-amino)-pyridin-3-yl]-3-[methyl-(1-methyl-5H-imidazole-4-sulfonyl)-amino]-propionic acid;

3-acetylamino-3-(5-{2-[3-methoxy-4-(3-(2-methylphenyl)ureido)phenyl]-acetylamino}-pyridin-2-yl)-propionic acid.

3-(3,4-dimethoxy-benzoylamino)-3-(5-{2-[3-methoxy-4-(3-(2-methylphenyl)ureido)phenyl]-acetylamino}-pyridin-2-yl)-propionic acid;

N-[2-carboxy-1-(5-{2-[3-methoxy-4-(3-(2-methylphenyl)ureido)phenyl]-acetylamino}-pyridin-2-yl)-ethyl]-terephthalamic acid;

3-benzoylamino-3-(5-{2-[3-methoxy-4-(3-(2-methylphenyl)ureido)phenyl]-acetylamino}-pyridin-2-yl)-propionic acid;

3-(5-{2-[3-methoxy-4-(3-(2-methylphenyl)ureido)phenyl]-acetylamino)}-pyridin-2-yl)-3-[(tetrahydropyran-4-carbonyl)-amino]-propionic acid;

3-(5-{2-[3-methoxy-4-(3-(2-methylphenyl)ureido)phenyl]-acetylamino}-pyridin-2-yl)-3-[(pyridazine-3-carbonyl)-amino]-propionic acid;

3-(5-{2-[3-methoxy-4-(3-(2-methylphenyl)ureido)phenyl]-acetylamino}-pyridin-2-yl)-3-[(thiophene-2-carbonyl)-amino]-propionic acid;

N-[2-carboxy-1-(5-{2-[3-methoxy-4-(3-(2-methylphenyl)ureido)phenyl]-acetylamino}-pyridin-2-yl)-ethyl]-succinamic acid;

4-[2-carboxy-1-(5-{2-[3-methoxy-4-(3-(2-methylphenyl)ureido)phenyl]-acetylamino}-pyridin-2-yl)-ethylcarbamoyl]-butyric acid;

3-(2-amino-acetylamino)-3-(5-{2-[3-methoxy-4-(3-(2-methylphenyl)ureido)phenyl]-acetylamino}-pyridin-2-yl)-propionic acid;
3-(5-{2-[3-methoxy-4-(3-(2-methylphenyl)ureido)phenyl]-acetylamino}-pyridin-2-yl)-3-(2-morpholin-4-yl-acetylamino)-propionic acid;
3-[2-(2-methoxy-ethoxy)-acetylamino]-3-(5-{2-[3-methoxy-4-(3-(2-methylphenyl)ureido)phenyl]-acetylamino}-pyridin-2-yl)-propionic acid;
3-methanesulfonylamino-3-(5-{2-[3-methoxy-4-(3-(2-methylphenyl)ureido)phenyl]-acetylamino}-pyridin-2-yl)-propionic acid;
3-(5-{2-[3-methoxy-4-(3-(2-methylphenyl)ureido)phenyl]-acetylamino}-pyridin-2-yl)-3-(pyridine-3-sulfonylamino)-propionic acid;
3-(5-{2-[3-methoxy-4-(3-(2-methylphenyl)ureido)phenyl]-acetylamino}-pyridin-2-yl)-3-(1-methyl-5H-imidazole-4-sulfonylamino)-propionic acid;
3-acetylamino-3-[5-({[3-methoxy-4-(3-(2-methylphenyl)ureido)phenyl]-acetyl}-methyl-amino)-pyridin-2-yl]-propionic acid;
3-(3,4-dimethoxy-benzoylamino)-3-[5-({[3-methoxy-4-(3-(2-methylphenyl)ureido)phenyl]-acetyl}-methyl-amino)-pyridin-2-yl]-propionic acid;
N-{2-carboxy-1-[5-({[3-methoxy-4-(3-(2-methylphenyl)ureido)phenyl]-acetyl}-methyl-amino)-pyridin-2-yl]-ethyl}-terephthalamic acid;
3-benzoylamino-3-[5-({[3-methoxy-4-(3-(2-methylphenyl)ureido)phenyl]-acetyl}-methyl-amino)-pyridin-2-yl]-propionic acid;
3-[5-({[3-methoxy-4-(3-(2-methylphenyl)ureido)phenyl]-acetyl}-methyl-amino)-pyridin-2-yl]-3-[(tetrahydro-pyran-4-carbonyl)-amino]-propionic acid;
3-[5-({[3-methoxy-4-(3-(2-methylphenyl)ureido)phenyl]-acetyl}-methyl-amino)-pyridin-2-yl]-3-[(pyridazine-3-carbonyl)-amino]-propionic acid;
3-[5-({[3-methoxy-4-(3-(2-methylphenyl)ureido)phenyl]-acetyl}-methyl-amino)-pyridin-2-yl]-3-[(thiophene-2-carbonyl)-amino]-propionic acid;
N-{2-carboxy-1-[5-({[3-methoxy-4-(3-(2-methylphenyl)ureido)phenyl]-acetyl}-methyl-amino)-pyridin-2-yl]-ethyl}-succinamic acid;
4-{2-carboxy-1-[5-({[3-methoxy-4-(3-(2-methylphenyl)ureido)phenyl]-acetyl}-methyl-amino)-pyridin-2-yl]-ethylcarbamoyl}-butyric acid;
3-(2-amino-acetylamino)-3-[5-({[3-methoxy-4-(3-(2-methylphenyl)ureido)phenyl]-acetyl}-methyl-amino)pyridin-2-yl]-propionic acid;
3-[5-({[3-methoxy-4-(3-(2-methylphenyl)ureido)phenyl]-acetyl}-methyl-amino)-pyridin-2-yl]-3-(2-morpholin-4-yl-acetylamino)-propionic acid;
3-[2-(2-methoxy-ethoxy)-acetylamino]-3-[5-({[3-methoxy-4-(3-(2-methylphenyl)ureido)phenyl]-acetyl}-methyl-amino)-pyridin-2-yl]-propionic acid;
3-methanesulfonylamino-3-[5-({[3-methoxy-4-(3-(2-methylphenyl)ureido)phenyl]-acetyl}-methyl-amino)-pyridin-2-yl]-propionic acid;
3-[5-({[3-methoxy-4-(3-(2-methylphenyl)ureido)phenyl]-acetyl}-methyl-amino)-pyridin-2-yl]-3-(pyridine-3-sulfonylamino)-propionic acid;
3-[5-({[3-methoxy-4-(3-(2-methylphenyl)ureido)phenyl]-acetyl}-methyl-amino)-pyridin-2-yl]-3-(1-methyl-5H-imidazole-4-sulfonylamino)-propionic acid;
3-(acetyl-methyl-amino)-3-(5-{2-[3-methoxy-4-(3-(2-methylphenyl)ureido)phenyl]-acetylamino}-pyridin-2-yl)-propionic acid;
3-[(3,4-dimethoxy-benzoyl)-methyl-amino]-3-(5-{2-[3-methoxy-4-(3-(2-methylphenyl)ureido)-phenyl]-acetylamino}-pyridin-2-yl)-propionic acid;
N-[2-carboxy-1-(5-{2-[3-methoxy-4-(3-(2-methylphenyl)ureido)phenyl]-acetylamino}-pyridin-2-yl)-ethyl]-N-methyl-terephthalamic acid;
3-(benzoyl-methyl-amino)-3-(5-{2-[3-methoxy-4-(3-(2-methylphenyl)ureido)phenyl]-acetylamino}-pyridin-2-yl)-propionic acid;
3-(5-{2-[3-methoxy-4-(3-(2-methylphenyl)ureido)phenyl]-acetylamino}-pyridin-2-yl)-3-[methyl-(tetrahydro-pyran-4-carbonyl)-amino]-propionic acid;
3-(5-{2-[3-methoxy-4-(3-(2-methylphenyl)ureido)phenyl]-acetylamino}-pyridin-2-yl)-3-[methyl-(pyridazine-3-carbonyl)-amino]-propionic acid;
3-(5-{2-[3-methoxy-4-(3-(2-methylphenyl)ureido)phenyl]-acetylamino}-pyridin-2-yl)-3-[methyl-(thiophene-2-carbonyl)-amino]-propionic acid;
N-[2-carboxy-1-(5-{2-[3-methoxy-4-(3-(2-methylphenyl)ureido)phenyl]-acetylamino}-pyridin-2-yl)-ethyl]-N-methyl-succinamic acid;
4-{[2-carboxy-1-(5-{2-[3-methoxy-4-(3-(2-methylphenyl)ureido)phenyl]-acetylamino}-pyridin-2-yl)-ethyl]-methyl-carbamoyl}-butyric acid;
3-(aminoacetyl-methyl-amino)-3-(5-{2-[3-methoxy-4-(3-(2-methylphenyl)ureido)phenyl]-acetylamino}-pyridin-2-yl)-propionic acid;
3-(5-{2-[3-methoxy-4-(3-(2-methylphenyl)ureido)phenyl]-acetylamino}-pyridin-2-yl)-3-[methyl-(morpholin-4-yl-acetyl)-amino]-propionic acid;
3-{[(2-methoxy-ethoxy)-acetyl]-methyl-amino}-3-(5-{2-[3-methoxy-4-(3-(2-methylphenyl)ureido)phenyl]-acetylamino}-pyridin-2-yl)-propionic acid;
3-(methanesulfonyl-methyl-amino)-3-(5-{2-[3-methoxy-4-(3-(2-methylphenyl)ureido)phenyl]-acetylamino}-pyridin-2-yl)-propionic acid;
3-(5-{2-[3-methoxy-4-(3-(2-methylphenyl)ureido)phenyl]-acetylamino}-pyridin-2-yl)-3-[methyl-(pyridine-3-sulfonyl)-amino]-propionic acid;
3-(5-{2-[3-methoxy-4-(3-(2-methylphenyl)ureido)phenyl]-acetylamino}-pyridin-2-yl)-3-[methyl-(1-methyl-5H-imidazole-4-sulfonyl)-amino]-propionic acid;
3-acetylamino-3-(5-{2-[4-(3-(2-methylphenyl)ureido)phenyl]-acetylamino}-pyridin-2-yl)-propionic acid;
3-(3,4-dimethoxy-benzoylamino)-3-(5-{2-[4-(3-(2-methylphenyl)ureido)phenyl]-acetylamino}-pyridin-2-yl)-propionic acid;
N-[2-carboxy-1-(5-{2-[4-(3-(2-methylphenyl)ureido)phenyl]-acetylamino}-pyridin-2-yl)-ethyl]-terephthalamic acid;
3-benzoylamino-3-(5-{2-[4-(3-(2-methylphenyl)ureido)phenyl]-acetylamino}-pyridin-2-yl)-propionic acid;
3-[(tetrahydro-pyran-4-carbonyl)-amino]-3-(5-{2-[4-(3-(2-methylphenyl)ureido)phenyl]-acetylamino}-pyridin-2-yl)-propionic acid;
3-[(pyridazine-3-carbonyl)-amino]-3-(5-{2-[4-(3-(2-methylphenyl)ureido)phenyl]-acetylamino}-pyridin-2-yl)-propionic acid;
3-[(thiophene-2-carbonyl)-amino]-3-(5-{2-[4-(3-(2-methylphenyl)ureido)phenyl]-acetylamino}-pyridin-2-yl)-propionic acid;
N-[2-carboxy-1-(5-{2-[4-(3-(2-methylphenyl)ureido)phenyl]-acetylamino}-pyridin-2-yl)-ethyl]-succinamic acid;
4-[2-carboxy-1-(5-{2-[4-(3-(2-methylphenyl)ureido)phenyl]-acetylamino}-pyridin-2-yl)-ethylcarbamoyl]-butyric acid;
3-(2-amino-acetylamino)-3-(5-{2-[4-(3-(2-methylphenyl)ureido)phenyl]-acetylamino}-pyridin-2-yl)-propionic acid;

3-(2-morpholin-4-yl-acetylamino)-3-(5-{2-[4-(3-(2-methylphenyl)ureido)phenyl]-acetylamino}-pyridin-2-yl)-propionic acid;

3-[2-(2-methoxy-ethoxy)-acetylamino]-3-(5-{2-[4-(3-(2-methylphenyl)ureido)phenyl]-acetylamino}-pyridin-2-yl)-propionic acid;

3-methanesulfonylamino-3-(5-{2-[4-(3-(2-methylphenyl)ureido)phenyl]-acetylamino}-pyridin-2-yl)-propionic acid;

3-(pyridine-3-sulfonylamino)-3-(5-{2-[4-(3-(2-methylphenyl)ureido)phenyl]-acetylamino}-pyridin-2-yl)-propionic acid;

3-(1-methyl-5H-imidazole-4-sulfonylamino)-3-(5-{2-[4-(3-(2-methylphenyl)ureido)phenyl]-acetylamino}-pyridin-2-yl)-propionic acid;

3-(acetyl-methyl-amino)-3-[5-({[3-methoxy-4-(3-(2-methylphenyl)urido)phenyl]-acetyl}-methyl-amino)-pyridin-2-yl]-propionic acid;

3-[(3,4-dimethoxy-benzoyl)-methyl-amino]-3-[5-({[3-methoxy-4-(3-(2-methylphenyl)ureido)-phenyl]-acetyl}-methyl-amino)-pyridin-2-yl]-propionic acid;

N-{2-carboxy-1-[5-({[3-methoxy-4-(3-(2-methylphenyl)ureido)phenyl]-acetyl}-methyl-amino)-pyridin-2-yl]-ethyl}-N-methyl-terephthalamic acid;

3-(benzoyl-methyl-amino)3-[5-({[3-methoxy-4-(3-(2-methylphenyl)ureido)phenyl]-acetyl}-methyl-amino)-pyridin-2-yl]-propionic acid;

3-[5-({[3-methoxy-4-(3-(2-methylphenyl)ureido)phenyl]-acetyl}-methyl-amino)-pyridin-2-yl]-3-[methyl-(tetrahydro-pyran-4-carbonyl)-amino]-propionic acid;

3-[5-({[3-methoxy-4-(3-(2-methylphenyl)ureido)phenyl]-acetyl}-methyl-amino)-pyridin-2-yl]-3-[methyl-(pyridazine-3-carbonyl)-amino]-propionic acid;

3-[5-({[3-methoxy-4-(3-(2-methylphenyl)ureido)phenyl]-acetyl}-methyl-amino)-pyridin-2-yl]-3-[methyl-(thiophene-2-carbonyl)-amino]-propionic acid;

N-{2-carboxy-1-[5-({[3-methoxy-4-(3-(2-methylphenyl)ureido)phenyl]-acetyl}-methyl-amino)-pyridin-2-yl]-ethyl}-N-methyl-succinamic acid;

4-({2-carboxy-1-[5-({[3-methoxy-4-(3-(2-methylphenyl)ureido)phenyl]-acetyl}-methyl-amino)-pyridin-2-yl]-ethyl}-methyl-carbamoyl)-butyric acid;

3-(aminoacetyl-methyl-amino)-3-[5-({[3-methoxy-4-(3-(2-methylphenyl)ureido)phenyl]-acetyl}-methyl-amino)-pyridin-2-yl]-propionic acid;

3-[5-({[3-methoxy-4-(3-(2-methylphenyl)ureido)phenyl]-acetyl}-methyl-amino)-pyridin-2-yl]-3-[methyl-(morpholin-4-yl-acetyl)-amino]-propionic acid;

3-{[(2-methoxy-ethoxy)-acetyl]-methyl-amino}-3-[5-({[3-methoxy-4-(3-(2-methylphenyl(ureido)-phenyl]-acetyl}-methyl-amino)-pyridin-2-yl]-propionic acid;

3-(methanesulfonyl-methyl-amino)-3-[5-({[3-methoxy-4-(3-(2-methylphenyl)ureido)phenyl]-acetyl}-methyl-amino)-pyridin-2-yl]-propionic acid;

3-[5-({[3-methoxy-4-(3-(2-methylphenyl)ureido)phenyl]-acetyl}-methyl-amino)-pyridin-2-yl]-3-[methyl-(pyridine-3-sulfonyl)-amino]-propionic acid;

3-[5-({[3-methoxy-4-(3-(2-methylphenyl)ureido)phenyl]-acetyl}-methyl-amino)-pyridin-2-yl]-3-[methyl-(1-methyl-5H-imidazole-4-sulfonyl)-amino]-propionic acid;

3-(4-{3-methoxy-4-[3-(2-methylphenyl)ureido]phenylacetylamino}phenyl)-3-(methanesulphonylamino)-propanoic acid;

3-(acetylamino)-3-(4-{3-methoxy-4-[3-(2-methylphenyl)ureido]phenylacetylamino}phenyl)-propanoic acid;

3-(benzoylamino)-3-(4-{3-methoxy-4-[3-(2-methylphenyl)ureido]phenylacetylamino}phenyl)-propanoic acid;

3-(4-{3-methoxy-4-[3-(2-methylphenyl)ureido]phenylacetylamino}phenyl)-3-(3-pyridylacetylamino)-propanoic acid;

3-amino-3-(4-{3-methoxy-4-[3-(2-methylphenyl)ureido]phenylacetylamino}phenyl)-propanoic acid;

3-(n-butylamino)-3-(4-{3-methoxy-4-[3-(2-methylphenyl)ureido]phenylacetylamino}phenyl)-propanoic acid;

3-benzylamino-3-(4-{3-methoxy-4-[3-(2-methylphenyl)ureido]phenylacetylamino}phenyl)-propanoic acid;

3-(4-{3-methoxy-4-[3-(2-methylphenyl)ureido]phenylacetylamino}phenyl)-3-(2-phenylethylamino)-propanoic acid;

3-(4-{3-methoxy-4-[3-(2-methylphenyl)ureido]phenylacetylamino}phenyl)-3-(morpholin-4-yl)-propanoic acid;

3-(4-{3-methoxy-4-[3-(2-methylphenyl)ureido]phenylacetylamino}phenyl)-3-(4-methylpiperazin-1-yl)-propanoic acid;

3-(N-acetyl-N-methylamino)-3-(4-{4-[3-(2-methylphenyl)ureido]phenylacetyl-N-methylamino}-phenyl)-propionic acid;

3-benzyloxycarbonylamino-3-(4-{3-methoxy-4-[3-(2-methylphenyl)ureido]phenylacetylamino}-phenyl)-propanoic acid;

3-phenylsulphonylamino-3-(4-{3-methoxy-4-[3-(2-methylphenyl)ureido]phenylacetylamino}-phenyl)-propanoic acid;

3-(pyridine-3-carbonylamino)-3-(4-{3-methoxy-4-[3-(2-methylphenyl)ureido]phenylacetyl-amino}phenyl)-propanoic acid;

3-(pyridine-3-sulphonylamino)-3-(4-{3-methoxy-4-[3-(2-methylphenyl)ureido]phenylacetyl-amino}phenyl)-propanoic acid;

3-(5-dimethylamino-1-naphthalenesulphonylamino)-3-(4-{3-methoxy-4-[3-(2-methylphenyl)-ureido]phenylacetylamino}phenyl)-propanoic acid;

3-(4-carboxybutanoylamino)-3-(4-{3-methoxy-4-[3-(2-methylphenyl)ureido]phenylacetylamino}-phenyl)-propanoic acid;

3-(3-carboxypropanoylamino)-3-(4-{3-methoxy-4-[3-(2-methylphenyl)ureido]phenyl-acetylamino}phenyl)-propanoic acid;

3-(1-methylimidazol-4-ylsulphonylamino)-3-(4-{3-methoxy-4-[3-(2-methylphenyl)ureido]phenyl-acetylamino}phenyl)-propanoic acid;

3-(N-acetyl-methylamino)-3-(4-{3-methoxy-4-[3-(2-methylphenyl)ureido]phenylacetylamino}-phenyl)-propanoic acid;

3-(N-methanesulphonyl-methylamino)-3-(4-{3-methoxy-4-[3-(2-methylphenyl)ureido]phenyl-acetylamino}phenyl)-propanoic acid;

3-(morpholin-1-ylacetylamino)-3-(4-{3-methoxy-4-[3-(2-methylphenyl)ureido]phenyl-acetylamino}phenyl)-propanoic acid;

3-acetylamino-3-(4-{3-methylthio-4-[3-(2-methylphenyl)ureido]phenylacetylamino}phenyl)-propanoic acid;

3-acetylamino-3-(4-{3-methylsulphinyl-4-[3-(2-methylphenyl)ureido]phenylacetylamino}phenyl)-propanoic acid;

3-acetylamino-3-(4-{3-methylsulphonyl-4-[3-(2-methylphenyl)ureido]phenylacetylamino}-phenyl)-propanoic acid;

3-[2-(2-methoxyethoxy)acetylamino]-3-(4-{3-methoxy-4-[3-(2-methylphenyl)ureido]phenyl-acetylamino}phenyl)-propanoic acid;

3-[(tetrahydropyran-4-carbonyl)amino]-3-(4-{3-methoxy-4-[3-(2-methylphenyl)ureido]phenyl-acetylamino}phenyl)-propanoic acid;

3-[(5-methyl-isoxazole-3-carbonyl)amino]-3-(4-{3-methoxy-4-[3-(2-methylphenyl)ureido]phenyl-acetylamino}phenyl)-propanoic acid;
3-[(thiophene-2-carbonyl)-amino]-3-(4-{3-methoxy-4-[3-(2-methylphenyl)ureido]phenyl-acetylamino}phenyl)-propanoic acid;
3-[(4-carboxybenzoyl)-amino]-3-(4-{3-methoxy-4-[3-(2-methylphenyl)ureido]phenyl-acetylamino}phenyl)-propanoic acid;
3-[(pyridazin-3-carbonyl)-amino]-3-(4-{3-methoxy-4-[3-(2-methylphenyl)ureido]phenyl-acetylamino}phenyl)-propanoic acid;
3-[(3,4-dimethoxybenzoyl)-amino]-3-(4-{3-methoxy-4-[3-(2-methylphenyl)ureido]phenyl-acetylamino}phenyl)-propanoic acid;
3-[(pyridazin-3-carbonyl)-amino]-3-(4-{4-[3-(2-methylphenyl)ureido]phenylacetylamino}phenyl)-propanoic acid;
3-(4-carboxy-3,3-dimethyl-butanoylamino)-3-(4-{3-methoxy-4-[3-(2-methylphenyl)ureido]phenylacetylamino}-phenyl)-propanoic acid;
3-(benzoylamino)-3-(4-{4-[3-(2-methylphenyl)ureido]phenylacetylamino}phenyl)-propanoic acid;
3-(4-carboxybutanoylamino)-3-(4-{4-[3-(2-methylphenyl)ureido]phenylacetylamino}-phenyl)-propanoic acid;
3-[4-({3-methoxy-4-[3-(2-methylphenyl)ureido]-phenylacetyl}-N-methylamino)-phenyl]-butanoic acid;
3-[(4-carboxypyridine-3-carbonyl)-amino]-3-(4-{3-methoxy-4-[3-(2-methylphenyl)ureido]phenyl-acetylamino}phenyl)-propanoic acid;
3-[2,2-di-(hydroxymethyl)propanoyl-amino]-3-(4-{3-methoxy-4-[3-(2-methylphenyl)ureido]-phenylacetylamino}phenyl)-propanoic acid;
3-[2-(carboxymethyloxy)-acetylamino]-3-(4-{3-methoxy-4-[3-(2-methylphenyl)ureido]phenyl-acetylamino}phenyl)-propanoic acid;
3-[(1-carboxymethyl-piperidin-4-carbonyl)-amino]-3-(4-{3-methoxy-4-[3-(2-methylphenyl)ureido]phenylacetylamino}phenyl)-propanoic acid;
3-[2-(4-methyl-piperazin-1-yl)-acetylamino]-3-(4-{3-methoxy-4-[3-(2-methylphenyl)ureido]-phenylacetylamino}phenyl)-propanoic acid;
3-(pyrrolidin-1-yl)-3-[4-({4-[3-(2-methylphenyl)ureido]phenylacetyl}-methylamino)-phenyl]-propanoic acid;
3-(N-acetyl-methylamino)-3-[4-({4-[3-(2-methylphenyl)ureido]phenylacetyl}-methylamino)-phenyl]-propanoic acid;
3-(4-{3-methoxy-4-[3-(2-methylphenyl)ureido]phenylacetylamino}phenyl)-5-(4-methylpiperazin-1-yl)-5-oxo-pentanoic acid;
3-(4-{3-methoxy-4-[3-(2-methylphenyl)ureido]phenylacetylamino}phenyl)-5-(morpholin-4-yl)-5-oxo-pentanoic acid;
and the corresponding N-oxides, and their prodrugs; and pharmaceutically acceptable salts and solvates (e.g. hydrates) of such compounds and their N-oxides and prodrugs.

Preferred compounds of the invention include:

3-(5-{3-methoxy-4-[3-(2-methylphenyl)ureido]-phenylacetylamino}pyrid-2-yl)-propanoic acid;
3-(6-{3-methoxy-4-[3-(2-methylphenyl)ureido]-phenylacetylamino}pyrid-3-yl)-propanoic acid;
3-(4-{3-methoxy-4-[3-(2-methylphenyl)ureido]phenylacetylamino}phenyl)-3-(methanesulphonylamino)-propanoic acid;
3-(acetylamino)-3-(4-{3-methoxy-4-[3-(2-methylphenyl)ureido]phenylacetylamino}phenyl)-propanoic acid;
3-(benzoylamino)-3-(4-{3-methoxy-4-[3-(2-methylphenyl)ureido]phenylacetylamino}phenyl)-propanoic acid;
3-(4-{3-methoxy-4-[3-(2-methylphenyl)ureido]phenylacetylamino}phenyl)-3-(3-pyridylacetylamino)-propanoic acid;
3-amino-3-(4-{3-methoxy-4-[3-(2-methylphenyl)ureido]phenylacetylamino}phenyl)-propanoic acid;
3-(n-butylamino)-3-(4-{3-methoxy-4-[3-(2-methylphenyl)ureido]phenylacetylamino}phenyl)-propanoic acid;
3-benzylamino-3-(4-{3-methoxy-4-[3-(2-methylphenyl)ureido]phenylacetylamino}phenyl)-propanoic acid;
3-(4-{3-methoxy-4-[3-(2-methylphenyl)ureido]phenylacetylamino}phenyl)-3-(2-phenylethylamino)-propanoic acid;
3-(4-{3-methoxy-4-[3-(2-methylphenyl)ureido]phenylacetylamino}phenyl)-3-(morpholin-4-yl)-propanoic acid;
3-(4-{3-methoxy-4-[3-(2-methylphenyl)ureido]phenylacetylamino}phenyl)-3-(4-methylpiperazin-1-yl)-propanoic acid;
3-(N-acetyl-N-methylamino)-3-(4-{4-[3-(2-methylphenyl)ureido]phenylacetyl-N-methylamino}phenyl)-propionic acid;
3-benzyloxycarbonylamino-3-(4-{3-methoxy-4-[3-(2-methylphenyl)ureido]phenylacetylamino}-phenyl)propanoic acid;
3-phenylsulphonylamino-3-(4-{3-methoxy-4-[3-(2-methylphenyl)ureido]phenylacetylamino}-phenyl)-propanoic acid;
3-(pyridine-3-carbonylamino)-3-(4-{3-methoxy-4-[3-(2-methylphenyl)ureido]phenyl-acetylamino}phenyl)-propanoic acid;
3-(pyridine-3-sulphonylamino)-3-(4-{3-methoxy-4-[3-(2-methylphenyl)ureido]phenyl-acetylamino}phenyl)-propanoic acid;
3-(5-dimethylamino-1-naphthalenesulphonylamino)-3-(4-{3-methoxy-4-[3-(2-methylphenyl)ureido]phenylacetylamino}phenyl)-propanoic acid;
3-(4-carboxybutanoylamino)-3-(4-{3-methoxy-4-[3-(2-methylphenyl)ureido]phenylacetylamino}-phenyl)-propanoic acid;
3-(3-carboxypropanoylamino)-3-(4-{3-methoxy-4-[3-(2-methylphenyl)ureido]phenyl-acetylamino}phenyl)-propanoic acid;
3-(1-methylimidazol-4-ylsulphonylamino)-3-(4-{3-methoxy-4-[3-(2-methylphenyl)ureido]phenyl-acetylamino}phenyl)-propanoic acid;
3-(N-acetyl-methylamino)-3-(4-{3-methoxy-4-[3-(2-methylphenyl)ureido]phenylacetylamino}-phenyl)-propanoic acid;
3-(N-methanesulphonyl-methylamino)-3-(4-{3-methoxy-4-[3-(2-methylphenyl)ureido]phenyl-acetylamino}phenyl)-propanoic acid;
3-(morpholin-1-ylacetylamino)-3-(4-{3-methoxy-4-[3-(2-methylphenyl)ureido]phenyl-acetylamino}phenyl)-propanoic acid;
3-acetylamino-3-(4-{3-methylthio-4-[3-(2-methylphenyl)ureido]phenylacetylamino}phenyl)-propanoic acid
3-acetylamino-3-(4-{3-methylsulphinyl-4-[3-(2-methylphenyl)ureido]phenylacetylamino}phenyl)-propanoic acid;
3-acetylamino-3-(4-{3-methylsulphonyl-4-[3-(2-methylphenyl)ureido]phenylacetylamino}-phenyl)-propanoic acid;
3-[2-(2-methoxyethoxy)acetylamino]-3-(4-{3-methoxy-4-[3-(2-methylphenyl)ureido]acetylamino}phenyl)-propanoic acid;

3-[(tetrahydropyran-4-carbonyl)amino]-3-(4-{3-methoxy-4-[3-(2-methylphenyl)ureido]phenyl-acetylamino}phenyl)-propanoic acid;

3-[(5-methyl-isoxazole-3-carbonyl)-amino]-3-(4-{3-methoxy-4-[3-(2-methylphenyl)ureido]phenyl-acetylamino}phenyl)-propanoic acid;

3-[(thiophene-2-carbonyl)-amino]-3-(4-{3-methoxy-4-[3-(2-methylphenyl)ureido]phenyl-acetylamino}phenyl)-propanoic acid;

3-[(4-carboxybenzoyl)-amino]-3-(4-{3-methoxy-4-[3-(2-methylphenyl)ureido]phenyl-acetylamino}phenyl)-propanoic acid;

3-[(pyridazin-3-carbonyl)amino]-3-(4-{3-methoxy-4-[3-(2-methylphenyl)ureido]phenyl-acetylamino}phenyl)-propanoic acid;

3-[(3,4-dimethoxybenzoyl)-amino]-3-(4-{3-methoxy-4-[3-(2-methylphenyl)ureido]phenyl-acetylamino}phenyl)-propanoic acid;

3-[(pyridazin-3-carbonyl)-amino]-3-(4-{4-[3-(2-methylphenyl)ureido]phenylacetylamino}phenyl)-propanoic acid;

3-(4-carboxy-3,3-dimethyl-butanoylamino)-3-(4-{3-methoxy-4-[3-(2-methylphenyl)ureido]-phenylacetylamino}-phenyl)-propanoic acid;

3-(benzoylamino)-3-(4-{4-[3-(2-methylphenyl)ureido]phenylacetylamino}phenyl)-propanoic acid;

3-(4-carboxybutanoylamino)-3-(4-{4-[3-(2-methylphenyl)ureido]phenylacetylamino}-phenyl)-propanoic acid;

3-[4-({3-methoxy-4-[3-(2-methylphenyl)ureido]-phenylacetyl}-N-methylamino)-phenyl]-butanoic acid;

3-(4-{3-methoxy-4-[3-(2-methylphenyl)ureido]phenylacetylamino}phenyl)-5-(4-methylpiperazin-1-yl)-5-oxo-pentanoic acid;

3-(4-{3-methoxy-4-[3-(2-methylphenyl)ureido]phenylacetylamino}phenyl)-5-(morpholin-4-yl)-5-oxo-pentanoic acid;

and the corresponding N-oxides, and their prodrugs; and pharmaceutically acceptable salts and solvates (e.g. hydrates) of such compounds and their N-oxides and prodrugs.

Especially preferred compounds of the invention include:

(R)-3-acetylamino-3-(4-{3-methoxy-4-[3-(2-methylphenyl)ureido]phenyl-acetylamino}phenyl)-propanoic acid;

(R)-3-(4-carboxybutanoylamino)-3-(4-{3-methoxy-4-[3-(2-methylphenyl)ureido]phenyl-acetylamino}phenyl)-propanoic acid;

(R)-3-(3-carboxypropanoylamino)-3-(4-{3-methoxy-4-[3-(2-methylphenyl)ureido]phenyl-acetylamino}phenyl)-propanoic acid;

(R)-3-(pyridine-3-carbonylamino)-3-(4-{3-methoxy-4-[3-(2-methylphenyl)ureido]phenyl-acetylamino}phenyl)-propanoic acid;

(R)-3-benzoylamino-3-(4-{3-methoxy-4-[3-(2-methylphenyl)ureido]phenylacetylamino}phenyl)-propanoic acid;

(R)-3-[2-(2-methoxyethoxy)acetylamino]-3-(4-{3-methoxy-4-[3-(2-methylphenyl)ureido]phenyl-acetylamino}phenyl)-propanoic acid;

(R)-3-[(tetrahydropyran-4-carbonyl)amino]-3-(4-{3-methoxy-4-[3-(2-methylphenyl)ureido]-phenylacetylamino}phenyl)-propanoic acid;

(R)-3-[(5-methyl-isoxazole-3-carbonyl)-amino]-3-(4-{3-methoxy-4-[3-(2-methylphenyl)ureido]-phenylacetylamino}phenyl)-propanoic acid;

(R)-3-[(thiophene-2-carbonyl)-amino]-3-(4-{3-methoxy-4-[3-(2-methylphenyl)ureido]phenyl-acetylamino}phenyl)-propanoic acid;

(R)-3-[(4-carboxybenzoyl)-amino]-3-(4-{3-methoxy-4-[3-(2-methylphenyl)ureido]phenyl-acetylamino}phenyl)-propanoic acid;

(R)-3-[(pyridazin-3-carbonyl)-amino]-3-(4-{3-methoxy-4-[3-(2-methylphenyl)ureido]phenyl-acetylamino}phenyl)-propanoic acid;

(R)-3-[(3,4-dimethoxybenzoyl)-amino]-3-(4-{3-methoxy-4-[3-(2-methylphenyl)ureido]phenyl-acetylamino}phenyl)-propanoic acid;

(R)-3-[(pyridazin-3-carbonyl)-amino]-3-(4-{4-[3-(2-methylphenyl)ureido]phenylacetylamino}-phenyl)-propanoic acid;

(R)-3-(4-carboxy-3,3-dimethyl-butanoylamino)-3-(4-{3-methoxy-4-[3-(2-methylphenyl)ureido]-phenylacetylamino}-phenyl)-propanoic acid;

(R)-3-(benzoylamino)-3-(4-{4-[3-(2-methylphenyl)ureido]phenylacetylamino}phenyl)-propanoic acid;

(R)-3-(4-carboxybutanoylamino)-3-(4-{4-[3-(2-methylphenyl)ureido]phenylacetylamino}-phenyl)-propanoic acid;

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4 \beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 4 \beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 (α4β1), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 (α4β1), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, may be prepared by hydrolysis of esters of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is a —$CO_2R^{16}$ group (in which $R^{16}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, may be prepared by acid catalysed removal of the tert-butyl group of tert-butyl esters of formula (I), wherein $R^1$, $X^1$, $X^2$, $X^3$, $X^4$, $X^5$ and $X^6$ are as hereinbefore defined; and where the Y moiety within one of $X^3$, $X^4$ and $X^5$ is a —$CO_2R^{16}$ group (in which $R^{16}$ is tert-butyl), using standard reaction conditions, for example reaction with trifluoroacetic acid at a temperature at about room temperature.

As another example compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, may be prepared by hydrogenation of compounds of formula (I) wherein $R^1$, $X^1$, $X^2$, $X^3$, $X^4$, $X^5$ and $X^6$ are as hereinbefore defined, and where the Y moiety within one of $X^3$, $X^4$ and $X^5$ is a —$CO_2R^{16}$ group (in which $R^{16}$ is benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol. This reaction is most suitable for compounds of formula (I) where $L^1$ and $L^2$ do not contain carbon-carbon multiple bonds.

As another example compounds of formula (Ia) or (Ib), wherein $R^1$, $R^2$, $Ar^1$, $L^2$, $X^1$ and $X^2$ are as hereinbefore defined, $X^3$ is $CR^{10}$ (where $R^{10}$ is as hereinbefore defined), and Y is carboxy, represented by formula (II), may be prepared by using resin technology as shown in scheme 1.

SCHEME 1

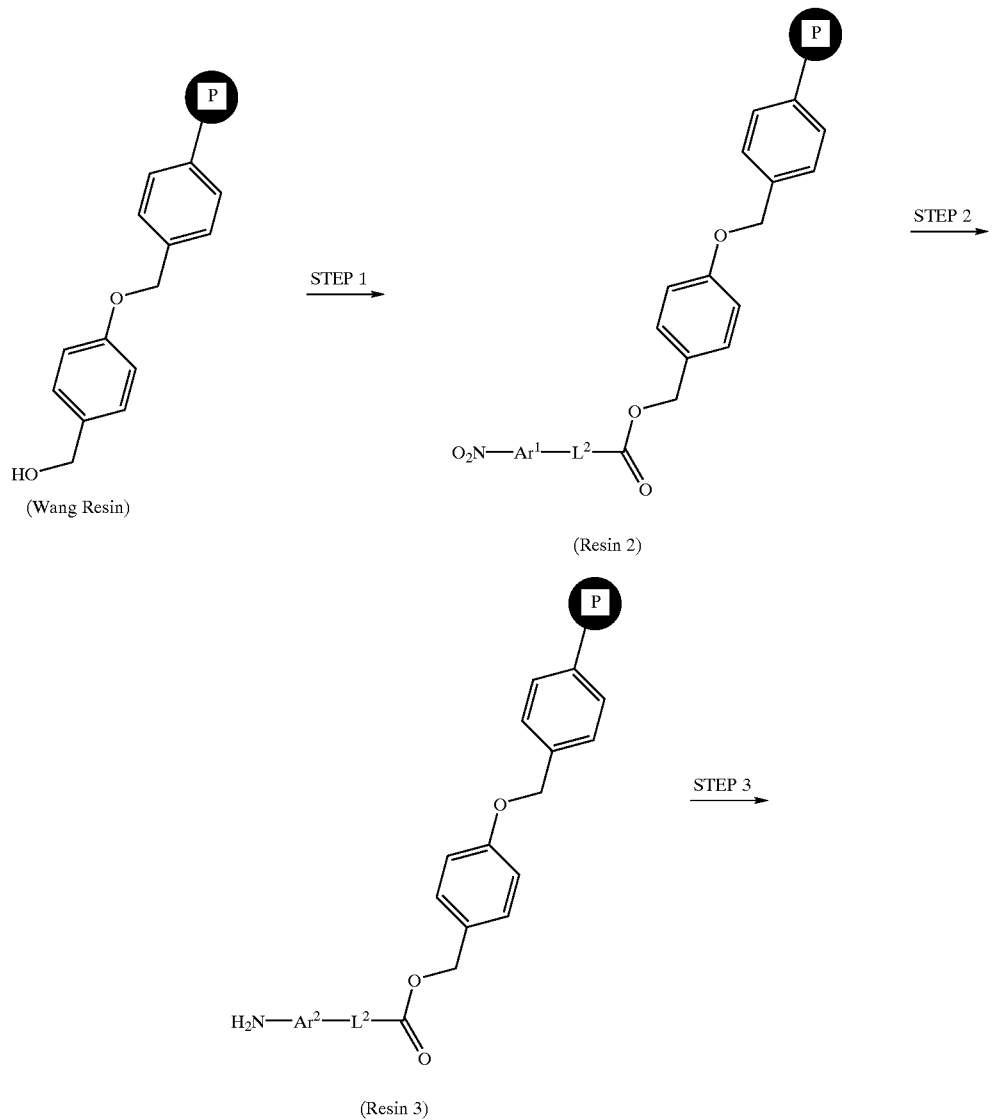

-continued

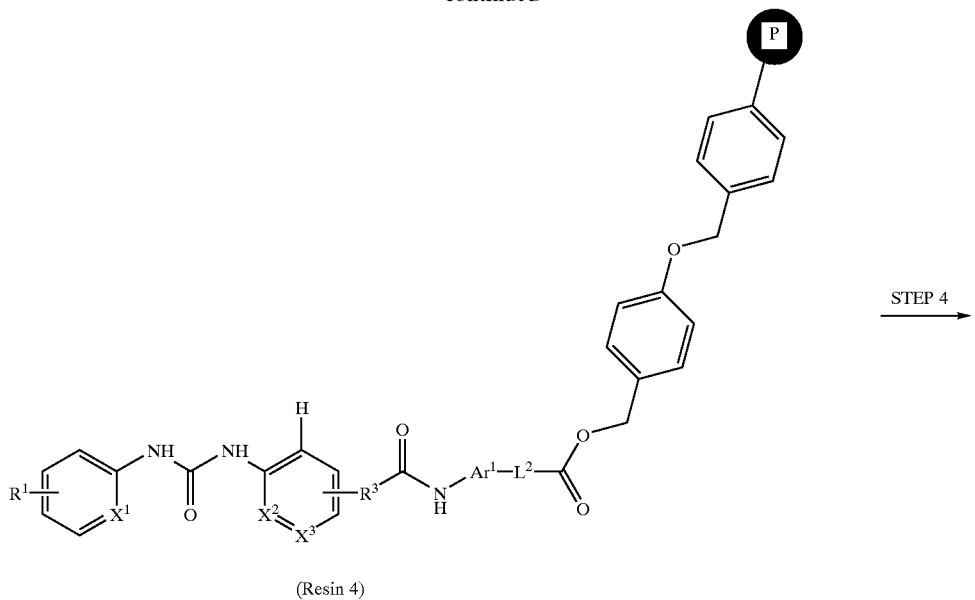

(Resin 4)

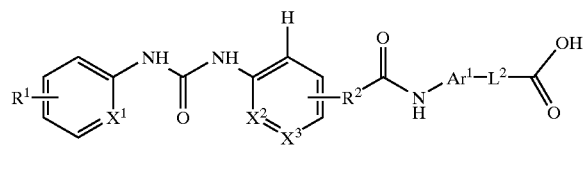

(II)

For example Wang resin may be treated, in Step 1, with acids of formula (III):

wherein $Ar^1$ and $L^2$ are as hereinbefore defined, with diisopropyl carbodiimide in dimethylformamide, in the presence of dimethylaminopyridine, at room temperature. The resulting esters (Resin 2), wherein $Ar^1$ and $L^2$ are as hereinbefore defined, may then treated, in Step 2, with tin chloride in dimethylformamide at room temperature to give Resin 3, wherein $Ar^1$ and $L^2$ are as hereinbefore defined. Resin 3 may then be coupled, in Step 3, with an acid of general formula (IV):

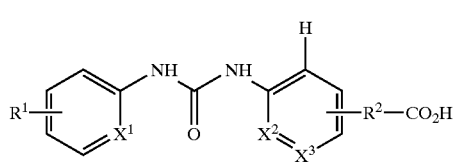

wherein $R^1$, $R^2$, $X^1$ and $X^2$ are as hereinbefore, and $X^3$ is $CR^{10}$ (where $R^{10}$ is as hereinbefore defined), in the presence of O-(7-azabenzotriazol-1-yl)-1,1,3,3-tetramethyluronium hexafluorophosphate and diisopropylethylamine in dimethylformamide, at room temperature. The resulting Resin 4, wherein $R^1$, $R^2$, $Ar^1$, $L^2$, $X^1$ and $X^2$ are as hereinbefore defined , and $X^3$ is $CR^{10}$ (where $R^{10}$ is as hereinbefore defined), may then be treated, in Step 4, with trifluoroacetic acid in an inert solvent such as dichloromethane, at room temperature, to liberate the acids of general formula (II), wherein $R^1$, $R^2$, $Ar^1$, $L^2$, $X^1$ and $X^2$ are as hereinbefore defined, and $X^3$ is $CR^{10}$ (where $R^{10}$ is as hereinbefore defined).

As another example compounds of formula (Ib), wherein $R^1$, $R^2$, $Ar^1$, $X^1$ and $X^2$ are as hereinbefore defined, $L^2$ is a —$Z^2$—$R^9$— linkage [in which $R^9$ is as hereinbefore defined and $Z^2$ is O, S or $NR^4$ (where $R^4$ is as defined hereinbefore)], $X^3$ is $CR^{10}$ (where $R^{10}$ is as hereinbefore defined), and Y is carboxy, represented by formula (V), may be prepared by using resin technology as shown in scheme 2.

SCHEME 2
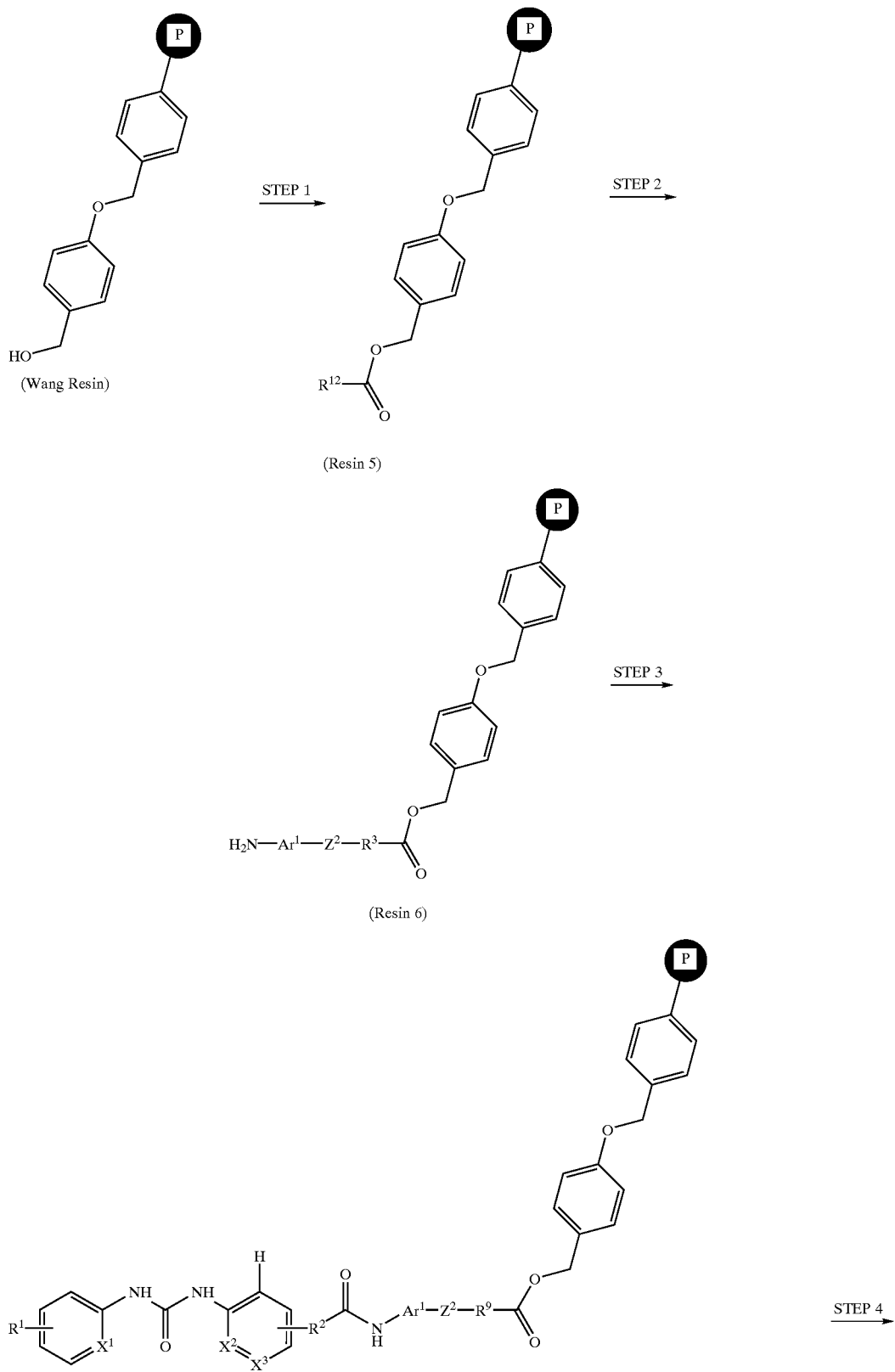

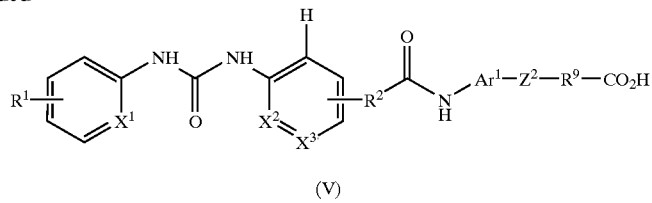

(V)

For example Wang resin in scheme 2 may be treated, in Step 1, with acids of formula (VI):

$$R^{17}-CO_2H \quad (VI)$$

wherein $R^{17}$ is $Br-R^9-$ [in which $R^9$ is as hereinbefore defined], with diisopropyl carbodiimide in dimethylformamide or a mixture of dimethylformamide and tetrahydrofuran, in the presence of dimethylaminopyridine, at room temperature. The resulting esters (Resin 5, in which $R^{17}$ is $Br-R^9-$) may be reacted, in Step 2, with compounds of formula (VII):

$$H_2N-Ar^1-Z^2H \quad (VII)$$

wherein $Ar^1$ is heteroaryldiyl and $Z^2$ is O, S or $NR^4$ (where $R^4$ is as defined hereinbefore), in the presence of a base, such as a tertiary organic base, for example diisopropylethylamine, in dimethylsulphoxide and at a temperature at about room temperature, to give Resin 6, in which $R^9$ and $Ar^1$ is heteroaryldiyl and $Z^2$ is O, S or $NR^4$ (where $R^4$ is as defined hereinbefore). Resin 6 may then be coupled, in Step 3, with an acid of general formula (IV), wherein $R^1$, $R^2$, $X^1$ and $X^2$ are as hereinbefore defined, and $X^3$ is $CR^{10}$ (where $R^{10}$ is as hereinbefore defined), in the presence of O-(7-azabenzotriazol-1-yl)-1,1,3,3-tetramethyluronium hexafluorophosphate and diisopropylethylamine in dimethylformamide, at room temperature. The resulting Resin 7 [in which $R^1$, $R^2$, $R^9$, $X^1$ and $X^2$ are as hereinbefore defined, $Ar^1$ is heteroaryldiyl, $X^3$ is $CR^{10}$ (where $R^{10}$ is as hereinbefore defined), and $Z^2$ is O, S or $NR^4$ (where $R^4$ is as defined hereinbefore)], may then be treated, in Step 4, with trifluoroacetic acid in an inert solvent such as dichloromethane and at a temperature at about room temperature, to liberate the acids of general formula (V), wherein $R^1$, $R^2$, $R^9$, $X^1$ and $X^2$ are as hereinbefore defined, $Ar^1$ is heteroaryldiyl, $X^3$ is $CR^{10}$ (where $R^{10}$ is as hereinbefore defined), and $Z^2$ is O, S or $NR^4$ (where $R^4$ is as defined hereinbefore). This methodology is particularly suited to the preparation of compounds of formula (V) where $L^2$ is a $-S-CH_2-$ linkage.

As another example, Wang resin in scheme 2 may be treated, in Step 1, with acid chlorides of formula (VIII):

$$R^{17}-C(=O)-Cl \quad (VIII)$$

wherein $R^{17}$ is a vinyl moiety optionally substituted by $R^5$, in the presence of a tertiary amine, such as diisopropylethylamine, in an inert solvent, such as dichloromethane, at a temperature at about room temperature. The resulting optionally substituted vinyl ester (Resin 5, in which $R^{17}$ is a vinyl moiety optionally substituted by $R^5$), may then be reacted with compounds of formula (VII), wherein $Ar^1$ is heteroaryldiyl and $Z^2$ is S, in the presence of a base, such as a tertiary organic base, for example diisopropylethylamine, in dimethylsulphoxide and at a temperature at about room temperature, to give Resin 6 [in which $Ar^1$ is heteroaryldiyl, $R^9$ is ethylene (optionally substituted by $R^5$) and $Z^2$ is S]. Resin 6 may then be coupled with an acid of general formula (IV), wherein $R^1$, $R^2$, $X^1$ and $X^2$ are as hereinbefore defined, and $X^3$ is $CR^{10}$ (where $R^{10}$ is as hereinbefore defined), in the presence of O-(7-azabenzotriazol-1-yl)-1,1,3,3-tetramethyluronium hexafluorophosphate and diisopropylethylamine in dimethylformamide, at room temperature. The resulting Resin 7 [in which $R^1$, $R^2$, $X^1$ and $X^2$ are as defined hereinbefore, $Ar^1$ is heteroaryldiyl, $R^9$ is ethylene (optionally substituted by $R^5$), $X^3$ is $CR^{10}$ (where $R^{10}$ is as hereinbefore defined), and $Z^2$ is S], may then be treated with trifluoroacetic acid in an inert solvent such as dichloromethane and at a temperature at about room temperature, to liberate the acids of general formula (V), wherein $R^1$, $R^2$, $X^1$ and $X^2$ are as defined hereinbefore, $Ar^1$ is heteroaryldiyl, $R^9$ is ethylene (optionally substituted by $R^5$), $X^3$ is $CR^{10}$ (where $R^{10}$ is as hereinbefore defined), and $Z^2$ is S.

As another example compounds of formula (Ia) or (Ib), wherein $R^1$, $R^2$, $L^2$, $Ar^1$, $X^1$ and $X^2$ are as hereinbefore defined, and $X^3$ is $CR^{10}$ (where $R^{10}$ is as hereinbefore defined), and Y is carboxy, may be prepared by coupling acids of formula (IV), wherein $R^1$, $R^2$, $X^1$ and $X^2$ are as hereinbefore, and $X^3$ is $CR^{10}$ (where $R^{10}$ is as hereinbefore defined), with amines of formula (IX):

$$H_2N-Ar^1-L^2-CO_2H \quad (IX)$$

wherein $Ar^1$ and $L^2$ are as hereinbefore defined, using standard coupling conditions, for example those hereinbefore described.

As another example compounds of formula (I), wherein $R^1$, $X^1$, $X^2$, $X^3$, $X^4$, $X^5$ and $X^6$ are as hereinbefore defined and where the $L^2$ and Y moieties within one of $X^3$, $X^4$ and $X^5$ are an alkylene linkage substituted by $-CONY^1Y^2$ and carboxy respectively, may be prepared by reaction of compounds of formula (I), wherein $R^1$, $X^1$, $X^2$, $X^3$, $X^4$, $X^5$ and $X^6$ are as hereinbefore defined and where the $L^2$ and Y moieties within one of $X^3$, $X^4$ and $X^5$ are an alkylene linkage substituted by $-CO_2H$ and carboxy respectively, with an anhydride, such as trifluoroacetic anhydride, in an inert solvent e.g. tetrahydrofuran, followed by treatment with an amine $HNY^1Y^2$.

According to a further feature of the present invention, compounds of the invention may be prepared by interconversion of other compounds of the invention.

For example compounds of formula (I) wherein $R^1$, $X^1$, $X^2$, $X^3$, $X^4$, $X^5$ and $X^6$ are as hereinbefore defined, and where the Y moiety within one of $X^3$, $X^4$ and $X^5$ is $-C(=O)-NHOH$, may be prepared by reaction of compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl) hydroxylamine, O-(t-butyldimethylsilyl)-hydroxylamine, or O-(tetrahydropyranyl)hydroxylamine followed by treatment with acid.

As another example of the interconversion process, compounds of formula (I) containing sulphoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH5, at temperatures between about 0° C. and room temperature. This latter method is preferred for compounds containing an acid-labile group.

As another example of the interconversion process, compounds of formula (I) containing sulphone linkages may be prepared by the oxidation of corresponding compounds containing —S— or sulphoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I), wherein $R^1$, $X^1$, $X^2$, $X^3$, $X^4$, $X^5$ and $X^6$ are as hereinbefore described and the $L^2$ moiety within one of $X^3$, $X^4$ and $X^5$ is an optionally substituted alkylene linkage, may be prepared by hydrogenation of the corresponding compounds of formula (I) in which the $L^2$ moiety within one of $X^3$, $X^4$ and $X^5$ is the corresponding optionally substituted alkenylene linkage. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I), wherein $R^1$, $X^1$, $X^2$, $X^3$, $X^4$, $X^5$ and $X^6$ are as hereinbefore described and the $L^1$ moiety within one of $X^3$, $X^4$ and $X^5$ is a —$R^2$—$R^3$— linkage where $R^2$ is a straight or branched chain $C_{2-6}$alkylene chain and $R^3$ is a direct bond, may be similarly prepared by hydrogenation of the corresponding compounds of formula (I) in which the $L^1$ moiety within one of $X^3$, $X^4$ and $X^5$ is a —$R^2$—$R^3$ linkage where $R^2$ is a straight or branched chain $C_{2-6}$alkenylene chain and $R^3$ is a direct bond.

As another example of the interconversion process, compounds of formula (I), wherein $R^1$, $X^1$, $X^2$, $X^3$, $X^4$, $X^5$ and $X^6$ are as hereinbefore described, and where the $L^2$ moiety within one of $X^3$, $X^4$ and $X^5$ contains an amino group, may be prepared by treatment of compounds of formula (I), wherein $R^1$, $X^1$, $X^2$, $X^3$, $X^4$, $X^5$ and $X^6$ are as hereinbefore described, and the $L^2$ moiety within one of $X^3$, $X^4$ and $X^5$ contains an acetamido group, with a base, such as an aqueous alkali metal hydroxide, for example sodium hydroxide.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $—R^2—R^3—$ linkage (in which $R^2$ is as hereinbefore defined and $R^3$ is $—C(=O)—NH—$) and a $—CO_2R^{16}$ group (in which $R^{16}$ is as hereinbefore defined) respectively, may be prepared by reaction of compounds of formula (1):

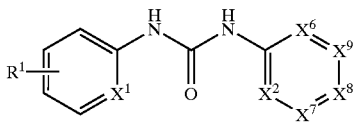

(1)

wherein $R^1$, $X^1$, $X^2$ and $X^6$ are as hereinbefore defined, one of $X^7$, $X^8$ and $X^9$ represents $C—R^{18}$ [in which $R^{18}$ is $—R^2—C(=O)X^{10}$ (where $R^2$ is as hereinbefore defined and $X^{10}$ is a hydroxy group, or a halogen, preferably chlorine, atom)] and the others independently represent N or $CR^{10}$ (where $R^{10}$ is as hereinbefore defined), with amines of formula (2):

(2)

wherein $R^4$, $R^{16}$, $Ar^1$ and $L^2$ are as hereinbefore defined. When $X^{10}$ is a hydroxy group the reaction may be carried out using standard peptide coupling procedures as described hereinbefore. When $X^{10}$ is a halogen atom the reaction may be carried out with the aid of a base, such pyridine, preferably in a solvent such as tetrahydrofuran and at a temperature at about room temperature.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $—R^2—R^3—$ linkage [in which $R^2$ is as hereinbefore defined and $R^3$ is $—NR^4—C(=O)—$ (where $R^4$ is as hereinbefore defined)] and a $—CO_2R^{16}$ group (in which $R^{16}$ is as hereinbefore defined) respectively, may be prepared by reaction of compounds of formula (1), wherein $R^1$, $X^1$, $X^2$ and $X^6$ are as hereinbefore defined, one of $X^7$, $X^8$ and $X^9$ represents $C—R^{18}$ [in which $R^{18}$ is $—R^2—NHR^4$ (where $R^2$ and $R^4$ are as hereinbefore defined)] and the others independently represent N or $CR^{10}$ (where $R^{10}$ is as hereinbefore defined), with compounds of formula (3):

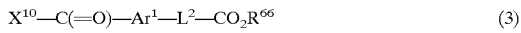

(3)

wherein $R^{16}$, $Ar^1$, $L^2$ and $X^{10}$ are as hereinbefore defined, using procedures described hereinbefore for coupling acids or acid halides with amines.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ groups are a $—R^2—R^3—$ linkage [in which $R^2$ is as hereinbefore defined and $R^3$ is $—O—$] and a $—CO_2R^{16}$ group (in which $R^{16}$ is as hereinbefore defined) respectively, may be prepared by reaction of compounds of formula (1), wherein $R^1$, $X^1$, $X^2$ and $X^6$ are as hereinbefore defined, one of $X^7$, $X^8$ and $X^9$ represents $C—R^{18}$ (in which $R^{18}$ is $—R^2—OH$) and the others independently represent N or $CR^{10}$ (where $R^{10}$ is as hereinbefore defined), with compounds of (4):

(4)

wherein $R^{16}$, $Ar^1$ and $L^2$ are as hereinbefore defined, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

Alternatively esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $—R^2—R^3—$ linkage [in which $R^2$ is as hereinbefore defined and $R^3$ is $—O—$] and a $—CO_2R^{16}$ group (in which $R^{16}$ is as hereinbefore defined) respectively, may also be prepared by alkylation of compounds of formula (4), wherein $R^{16}$, $Ar^1$ and $L^2$ are as hereinbefore defined. The reaction may be carried using standard alkylation conditions for example reaction with the appropriate alkyl bromides of formula (1), wherein $R^1$, $X^1$, $X^2$ and $X^6$ are as hereinbefore defined, one of $X^7$, $X^8$ and $X^9$ represents $C—R^{18}$ [in which $R^{18}$ is $—R^2—Br$ (where $R^2$ is as hereinbefore defined)], and the others independently represent N or $CR^{10}$ (where $R^{10}$ is as hereinbefore defined).

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $—R^2—R^3—$ linkage [in which $R^2$ is as hereinbefore defined and $R^3$ is $—S—$] and a $—CO_2R^{16}$ group (in which $R^{16}$ is as hereinbefore defined) respectively, may be similarly prepared by alkylation of compounds of formula (5):

(5)

wherein $R^{16}$, $Ar^1$ and $L^2$ are as hereinbefore defined.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $—R^2—R^3—$ linkage [in which $R^2$ is as hereinbefore defined and $R^3$ is $—NR^4—$ (where $R^4$ is as hereinbefore defined)] and a $—CO_2R^{16}$ group (in which $R^{16}$ is as hereinbefore defined) respectively, may be similarly prepared by alkylation of compounds of formula (2), wherein $R^4$, $R^{16}$, $Ar^1$ and $L^2$ are as hereinbefore defined.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $—R^2—R^3—$ linkage [in which $R^2$ is as hereinbefore defined and $R^3$ is $—C(=O)—$] and a $—CO_2R^{16}$ group (where $R^{16}$ is as hereinbefore defined) respectively, may be prepared by reaction of compounds of formula (1), wherein $R^1$, $X^1$, $X^2$ and $X^6$ are as hereinbefore defined, one of $X^7$, $X^8$ and $X^9$ represents $C—R^{18}$ [in which $R^{18}$ is $—R^2—CO_2R^{16}$ (where $R^2$ and $R^{16}$ are as hereinbefore defined)], and the others independently represent N or $CR^{10}$ (where $R^{10}$ is as hereinbefore defined), with Grignard reagents derived from reaction of compounds of formula (6):

(6)

wherein $R^{16}$, $Ar^1$ and $L^2$ are as hereinbefore defined, with magnesium using standard reaction conditions.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $—R^2—R^3—$ linkage [in which $R^2$ is as hereinbefore defined and $R^3$ is $—NR^4—C(=O)—NH—$ (where $R^4$ is as hereinbefore defined)] and a $—CO_2R^{16}$ group (where $R^{16}$ is as hereinbefore defined) respectively, may be prepared by reaction of compounds of formula (1), wherein $R^1$, $X^1$, $X^2$ and $X^6$ are as hereinbefore defined, one of $X^7$, $X^8$ and $X^9$ represents $C—R^{18}$ [in which $R^{18}$ is $—R^2—NHR^4$ (where $R^2$ and $R^4$ are as hereinbefore defined)],), and the others independently represent N or $CR^{10}$ (where $R^{10}$ is as hereinbefore defined), with isocyanates of formula (7):

$$O=C=N-Ar^1-L^2-CO_2R^{16} \quad (7)$$

wherein $R^{16}$, $Ar^1$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $-R^2-R^3-$ linkage [in which $R^2$ is as hereinbefore defined and $R^3$ is $-NH-C(=O)-NR^4-$ (where $R^4$ is as hereinbefore defined)] and a $-CO_2R^{16}$ group (where $R^{16}$ is as hereinbefore defined) respectively, may be similarly prepared by reaction of amines of formula (2), wherein $R^4$, $R^{16}$, $Ar^1$ and $L^2$ are as hereinbefore defined, with compounds of formula (1), wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-N=C=O$ (where $R^2$ is as hereinbefore defined)], and the others independently represent N or $CR^{10}$ (where $R^{10}$ is as hereinbefore defined).

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $-R^2-R^3-$ linkage [in which $R^2$ is as hereinbefore defined and $R^3$ is $-SO_2-NR^4-$ (where $R^4$ is as hereinbefore defined)] and a $-CO_2R^{16}$ group (where $R^{16}$ is as hereinbefore defined) respectively, may be prepared by reaction of compounds of formula (1), wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-SO_2Cl$ (where $R^2$ is as hereinbefore defined), and the others independently represent N or $CR^{10}$ (where $R^{10}$ is as hereinbefore defined), with amines of formula (2) wherein $R^4$, $R^{16}$, $Ar^1$ and $L^2$ are as hereinbefore defined. The reaction is preferably carried out with the aid of a base, such as a tertiary amine, for example triethylamine, preferably in a solvent such as tetrahydrofuran and at a temperature at about room temperature.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $-R^2-R^3-$ linkage [in which $R^2$ is as hereinbefore defined and $R^3$ is $-NR^4-SO_2-$ (where $R^4$ is as hereinbefore defined)] and a $-CO_2R^{16}$ group (where $R^{16}$ is as hereinbefore defined) respectively, may be similarly prepared by reaction of compounds of formula (1), wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-NHR^4$ (where $R^2$ and $R^4$ are as hereinbefore defined)], and the others independently represent N or $CR^{10}$ (where $R^{10}$ is as hereinbefore defined), with sulphonyl chlorides of formula (8):

$$Cl-SO_2-Ar^1-L^2-CO_2R^{16} \quad (8)$$

wherein $R^{16}$, $Ar^1$ and $L^2$ are as hereinbefore defined.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $-R^2-R^3-$ linkage [in which $R^2$ is as hereinbefore defined and $R^3$ is $-O-C(=O)-$] and a $-CO_2R^{16}$ group (where $R^{16}$ is as hereinbefore defined) respectively, may be prepared by O-acylation of compounds of formula (1), wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-OH$ (where $R^2$ is as hereinbefore defined)], and the others independently represent N or $CR^{10}$ (where $R^{10}$ is as hereinbefore defined), with compounds of formula (3), wherein $R^{16}$, $Ar^1$ and $L^2$ are as hereinbefore defined and $X^{10}$ is a halogen atom. The reaction may be carried using standard O-acylation conditions for example reaction with acid chlorides of formula (3) where $X^{10}$ is a chlorine atom.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $-R^2-R^3-$ linkage [in which $R^2$ is as hereinbefore defined and $R^3$ is $-C(=O)-O-$] and a $-CO_2R^{16}$ group (where $R^{16}$ is as hereinbefore defined) respectively, may be similarly prepared by O-acylation of compounds of formula (4), wherein $R^{16}$, $Ar^1$ and $L^2$ are as hereinbefore defined with compounds of formula (1), wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-C(=O)-X^{10}$ (where $R^2$ is as hereinbefore defined and $X^{10}$ is a halogen atom)], and the others independently represent N or $CR^{10}$ (where $R^{10}$ is as hereinbefore defined).

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $-R^2-R^3-$ linkage [in which $R^2$ is as hereinbefore defined and $R^3$ is $-O-C(=O)-NH-$] and a $-CO_2R^{16}$ group (where $R^{16}$ is as hereinbefore defined) respectively, may be prepared by reaction of compounds of formula (1), wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-OH$ (where $R^2$ is as hereinbefore defined)], and the others independently represent N or $CR^{10}$ (where $R^{10}$ is as hereinbefore defined), with isocyanates of formula (7), wherein $R^{16}$, $Ar^1$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I), wherein $R^1$, $X^1$, $X^2$, $X^3$, $X^4$, $X^5$ and $X^6$ are as hereinbefore defined and where the $L^1$ and Y moieties within one of $X^3$, $X^4$ and $X^5$ are a $-R^2-R^3-$ linkage [in which $R^2$ is as hereinbefore defined and $R^3$ is $-NH-C(=O)-O-$] and a $-CO_2R^{16}$ group (where $R^{16}$ is as hereinbefore defined) respectively, may be similarly prepared by reaction of compounds of formula (1), wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-N=C=O$ (where $R^2$ is as hereinbefore defined)], and the others independently represent N or $CR^{10}$ (where $R^{10}$ is as hereinbefore defined), with compounds of formula (4), wherein $R^{16}$, $Ar^1$ and $L^2$ are as hereinbefore defined.

Esters of formula (I), wherein $R^1$, $X^1$, $X^2$, $X^3$, $X^4$, $X^5$ and $X^6$ are as hereinbefore defined and where one of $X^3$, $X^4$ and $X^5$ is $C-R^2-R^3-Ar^1-L^2-CO_2R^{16}$ in which $R^3$ is a direct bond, $R^2$ is a straight or branched chain $C_{2-6}$alkenylene chain where the carbon-carbon double bond is directly attached to $Ar^1$, and $R^{16}$ is as hereinbefore defined, may be prepared from compounds of formula (9):

$$H-C(=O)-Ar^1-L^2-CO_2R^{16} \quad (9)$$

wherein $R^{16}$, $Ar^1$ and $L^2$ are as hereinbefore defined, using standard Wittig coupling procedures with an appropriate phosphorane, derived from reaction of the appropriate compounds of formula (1) wherein $R^1$, $X^1$, $X^2$ and $X^6$ are as hereinbefore defined, one of $X^7$, $X^8$ and $X^9$ represents $C-R^{18}$ [in which $R^{18}$ is $-R^2-Br$ (where $R^2$ is a straight or branched chain $C_{1-5}$alkylene chain)], and the others independently represent N or $CR^{10}$ (where $R^{10}$ is as hereinbefore defined), with triphenylphosphine and subsequent treatment with a base using standard procedures.

Esters of formula (I), wherein $R^1$, $X^1$, $X^2$, $X^3$, $X^4$, $X^5$ and $X^6$ are as hereinbefore defined, Y is $-CO_2R^{16}$ and the $L^2$ moiety within one of $X^3$, $X^4$ and $X^5$ is an alkylene linkage substituted by $-NY^1Y^2$ (in which one of $Y^1$ and $Y^2$ is hydrogen and the other is alkyl, or alkyl substituted by alkoxy, aryl, cyano, cycloalkyl, heteroaryl, heterocycloalkyl, hydroxy, oxo, $-NY^1Y^2$, or one or more $-CO_2R^{12}$ or $-C(=O)-NY^1Y^2$ groups), may be prepared by reaction of esters of formula (I), wherein $R^1$, $X^1$, $X^2$, $X^3$, $X^4$, $X^5$ and $X^6$ are as hereinbefore defined, Y is $-CO_2R^{16}$, and the $L^2$ moiety within one of $X^3$, $X^4$ and $X^5$ is an alkylene linkage substituted by $-NH_2$, with aldehydes of formula (10):

$$R^{19}-CHO \qquad (10)$$

wherein $R^{19}$ is hydrogen or alkyl, or alkyl substituted by alkoxy, aryl, cyano, cycloalkyl, heteroaryl, heterocycloalkyl, hydroxy, oxo, $-NY^1Y^2$, or one or more $-CO_2R^{12}$ or $-C(=O)-NY^1Y^2$ groups in the presence of sodium cyanoborohydride. The reaction may be conveniently carried out in methanol, optionally in the presence of sodium acetate and 4 Å molecular sieves, and at a temperature at about room temperature.

Esters of formula (1), wherein $R^1$, $X^1$, $X^2$, $X^3$, $X^4$, $X^5$ and $X^6$ are as hereinbefore defined, Y is $-CO_2R^{16}$ and the $L^2$ moiety within one of $X^3$, $X^4$ and $X^5$ contains a $-N(R^4)-C(=O)-R^{13}$ group, may be prepared by reaction of amines of formula (I), wherein $R^1$, $X^1$, $X^2$, $X^3$, $X^4$, $X^5$ and $X^6$ are as hereinbefore defined, Y is $-CO_2R^{16}$ and the $L^2$ moiety within one of $X^3$, $X^4$ and $X^5$ contains a $-NH(R^4)$ group, with compounds of formula (11):

$$R^{13}-C(=O)X^{10} \qquad (11)$$

wherein $R^{13}$ and $X^{10}$ are as hereinbefore defined. When $X^{10}$ is a hydroxy group the reaction may be carried out using standard peptide coupling procedures as described hereinbefore. When $X^{10}$ is a halogen atom the reaction may be carried out with the aid of a base, such pyridine, preferably in a solvent such as tetrahydrofuran and at a temperature at about room temperature.

Esters of formula (I), wherein $R^1$, $X^1$, $X^2$, $X^3$, $X^4$, $X^5$ and $X^6$ are as hereinbefore defined Y is $-CO_2R^{16}$ and the $L^2$ moiety within one of $X^3$, $X^4$ and $X^5$ contains a $-N(R^4)-C(=O)-OR^{13}$ group may be prepared by reaction of amines of formula (I), wherein $R^1$, $X^1$, $X^2$, $X^3$, $X^4$, $X^5$ and $X^6$ are as hereinbefore defined, Y is $-CO_2R^{16}$ and the $L^2$ moiety within one of $X^3$, $X^4$ and $X^5$ contains a $-NH(R^4)$ group, with the appropriate chloroformate, e.g. ethyl (or benzyl) chloroformate compounds, according to standard reaction conditions.

Esters of formula (I), wherein $R^1$, $X^1$, $X^2$, $X^3$, $X^4$, $X^5$ and $X^6$ are as hereinbefore defined Y is $-CO_2R^{16}$ and the $L^2$ moiety within one of $X^3$, $X^4$ and $X^5$ contains a $-N(R^4)-SO_2-R^{13}$ group, may be prepared by reaction of amines of formula (I), wherein $R^1$, $X^1$, $X^2$, $X^3$, $X^4$, $X^5$ and $X^6$ are as hereinbefore defined, Y is $-CO_2R^{16}$ and the $L^2$ moiety within one of $X^3$, $X^4$ and $X^5$ contains a $-NH(R^4)$ group,, with the appropriate sulphonyl chloride, e.g. phenyl (or pyrdiyl) sulphonyl chloride, according to standard reaction conditions.

Esters of formula (I), wherein $R^1$, $X^1$, $X^2$, $X^3$, $X^4$, $X^5$ and $X^6$ are as hereinbefore defined Y is $-CO_2R^{16}$ and the $L^2$ moiety within one of $X^3$, $X^4$ and $X^5$ is a

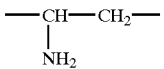

linkage, may be prepared by hydrogenation of esters of formula (I), wherein $R^1$, $X^1$, $X^2$, $X^3$, $X^4$, $X^5$ and $X^6$ are as hereinbefore defined, Y is $-CO_2R^{16}$ and the $L^2$ moiety within one of $X^3$, $X^4$ and $X^5$ is a

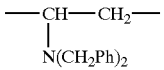

linkage. The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Esters of formula (I), wherein $R^1$, $X^1$, $X^2$, $X^3$, $X^4$, $X^5$ and $X^6$ are as hereinbefore defined Y is $-CO_2R^{16}$ and the $L^2$ moiety within one of $X^3$, $X^4$ and $X^5$ is a

linkage, may be similarly prepared by hydrogenation of esters of formula (I), wherein $R^1$, $X^1$, $X^2$, $X^3$, $X^4$, $X^5$ and $X^6$ are as hereinbefore defined, Y is $-CO_2R^{16}$ and the $L^2$ moiety within one of $X^3$, $X^4$ and $X^5$ is a

linkage.

Esters of formula (I), wherein $R^1$, $X^1$, $X^2$, $X^3$, $X^4$, $X^5$ and $X^6$ are as hereinbefore defined Y is $-CO_2R^{16}$ and the $L^2$ moiety within one of $X^3$, $X^4$ and $X^5$ is a

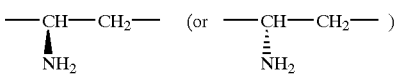

linkage, may also be obtained following standard recrystallisation of salts of the racemic mixture, for example recrystallisation of the tartrate salt.

Esters of formula (I), wherein $R^1$, $X^1$, $X^2$, $X^3$, $X^4$, $X^5$ and $X^6$ are as hereinbefore defined Y is $-CO_2R^{16}$ and the $L^2$ moiety within one of $X^3$, $X^4$ and $X^5$ is a

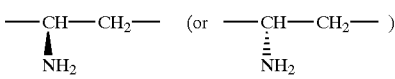

linkage, may also be obtained by the application of standard enzymatic resolution procedures for example those described by Soloshonok, V. A., et.al., Tetrahedron: Asymmetry 6 (1995) 7, 1601–1610.

Esters of formula (I), wherein $R^1$, $X^1$, $X^2$, $X^3$, $X^4$, $X^5$ and $X^6$ are as hereinbefore defined Y is $-CO_2R^{16}$ and the $L^2$ moiety within one of $X^3$, $X^4$ and $X^5$ is a

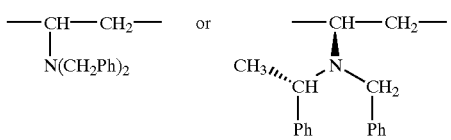

linkage, may be prepared by reaction of esters of formula (I), wherein $R^1$, $X^1$, $X^2$, $X^3$, $X^4$, $X^5$ and $X^6$ are as hereinbefore defined, Y is —$CO_2R^{16}$ and the $L^2$ moiety within one of $X^3$, $X^4$ and $X^5$ is a —CH=CH— linkage, with an alkali metal hydride, such as sodium hydride, in an inert solvent, e.g. tetrahydrofuran, and at a temperature at about room temperature, and subsequent reaction with the anion derived from treating dibenzylamine, or (S)-N-benzyl-(α-methylbenzylamine, with butyllithium, at a temperature at about −78° C.

Esters of formula (I), wherein $R^1$, $X^1$, $X^2$, $X^3$, $X^4$, $X^5$ and $X^6$ are as hereinbefore defined Y is —$CO_2R^{16}$ and the $L^2$ moiety within one of $X^3$, $X^4$ and $X^5$ is a —CH=CH— linkage, may be prepared by reaction of compounds of formula (1), wherein $R^1$, $X^1$, $X^2$ and $X^6$ are as hereinbefore defined, one of $X^7$, $X^8$ and $X^9$ represents C—$R^{18}$ [in which $R^{18}$ is —$R^2$—$R^3$—$Ar^1$—I (where $R^2$, R2 and $Ar^1$ are as hereinbefore defined) and the others independently represent N or $CR^{10}$ (where $R^{10}$ is as hereinbefore defined), with an acrylic acid ester, such as tert-butyl acrylate, in the presence of palladium acetate, a triarylphosphine, such as tri(2-methylphenyl)phosphine, and a tertiary amine, such as tributylamine, in an inert solvent, such as dimethylformamide and at a temperature up to about 100° C.

Compounds of formula (1), wherein $R^1$, $X^1$, $X^2$ and $X^6$ are as hereinbefore defined, one of $X^7$, $X^8$ and $X^9$ represents C—$R^{18}$ (in which $R^{18}$ is as described hereinabove, or a suitably protected derivative thereof) and the others independently represent N or $CR^{10}$ (where $R^{10}$ is as hereinbefore defined), may be prepared by the application or adaptation of methods described in prepared as described in the specification of International Patent Application Publication No. WO 96/22966.

Compounds of formula (2), wherein $R^{16}$ $Ar^1$ and $L^2$ are as hereinbefore defined and $R^4$ is hydrogen may be prepared by reduction of the corresponding nitro compounds. The reduction may be carried out using iron powder and ammonium chloride, in aqueous ethanol at a temperature at about reflux. The reduction may also be carried out by hydrogenation using standard conditions, for example those described hereinbefore.

Intermediates of formulae (resin 3), (resin 4), (resin 6) and (resin 7) are novel compounds and, as such, they and their processes described herein for their preparation constitute further features of the present invention.

The present invention is further Exemplified but not limited by the following illustrative Examples and Reference Examples.

Mass spectra were recorded on a Micromass Platform II mass spectrometer fitted with an Electrospray source and an HP1100 liquid chromatograph; using a mixture of acetonitrile and water (1:1, v/v) as the mobile phase, a flow rate of 0.3 ml/minute, an injection volume of 20 μl, a run time of 2.0 minutes, a scan range of 150–850 Daltons Positive/Negative, a scan time of 2.0 seconds, an ESI voltage of 3.5 Kv, an ESI pressure of 20 n/m2 Nitrogen.

The ions recorded are positive ions.

EXAMPLE 1

(5-{4-[3-(2-Methylphenyl)ureido]-phenylacetylamino}pyrid-2-yl)-thioacetic acid

A mixture of 5-amino-(pyrid-2-yl)-thioacetic acid methyl ester [930 mg, Reference Example 1(a)], 4-[3-(2-methylphenyl)ureido]phenylacetic acid (1.26 g, prepared as described in Example 21 of International Patent Application Publication No. WO 96/22966), O-(7-azabenzotriazol-1-yl)-1,1,3,3-tetramethyluronium hexafluorophosphate (1.69 g) and diisopropylethylamine (1.2 g) in dimethylformamide (50 ml) was stirred at ambient temperature for 1 hour. The mixture was evaporated then poured into water (500 ml). The resultant solid was washed with water (50 ml) and then washed twice with diethyl ether (50 ml). The solid was suspended in methanol (100 ml), then treated with sodium hydroxide solution (10 ml, 1M). The mixture was heated at reflux for 5 hours, then cooled, then evaporated. The residue was treated with hydrochloric acid (200 ml, 1M). The resultant solid was filtered, washed with water (20 ml), then washed twice with diethyl ether (20 ml), then recrystallised from ethanol to give the title compound (220 mg) as a yellow solid, m.p. >235° C. (with decomposition). MS: $MH^+$ 451.

EXAMPLE 2

(a) 3-(5-{3-Methoxy-4-[3-(2-methylphenyl)ureido]-phenylacetylamino}pyrid-2-yl)-propanoic acid A stirred mixture of 3-(5-{3-methoxy-4-[3-(2-methylphenyl)ureido]-phenylacetylamino}pyrid-2-yl)-propanoic acid ethyl ester [0.62 g, Reference Example 3(a)] and ethanol (40 ml) was treated with 4% aqueous sodium hydroxide solution (3.2 ml) and then heated to 50° C. After stirring at 50° C. for 7 hours, the reaction mixture was cooled and then left to stand at room temperature over night. The reaction mixture was partially concentrated in vacuo, washed with diethyl ether and then acidified to pH 1.0 by addition of hydrochloric acid (1M). The resultant white solid was collected, washed with water and then dried in vacuo. Recrystallisation from aqueous acetonitrile gave the title compound (0.32 g) as a white crystalline solid, m.p. 191–192° C. (with decomposition). MS: $MH^+$ 463.

(b) By proceeding in a manner similar to Example 2(a) above but using 3-(5-{3-methoxy-4-[3-(2-methylphenyl)ureido]-phenylacetylamino}pyrid-2-yl)-2-methylpropanoic acid ethyl ester [Reference Example 3(b)], there was prepared 3-(5-{3-methoxy-4-[3-(2-methylphenyl)ureido]-phenylacetylamino}pyrid-2-yl)-2-methylpropanoic acid, m.p. 196–197° C. (with decomposition). MS: $MH^+$ 477. [Elemental analysis:—C, 65.2; H, 6.1; N, 11.6%. Calculated for $C_{26}H_{28}N_4O_5$:—C, 65.5; H 5.9; N, 11.8%].

(c) By proceeding in a manner similar to Example 2(a) above but using 3-(6-{3-methoxy-4-[3-(2-methylphenyl)ureido]-phenylacetylamino}pyrid-3-yl)-propanoic acid ethyl ester [Reference Example 3(c)], there was prepared 3-(6-{3-methoxy-4-[3-(2-methylphenyl)ureido]-phenylacetylamino}pyrid-3-yl)-propanoic acid, m.p. 175–176° C. (with decomposition). MS: $MH^+$ 463. [Elemental analysis:—C, 64.9; H, 5.7; N, 12.1%. Calculated for $C_{25}H_{26}N_4O_5$:—C, 64.9; H, 5.7; N, 12.0%].

EXAMPLE 3

(a) (R)-3-(4-{3-Methoxy-4-[3-(2-methylphenyl)ureido]phenylacetylamino}phenyl)-3-(methanesulphonylamino)-propanoic acid (R)-3-(4-{3-methoxy-4-[3-(2-methylphenyl)ureido]phenylacetylamino}phenyl)-3-(methanesulphonylamino)-propanoic acid tert-butyl ester [55 mg, Reference Example 6(a)] was dissolved in anhydrous trifluoroacetic acid (2 ml) and allowed to stand at ambient temperature for 30 minutes.

The reaction mixture was evaporated and the residue was triturated with diethyl ether to yield the title compound (42 mg) as an amorphous white solid. MS: MH$^+$ 555. [Elemental analysis:—C, 55.3; H, 5.1; N, 9.2%. Calculated for $C_{27}H_{30}N_4O_7S$:—C, 58.5; H, 5.45; N, 10.1%].

(b) By proceeding in a manner similar to Example 3(a) but using 3-(acetylamino)-3-(4-{3-methoxy-4-[3-(2-methylphenyl)ureido]phenylacetylamino}phenyl)-propanoic acid tert-butyl ester [Reference Example 6(b)] there was prepared 3-(acetylamino)-3-(4-{3-methoxy-4-[3-(2-methylphenyl)ureido]-phenylacetylamino}phenyl)-propanoic acid. MS: MH$^+$ 519. [Elemental analysis:—C, 61.9; H, 5.05; N, 10.1%. Calculated for $C_{28}H_{30}N_4O_6$:—C, 64.8; H, 5.8; N, 10.8%].

(c) By proceeding in a manner similar to Example 3(a) but using 3-(4-{3-methoxy-4-[3-(2-methylphenyl)ureido]phenylacetylamino}phenyl)-3-(benzoylamino)-propanoic acid tert-butyl ester [Reference Example 6(c)] there was prepared 3-(benzoylamino)-3-(4-{3-methoxy-4-[3-(2-methylphenyl)-ureido]phenylacetylamino}phenyl)-propanoic acid. MS: MNa$^+$ 603. [Elemental analysis:—C, 66.65; H, 5.05; N, 9.35%. Calculated for $C_{33}H_{32}N_4O_6$:—C, 68.3; H, 5.55; N, 9.65%].

(d) By proceeding in a manner similar to Example 3(a) but using 3-(4-{3-methoxy-4-[3-(2-methylphenyl)ureido]phenylacetylamino}phenyl)-3-(pyridine-3-carbonylamino)-propanoic acid tert-butyl butyl ester [Reference Example 6(d)] there was prepared 3-(4-{3-methoxy-4-[3-(2-methylphenyl)ureido]phenylacetylamino}phenyl)-3-(pyridine-3-carbonylamino)-propanoic acid trifluoroacetate salt. MS: MH$^+$ 582. [Elemental analysis:—C, 56.85; H, 4.4; N, 9.65%. Calculated for $C_{32}H_{31}N_5O_6.CF_3CO_2H$:—C, 58.7; H, 4.6; N, 10.05%].

(e) By proceeding in a manner similar to Example 3(a) but using (R)-3-amino-3-(4-{3-methoxy-4-[3-(2-methylphenyl)ureido]phenylacetylamino}phenyl)-propanoic acid tert-butyl ester [Reference Example 7(a)] there was prepared (R)-3-amino-3-(4-{3-methoxy-4-[3-(2-methylphenyl)ureido]phenylacetylamino}phenyl)-propanoic acid trifluoroacetate salt. MS: MH$^+$ 477. [Elemental analysis:—C, 55.55; H, 5.15; N, 9.3%. Calculated for $C_{26}H_{28}N_4O_5.CF_3CO_2H$:—C, 56.9; H, 4.95; N, 9.5%].

(f) By proceeding in a manner similar to Example 3(a) but using 3-amino-3-(4-{3-methoxy-4-[3-(2-methylphenyl)ureido]phenylacetylamino}phenyl)-propanoic acid tert-butyl ester [Reference Example 7(b)] there was prepared 3-amino-3-(4-{3-methoxy-4-[3-(2-methylphenyl)ureido]-phenylacetylamino}phenyl)propanoic acid di-trifluoroacetate salt. MS: MH$^+$ 477. [Elemental analysis:—C, 51.95; H, 4.3; N, 8.4%. Calculated for $C_{26}H_{28}N_4O_5.2CF_3CO_2H$:—C, 51.1; H, 4.5; N, 7.95%].

(g) By proceeding in a manner similar to Example 3(a) but using 3-(n-butylamino)-3-(4-{3-methoxy-4-[3-(2-methylphenyl)ureido]phenylacetylamino}phenyl)-propanoic acid tert-butyl ester [Reference Example 10(a)] there was prepared 3-(n-butylamino)-3-(4-{3-methoxy-4-[3-(2-methylphenyl)ureido]phenylacetylamino}phenyl)-propanoic acid trifluoroacetate salt, m.p. 110–130° C. (amorphous). MS: MH$^+$ 533.

(h) By proceeding in a manner similar to Example 3(a) but using 3-benzylamino-3-(4-{3-methoxy-4-[3-(2-methylphenyl)ureido]phenylacetylamino}phenyl)-propanoic acid tert-butyl ester [Reference Example 10(b)] there was prepared 3-benzylamino-3-(4-{3-methoxy-4-[3-(2-methylphenyl)ureido]phenylacetylamino}phenyl)-propanoic acid trifluoroacetate salt. MS: MH$^+$ 566. [Elemental analysis:—C, 61.05; H, 5.05; N, 8.0%. Calculated for $C_{33}H_{34}N_4O_5.CF_3CO_2H$:—C, 61.75; H, 5.2; N, 8.2%].

(i) By proceeding in a manner similar to Example 3(a) but using 3-(4-{3-methoxy-4-[3-(2-methylphenyl)ureido]phenylacetylamino}phenyl)-3-(2-phenylethylamino)-propanoic acid tert-butyl ester [Reference Example 10(c)] there was prepared 3-(4-{3-methoxy-4-[3-(2-methylphenyl)ureido]phenylacetylamino}phenyl)-3-(2-phenylethylamino)-propanoic acid trifluoroacetate salt, m.p. 105–140° C. (amorphous). MS: MH$^+$ 580.

(j) By proceeding in a manner similar to Example 3(a) but using (R)-3-[(1-tert-butoxycarbonylmethyl-piperidin-4-carbonyl)-amino]-3-(4-{3-methoxy-4-[3-(2-methylphenyl)ureido]phenylacetylamino}phenyl)-propanoic acid methyl ester [Reference Example 37(b)] there was prepared (R)-3-[(1-carboxymethyl-piperidin-4-carbonyl)-amino]-3-(4-{3-methoxy-4-[3-(2-methylphenyl)ureido]phenylacetylamino}phenyl)-propanoic acid trifluoroacetate salt, MS: MH$^+$ 660.

EXAMPLE 4

(a) 3-(4-{3-Methoxy-4-[3-(2-methylphenyl)ureido]phenylacetylamino}phenyl)-3-(morpholin-4-yl)-propanoic acid hydrochloride salt A mixture of 3-(4-{3-methoxy-4-[3-(2-methylphenyl)ureido]phenylacetylamino}phenyl)-3-(morpholin-4-yl)-propanoic acid tert-butyl ester [100 mg, Reference Example 11(a)] anhydrous trifluoroacetic acid (3 ml) and dichloromethane (5 ml) allowed to stand at ambient temperature for 1 hour. The reaction mixture was evaporated and the residue was partitioned between ethyl acetate and 1.0M hydrochloric acid. The aqueous layer was evaporated and the residue was triturated with a mixture of methanol and diethyl ether to yield the title compound (46 mg) as a white solid, m.p. 164–171° C. (amorphous). MS: MH$^+$ 547.

(b) By proceeding in a manner similar to Example 4(a) but using 3-(4-{3-methoxy-4-[3-(2-methylphenyl)ureido]phenylacetylamino}phenyl)-3-(4-methylpiperazin-1-yl)-propanoic acid tert-butyl ester [Reference Example 11(b)] there was prepared 3-(4-{3-methoxy-4-[3-(2-methylphenyl)ureido]phenylacetylamino}phenyl)-3-(4-methylpiperazin-1-yl)-propanoic acid hydrochloride salt, m.p. 174–184° C. (amorphous). MS: MH$^+$ 560.

(c) By proceeding in a manner similar to Example 4(a) but using (R)-3-(N-Acetyl-N-methylamino)3-(4-{4-[3-(2-methylphenyl)ureido]phenylacetyl-N-methylamino}phenyl)-propionic acid tert-butyl ester (0.65 g, Reference Example 21) there was prepared (R)-3-(N-acetyl-N-methylamino)-3-(4-{4-[3-(2-methylphenyl)ureido]phenylacetyl-N-methylamino}phenyl)-propionic acid as a white foam. HPLC retention time=11.9 minutes. M$^-$515 (ES$^-$)

EXAMPLE 5

(a) (R)-3-Benzoylamino-3-(4-{3-methoxy-4-[3-(2-methylphenyl)ureido]phenyl-acetylamino}phenyl)-propanoic acid A mixture of (R)-3-benzoylamino-3-(4-{3-methoxy-4-[3-(2-methylphenyl)ureido]phenyl-acetylamino}phenyl)-propanoic acid methyl ester [4.08 g, Reference Example 12(a)], and methanol (40 ml) was heated to 40° C. and then treated with 10% aqueous sodium hydroxide solution (34 ml). After stirring at 40° C. for 2.5 hours, the reaction mixture was cooled and then acidified to pH 1.0 by addition of hydrochloric acid (1M). The resultant white solid was collected, washed with water and then dried in vacuo. Recrystallisation from acetic acid gave the title compound as a white crystalline solid (3.2 g), m.p. 220–222° C. MS: MH+ 581. [Elemental analysis:—C, 68.0; H, 5.4; N, 9.5%. Calculated for $C_{33}H_{32}N_4O_6$:—C, 68.3; H, 5.6; N, 9.65%]. 99% ee by HPLC analysis on a CHIRALPAK AD F294 column eluting with heptane:isopropanol:ethanol:trifluoroacetic acid (200:25:25:1) at a rate of 0.7 ml/min.

(b) (R)-3-acetylamino-3-(4-{3-methoxy-4-[3-(2-methylphenyl)ureido]phenyl-acetylamino}phenyl)-propanoic acid hemihydrate By proceeding in a manner similar to Example 5(a) but using (R)-3-acetylamino-3-(4-{3-methoxy-4-[3-(2-methylphenyl)ureido]phenylacetylamino}phenyl)-propanoic acid methyl ester [Reference Example 12(b)] and lithium hydroxide instead of sodium hydroxide, there was prepared (R)-3-acetylamino-3-(4-{3-methoxy-4-[3-(2-methylphenyl)ureido]phenyl-acetylamino}phenyl)-propanoic acid hemihydrate, m.p. 244° C. (with decomposition). MS: MH+ 519. [Elemental analysis:—C, 63.8; H, 5.5; N, 10.5%. Calculated for $C_{28}H_{30}N_4O_6.0.5H_2O$:—C, 63.75; H, 5.9; N, 10.6%]. 99% ee by HPLC analysis on a CHIRALPAK AD F294 column eluting with a mixture of heptane, isopropanol, ethanol and trifluoroacetic acid (200:25:25:1, v/v/v/v) at a rate of 0.7 ml/min. (RT of R-isomer=36.5 minutes; RT of enantiomer= 47.4 minutes).

(c) By proceeding in a manner similar to Example 5(a) but using (R)-3-benzyloxycarbonyl-amino-3-(4-{3-methoxy-4-[3-(2-methylphenyl)ureido]phenylacetylamino}phenyl)-propanoic acid methyl ester [Reference Example 12(c)], there was prepared (R)-3-benzyloxycarbonylamino-3-(4-{3-methoxy-4-[3-(2-methylphenyl)ureido]phenylacetylamino}phenyl)-propanoic acid m.p. 170–173° C. (with decomposition). MS: MH+ 611. [Elemental analysis:—C, 65.7; H, 5.4; N, 8.9%. Calculated for $C_{34}H_{34}N_4O_7.0.5H_2O$:—C, 65.9; H, 5.7; N, 9.0%].

(d) By proceeding in a manner similar to Example 5(a) but using (R)-3-phenylsulphonylamino-3-(4-{3-methoxy-4-[3-(2-methylphenyl)ureido]phenylacetylamino}-phenyl) propanoic acid methyl ester [Reference Example 12(d)], there was prepared (R)-3-phenylsulphonylamino-3-(4-{3-methoxy-4-[3-(2-methylphenyl)ureido]phenylacetylamino}-phenyl)-propanoic acid m.p. 181–184° C. (with decomposition). MS: MH+ 617. [Elemental analysis:—C, 61.6; H, 5.1; N, 9.0%. Calculated for $C_{32}H_{32}N_4O_7S.0.25H_2O$:—C, 61.9; H, 5.3; N, 9.0%].

(e) By proceeding in a manner similar to Example 5(a) but using (R)-3-(pyridine-3-carbonylamino)-3-(4-{3-methoxy-4-[3-(2-methylphenyl)ureido]phenylacetylamino}phenyl)-propanoic acid methyl ester [Reference Example 12(e)], there was prepared (R)-3-(pyridine-3-carbonylamino)-3-(4-{3-methoxy-4-[3-(2-methylphenyl)ureido]phenylacetylamino}phenyl)-propanoic acid m.p. 218–220° C. MS: MH+ 582. [Elemental analysis:—C, 62.3; H, 5.1; N, 11.1%. Calculated for $C_{32}H_{31}N_5O_6.2H_2O$:—C, 62.2; H, 5.8; N, 11.4%].

(f) By proceeding in a manner similar to Example 5(a) but using (R)-3-(pyridine-3-sulphonylamino)-3-(4-{3-methoxy-4-[3-(2-methylphenyl)ureido]phenylacetylamino}phenyl)-propanoic acid methyl ester [Reference Example 12(f)], there was prepared (R)-3-(pyridine-3-sulphonylamino)-3-(4-{3-methoxy-4-[3-(2-methylphenyl)ureido] phenylacetylamino}phenyl -propanoic acid m.p. 191–193° C. MS: MH+ 618. [Elemental analysis:—C, 58.5; H, 5.1; N, 11.0%. Calculated for $C_{31}H_{31}N_5O_7S.H_2O$:—C, 58.6; H, 5.0; N, 11.0%].

(g) By proceeding in a manner similar to Example 5(a) but using (R)-3-(5-dimethylamino-1-naphthalenesulphonylamino)-3-(4-{3-methoxy-4-[3-(2-methylphenyl)ureido]phenylacetyl-amino}phenyl)-propanoic acid methyl ester [Reference Example 29(a)], there was prepared (R)-3-(5-dimethylamino-1-naphthalenesulphonylamino)-3-(4-{3-methoxy-4-[3-(2-methylphenyl)-ureido]phenylacetylamino}phenyl)-propanoic acid m.p. 160° C. (with decomposition). MS: MH+ 710. [Elemental analysis:—C, 62.8; H, 6.2; N, 9.3%. Calculated for $C_{38}H_{39}N_5O_7S.H_2O.C_3H_8O$:—C, 62.5; H, 6.3; N, 8.9%].

(h) By proceeding in a manner similar to Example 5(a) but using (R)-3-(4-carboxybutanoyl-amino)-3-(4-{3-methoxy-4-[3-(2-methylphenyl)ureido]phenylacetylamino}-phenyl)-propanoic acid methyl ester [Reference Example 28(a)], there was prepared (R)-3-(4-carboxybutanoyl-amino)-3-(4-{3-methoxy-4-[3-(2-methylphenyl)ureido] phenylacetylamino}-phenyl)-propanoic acid m.p. 217–219° C. MS: MH+ 591. [Elemental analysis:—C, 62.3; H. 5.4; N, 9.45%. Calculated for $C_{31}H_{34}N_4O_8.0.5H_2O$:—C, 62.1; H, 5.9; N, 9.3%].

(i) By proceeding in a manner similar to Example 5(a) but using (R)-3-(3-carboxypropanoyl-amino)-3-(4-{3-methoxy-4-[3-(2-methylphenyl)ureido]phenylacetylamino}-phenyl)-propanoic acid methyl ester [Reference Example 28(b)], there was prepared (R)-3-(3-carboxypropanoyl-amino)-3-(4-{3-methoxy-4-[3-(2-methylphenyl)ureido] phenylacetylamino}-phenyl)-propanoic acid m.p. 177–180° C. MS: MH+ 577. [Elemental analysis:—C, 60.6; H, 5.3; N, 9.2%. Calculated for $C_{30}H_{32}N_4O_8.H_2O$:—C, 60.6; H, 5.75; N, 9.4%].

(j) By proceeding in a manner similar to Example 5(a) but using (R)-3-(1-methylimidazol-4-ylsulphonylamino)-3-(4-{3-methoxy-4-[3-(2-methylphenyl)ureido] phenylacetylamino}phenyl)-propanoic acid methyl ester [Reference Example 29(b)], there was prepared (R)-3-(1-methylimidazol-4-ylsulphonylamino)-3-(4-{3-methoxy-4-[3-(2-methylphenyl)ureido]-phenylacetylamino}phenyl)-propanoic acid m.p. 194–195° C. MS: MH+ 621.

(k) By proceeding in a manner similar to Example 5(a) but using (R)-3-(N-acetyl-N-methylamino)-3-(4-{3-methoxy-4-[3-(2-methylphenyl)ureido]phenylacetylamino}phenyl)-propanoic acid methyl ester [Reference Example 12(g)], there was prepared (R)-3-(N-acetyl-methylamino)-3-(4-{3-methoxy-4-[3-(2-methylphenyl)ureido] phenylacetylamino}phenyl)-propanoic acid, m.p. 227–229° C. MS: MH+ 533.

(l) By proceeding in a manner similar to Example 5(a) but using (R)-3-(N-methanesulphonyl-methylamino)-3-(4-{3-methoxy-4-[3-(2-methylphenyl)ureido]-phenylacetyl-amino}phenyl)-propanoic acid methyl ester [Reference Example 12(h)] there was prepared (R)-3-(N-methanesulphonyl-methylamino)-3-(4-{3-methoxy-4-[3-(2-methylphenyl)-ureido]phenylacetylamino}phenyl)-propanoic acid, m.p. 201–203° C. MS: MH+ 569.

(m) By proceeding in a manner similar to Example 5(a) but using (R)-3-[(morpholin-1yl)-acetylamino]-3-(4-{3-methoxy-4-[3-(2-methylphenyl)ureido] phenylacetylamino}phenyl)-propanoic acid methyl ester [Reference Example 37(a)], there was prepared (R)-3-(morpholin-1-ylacetylamino)-3-(4-{3-methoxy-4-[3-(2- methylphenyl)ureido]phenylacetylamino}phenyl)-propanoic acid m.p. 183–184° C. MS: MH+ 604.

(n) By proceeding in a manner similar to Example 5(a) but using (R)-3-acetylamino-3-(4-{3-methylthio-4-[3-(2-methylphenyl)ureido]phenylacetylamino}phenyl)-propanoic acid methyl ester [Reference Example 12(m)], there was prepared (R)-3-acetylamino-3-(4-{3-methylthio-4-[3-(2-methylphenyl)ureido]phenylacetylamino}phenyl)-propanoic acid, m.p. 205–207° C. MS: MH+ 535. [Elemental analysis:—C, 61.4; H, 5.6; N, 10.0%. Calculated for $C_{28}H_{30}N_4O_5S$:—C, 62.9; H, 5.6; N, 10.5%].

(o) By proceeding in a manner similar to Example 5(a) but using (R)-3-acetylamino-3-(4-{3-methylsulphinyl-4-[3-(2-methylphenyl)ureido]phenylacetylamino}phenyl)-propanoic acid methyl ester [Reference Example 12(n)], there was prepared (R)-3-acetylamino-3-(4-{3-methylsulphinyl-4-[3-(2-methylphenyl)ureido]phenylacetylamino}phenyl)-propanoic acid, m.p. 202–295° C. MS: MH+ 551. [Elemental analysis:—C, 56.3; H, 5.2; N, 9.4%. Calculated for $C_{28}H_{30}N_4O_6S.0.25H_2O$:—C, 56.6; H, 5.9; N, 9.4%].

(p) By proceeding in a manner similar to Example 5(a) but using (R)-3-acetylamino-3-(4-{3-methylsulphonyl-4-[3-(2-methylphenyl)ureido]phenylacetylamino}phenyl)-propanoic acid methyl ester [Reference Example 12(o)], there was prepared (R)-3-acetylamino-3-(4-{3-methylsulphonyl-4-[3-(2-methylphenyl)ureido]phenylacetylamino}phenyl)-propanoic acid, m.p. 220–223° C. MS: MH+ 567.

(q) By proceeding in a manner similar to Example 5(a) but using (R)-3-[2-(2-methoxy-ethoxy)acetylamino]-3-(4-{3-methoxy-4-[3-(2-methylphenyl)ureido]phenylacetylamino}phenyl)-propanoic acid methyl ester [Reference Example 12(p)], there was prepared (R)-3-[2-(2-methoxy-ethoxy)acetylamino]-3-(4-{3-methoxy-4-[3-(2-methylphenyl)ureido]phenylacetylamino}phenyl)-propanoic acid, m.p. 193–195° C. MS: MH+ 593. [Elemental analysis:—C, 62.5; H, 6.5; N, 9.4%. Calculated for $C_{31}H_{36}N_4O_8$:—C, 62.8; H, 6.1; N, 9.45%].

(r) By proceeding in a manner similar to Example 5(a) but using (R)-3-[(tetrahydropyran-4-carbonyl)amino]-3-(4-{3-methoxy-4-[3-(2-methylphenyl)ureido]phenylacetylamino}phenyl)-propanoic acid methyl ester [Reference Example 12(q)], there was prepared (R)-3-[(tetrahydropyran-4-carbonyl)amino]-3-(4-{3-methoxy-4-[3-(2-methylphenyl)ureido]-phenylacetylamino}phenyl)-propanoic acid, m.p. 227–230 ° C. (dec). MS: MH+ 589. [Elemental analysis:—C, 64.9; H, 6.5; N, 9.4% Calculated for $C_{32}H_{36}N_4O_7$:—C, 65.3; H, 6.2; N, 9.5%].

(s) By proceeding in a manner similar to Example 5(a) but using (R)-3-[(5-methyl-isoxazole-3-carbonyl)-amino]-3-(4-{3-methoxy-4-[3-(2-methylphenyl)ureido]phenylacetylamino}phenyl)-propanoic acid methyl ester [Reference Example 12(i)], there was prepared (R)-3-[(5-methyl-isoxazole-3-carbonyl)-amino]-3-(4-{3-methoxy-4-[3-(2-methylphenyl)ureido]-phenylacetylamino}phenyl)-propanoic acid, m.p. 200° C. MS: MH+ 586. [Elemental analysis:—C, 63.6; H, 5.15; N, 12.0%. Calculated for $C_{31}H_{31}N_5O_7$:—C, 63.6; H, 5.3; N, 12.0%].

(t) By proceeding in a manner similar to Example 5(a) but using (R)-3-[(thiophene-2-carbonyl)-amino]-3-(4-{3-methoxy-4-[3-(2-methylphenyl)ureido]phenylacetylamino}phenyl)-propanoic acid methyl ester [Reference Example 12(j)], there was prepared (R)-3-[(thiophene-2-carbonyl)-amino]-3-(4-{3-methoxy-4-[3-(2-methylphenyl)ureido]phenylacetylamino}phenyl)-propanoic acid, m.p. 222–224° C. (dec). MS: MH+ 587. [Elemental analysis:—C, 63.1; H, 5.3; N, 9.5%. Calculated for $C_{31}H_{31}N_4O_6S$:—C, 63.5; H, 5.15; N, 9.55%].

(u) By proceeding in a manner similar to Example 5(a) but using (R)-3-[(4-methoxycarbonyl-benzoyl)-amino]-3-(4-{3-methoxy-4-[3-(2-methylphenyl)ureido]phenylacetylamino}phenyl)-propanoic acid methyl ester [Reference Example 12(k)], there was prepared (R)-3-[(4-carboxybenzoyl)-amino]-3-(4-{3-methoxy-4-[3-(2-methylphenyl)ureido]phenylacetyl-amino}phenyl)-propanoic acid, m.p. 178–180° C. (dec). MS: MH+ 625. [Elemental analysis:—C, 62.0; H, 5.1; N, 8.6%. Calculated for $C_{34}H_{32}N_4O_8.2 H_2O$:—C, 62.0; H, 5.5; N, 8.5%].

(v) By proceeding in a manner similar to Example 5(a) but using (R)-3-[(pyridazin-3-carbonyl)-amino]-3-(4-{3-methoxy-4-[3-(2-methylphenyl)ureido]phenylacetylamino}phenyl)-propanoic acid methyl ester [Reference Example 12(r)], there was prepared (R)-3-[(pyridazin-3-carbonyl)-amino]-3-(4-{3-methoxy-4-[3-(2-methylphenyl)ureido]phenylacetylamino}phenyl)-propanoic acid, m.p. 190° C. (dec). MS: MH+ 583. [Elemental analysis:—C, 61.1; H, 5.1; N, 13.5%. Calculated for $C_{31}H_{30}N_6O_6.1.5 H_2O$:—C, 61.1; H, 5.5; N, 13.8%].

(w) By proceeding in a manner similar to Example 5(a) but using (R)-3-[(3,4-dimethoxy-benzoyl)-amino]-3-(4-{3-methoxy-4-[3-(2-methylphenyl)ureido]phenylacetylamino}-phenyl)-propanoic acid methyl ester [Reference Example 12(l)], there was prepared (R)-3-[(3,4-dimethoxybenzoyl)-amino]-3-(4-{3-methoxy-4-[3-(2-methylphenyl)ureido]phenylacetyl-amino}phenyl)-propanoic acid, m.p. 184–186. MS: MH+ 641. [Elemental analysis:—C, 62.6; H, 5.45; N, 8.3%. Calculated for $C_{35}R_{36}N_4O_8.1.75 H_2O$:—C, 62.5; H, 5.9; N, 8.3%].

(x) By proceeding in a manner similar to Example 5(a) but using (R)-3-[(pyridazin-3-carbonyl)-amino]-3-(4-{4-[3-(2-methylphenyl)ureido]phenylacetylamino}phenyl)-propanoic acid methyl ester [Reference Example 12(s)], there was prepared (R)-3-[(pyridazin-3-carbonyl)-amino]-3-(4-{4-[3-(2-methylphenyl)ureido]phenylacetylamino}phenyl)-propanoic acid, m.p. 231–214° C. (dec). MS: MH+ 553.

(y) By proceeding in a manner similar to Example 5(a) but using (R)-3-[(4-carboxy-3,3-dimethyl-butanoyl)amino]-3-(4-{3-methoxy-4-[3-(2-methylphenyl)ureido]phenylacetylamino}-phenyl)-propanoic acid methyl ester [Reference Example 28(c)], there was prepared (R)-3-[(4-carboxy-3,3-dimethyl-butanoyl)amino]-3-(4-{3-methoxy-4-[3-(2-methylphenyl)ureido]-phenylacetylamino}-phenyl)-propanoic acid, m.p. 164° C. MS: MH+ 619. [Elemental analysis:—C, 62.0; H, 5.7; N, 8.9%. Calculated for $C_{33}H_{38}N_4O_8.1.25H_2O$:—C, 61.8; H, 6.3; N, 8.7%].

(z) By proceeding in a manner similar to Example 5(a) but using (R)-3-(benzoylamino)-3-(4-{4-[3-(2-methylphenyl)ureido]phenylacetylamino}-phenyl)-propanoic acid methyl ester [Reference Example 12(t)], there was prepared (R)-3-(benzoylamino)-3-(4-{4-[3-(2-methylphenyl)ureido]phenylacetylamino}phenyl)-propanoic acid, m.p. 203–204° C. (dec). MS: MH+ 551. [Elemental analysis:—C, 66.9; H, 5.5; N, 9.7%. Calculated for $C_{32}H_{30}N_4O_5.1.2H_2O$:—C, 67.2; H, 5.5; N, 9.8%].

(aa) By proceeding in a manner similar to Example 5(a) but using (R)-3-[4-methoxycarbonylbutanoyl)amino]-3-(4-{4-[3-(2-methylphenyl)ureido]phenylacetyl-amino}phenyl)-propanoic acid methyl ester [Reference Example 12(u)], there was prepared (R)-3-(4-carboxybutanoylamino)-3-(4-{4-[3-(2-methylphenyl)

ureido]phenylacetylamino}-phenyl)-propanoic acid, m.p. 233–235° C. MS: MH+ 561. [Elemental analysis:—C, 63.7; H, 5.95; N, 9.85%. Calculated for $C_{30}H_{32}N_4O_7.0.35H_2O$:—C, 63.6; H, 5.8; N, 9.9%].

(ab) By proceeding in a manner similar to Example 5(a) but using 3-[4-({3-methoxy-4-[3-(2-methylphenyl)ureido] phenylacetyl}-N-methylamino)phenyl]-butanoic acid ethyl ester [Reference Example 12(w)], there was prepared 3-[4-({3-methoxy-4-[3-(2-methylphenyl)ureido]-phenylacetyl}-N-methylamino)-phenyl]-butanoic acid. MS: MH+ 490. HPLC RT=14.46 minutes [gradient elution using a mixture of acetonitrile and water (1:4 to 4:1, v/v)].

(ac) By proceeding in a manner similar to Example 5(a) but using (R)-3-[(4-carboxypyridine-3-carbonyl)-amino]-3-(4-{3-methoxy-4-[3-(2-methylphenyl)ureido]phenyl-acetylamino}phenyl)-propanoic acid di-methyl ester [Reference Example 12(y)], there was prepared (R)-3-[(4-carboxypyridine-3-carbonyl)amino]-3-(4-{3-methoxy-4-[3-(2-methylphenyl)ureido]phenyl-acetylamino}phenyl)-propanoic acid, m.p. 293–295° C. MS: MH+ 626. [Elemental analysis:—C, 56.5; H, 5.3; N, 9.8%. Calculated for $C_{33}H_{31}N_5O_8.4H_2O$:—C, 56.8; H, 5.6; N, 10.0%].

(ad) By proceeding in a manner similar to Example 5(a) but using (R)-3-[2,2-di-(hydroxymethyl)propanoyl-amino]-3-(4-{3-methoxy-4-[3-(2-methylphenyl)ureido]-phenylacetylamino}phenyl)-propanoic acid methyl ester [Reference Example 12(z)], there was prepared (R)-3-[2,2-di-(hydroxymethyl)propanoyl-amino]-3-(4-{3-methoxy-4-[3-(2-methylphenyl)ureido]-phenylacetylamino}phenyl)-propanoic acid, m.p. 194° C. MS: MH+ 593.

(ae) By proceeding in a manner similar to Example 5(a) but using (R)-3-[2-(4-methyl-piperazin-1-yl)-acetylamino]-3-(4-{3-methoxy-4-[3-(2-methylphenyl)ureido]-phenylacetylamino}phenyl)-propanoic acid methyl ester [Reference Example 12(aa)], there was prepared (R)-3-[2-(4-methyl-piperazin-1-yl)-acetylamino]-3-(4-{3-methoxy-4-[3-(2-methylphenyl)ureido]-phenylacetylamino}phenyl)-propanoic acid, MS: MH+ 617.

(af) By proceeding in a manner similar to Example 5(a) but using (R)-3-[(1-carboxymethyl-piperidin-4-carbonyl)-amino]-3-(4-{3-methoxy-4-[3-(2-methylphenyl)ureido] phenylacetyl-amino}phenyl)-propanoic acid methyl ester [Example 3(k)], there was prepared (R)-3-[(1-carboxymethyl-piperidin-4-carbonyl)-amino]-3-(4-{3-methoxy-4-[3-(2-methylphenyl)-ureido]phenylacetylamino}phenyl)-propanoic acid, MS: MH+ 646.

(ae) By proceeding in a manner similar to Example 5(a) but using (R)-3-[2-(carboxymethyloxy)-acetylamino]-3-(4-{3-methoxy-4-[3-(2-methylphenyl)ureido]phenyl-acetylamino}phenyl)-propanic acid di-methyl ester [Reference Example 12(ab)], there was prepared (R)-3-[2-(carboxymethyloxy)-acetylamino]-3-(4-{3-methoxy-4-[3-(2-methylphenyl)-ureido]phenyl-acetylamino}phenyl)-propanoic acid, m.p. 181–183° C. MS: MH+ 593. [Elemental analysis:—C, 59.5; H, 5.6; N, 9.2%. Calculated for $C_{30}H_{32}N_4O_9$:—C, 59.5; H, 5.6; N, 9.3%].

EXAMPLE 6

(R)-3-Acetylamino-3-(4-{3-methoxy-4-[3-(2-methylphenyl)ureido]phenyl-acetylamino}phenyl)-propanoic acid sodium salt hydrate A suspension of (R)-3-acetylamino-3-(4-{3-methoxy-4-[3-(2-methylphenyl)ureido]-phenylacetylamino}phenyl)-propanoic acid [260 mg, Example 5(b)] in water (5 ml) was treated with aqueous sodium hydroxide (0.6 ml, 1M), After stirring at ambient temperature for 4 hours the reaction mixture was evaporated. The residue was recrystallised from 5% aqueous isopropanol to give the title compound (200 mg) as a white crystalline solid, m.p. 214–217° C. (with decomposition). [Elemental analysis:—C, 60.0; H, 5.8; N, 9.8%. Calculated for $C_{28}H_{29}N_4O_6Na.H_2O.0.25C_3H_8O$:—C, 60.2; H, 5.6; N, 9.8%].

EXAMPLE 7

(a) 3-(4-{3-Methoxy-4-[3-(2-methylphenyl)ureido] phenylacetylamino}phenyl)-5-(4-methylpiperazin-1-yl)-5-oxo-pentanoic acid A mixture of 3-(4-{3-methoxy-4-[3-(2-methylphenyl) ureido]phenylacetylamino}phenyl)-pentanedioic acid [740 mg, Reference Example 34], dichloromethane (50 ml) and tetrahydrofuran (10 ml) was treated with trifluoroacetic anhydride (84 mg). After stirring at ambient temperature for 3 hours the reaction mixture was evaporated. The residue was treated with dichloromethane (20 ml) then with N-methylpiperazine (80 mg). The mixture was stirred at ambient temperature for 2 hours then evaporated. The residue was triturated with diethyl ether to give the title compound (35 mg) as a light brown amorphous solid. MS: MH+ 602.

(b) By proceeding in a manner similar to Example 7(a) but using morpholine instead of N-methylpiperazine, there was prepared 3-(4-{3-methoxy-4-[3-(2-methylphenyl)ureido]-phenylacetylamino}phenyl)-5-(morpholin-4-yl)-5-oxo-pentanoic acid. MS: MH+ 589.

EXAMPLE 8

(R)-3-Benzoylamino-3-(4-{3-methoxy-4-[3-(2-methylphenyl)ureido]phenylacetylamino}phenyl)-propanoic acid triethanolamine salt A mixture of (R)-3-benzoylamino-3-(4-{3-methoxy-4-[3-(2-methylphenyl)ureido]phenylacetyl-amino}phenyl)-propanoic acid [1.0 g, Example 5(a)], tris(hydroxymethyl) aminomethane (0.208 g), tetrahydrofuran (80 ml) and water (15 ml) was stirred at 50° C. for 1.5 hours, then cooled to room temperature and then evaporated. The residue was recrystallised from ethanol to give the title compound as a white crystalline solid (1.1 g), m.p 135–140° C. (with decomposition). [Elemental analysis:—C, 61.6; H, 6.1; N, 9.5%. Calculated for $C_{33}H_{32}N_4O_6.C_4H_{11}NO_3.H_2O$:—C, 61.75; H, 6.3; N, 9.7%].

EXAMPLE 9

(a) (R)-3-[(S)-N-benzyl-α-methylbenzylamino]-3-(4-{3-methoxy-4-[3-(2-methylphenyl)ureido] phenylacetylamino}phenyl)-propanoic acid triflate salt A stirred suspension of 3-(4-{3-methoxy-4-[3-(2-methylphenyl)ureido]phenylacetylamino}-phenyl)-propenoic acid tert-butyl ester (1.0 g, Reference Example 8) in anhydrous tetrahydrofuran (50 ml) was treated with sodium hydride (0.23 g, 60% dispersion in mineral oil) under an atmosphere of nitrogen. After stirring for 30 minutes the resulting yellow solution was added dropwise to a solution of (S)-N-benzyl-α-methylbenzylamine (0.82 g) in anhydrous tetrahydrofuran (50 ml), cooled to −78° C., under an atmosphere of nitrogen, that had been treated with a solution of n-butyl lithium in hexanes (1.55 ml, 2.5M). This mixture was stirred for a further 15 minutes at −78° C. then poured into a mixture of ethyl acetate (200 ml) and saturated aqueous ammonium chloride solution (200 ml). The organic layer was separated, then dried over magnesium sulphate and then evaporated. The residue was subjected to flash chromatography on silica gel eluting with a mixture of ethyl acetate and dichloromethane (1:4, v/v) to give a yellow foam (840 mg). A portion of this material (100 mg) was treated with trifluoroacetic acid (2 ml) and allowed to stand at ambient temperature for 30 minutes. The reaction mixture was evaporated and the residue was triturated with diethyl ether to yield the title compound as a pale yellow solid (20 mg). MS: MH+ 671.

(b) By proceeding in a manner similar to Example 9(a) but using dibenzylamine in place of (S)-N-benzyl-(α-methylbenzylamine, there was prepared 3-(N,N-dibenzylamine)-3-(4-{3-methoxy-4-[3-(2-methylphenyl)ureido]phenylacetylamino}phenyl)-propanoic acid trifluoroacetate salt. MS: MH+ 657.

EXAMPLE 10

(R)-3-[(2-amino-acetyl)amino]-3-(4-{3-methoxy-4-[3-(2-methylphenyl)ureido]phenyl-acetylamino}phenyl)propanoic acid A mixture of (R)-3-amino-3-(4-{3-methoxy-4-[3-(2-methylphenyl)ureido]phenylacetylamino}-phenyl)-propanoic acid methyl ester (1.0 g, Reference Example 30), N-(tert-butoxycarbonyl)glycine (0.36 g), O-(7-azabenzotriazol-1-yl)-1,1,3,3-tetramethyluronium hexafluorophosphate (0.81 g) and diisopropylethylamine (0.75 ml) in dry dimethylformamide (20 ml) was stirred at ambient temperature for 30 minutes. The reaction mixture was poured into hydrochloric acid.(25 ml, 0.1M) and then extracted twice with ethyl acetate (50 ml). The combined organic extracts were washed with saturated aqueous sodium bicarbonate solution (25 ml), then with water (25 ml), then dried over magnesium sulphate and then evaporated. The residue was subjected to flash chromatography on silica gel eluting with ethyl acetate to give a yellow oil (300 mg). This material was dissolved in tetrahydrofuran (10 ml), then treated with aqueous sodium hydroxide solution (1.5 ml, 1.0M). The reaction mixture was heated at 40° C. for 4 hours then evaporated. The residue was treated with water (30 ml ) and the mixture was acidified to pH 1 by addition of concentrated hydrochloric acid. The resultant solid was filtered, then dried in vacuo, then treated with a cooled (0° C.) solution of trifluoroacetic acid (4 ml) in dichloromethane (9 ml). The mixture was warmed to ambient temperature, then stirred for 4.5 hours, then evaporated. The residue was triturated with diethyl ether to give the title compound as a white solid (150 mg), m.p. 105–108° C. (with decomposition). MS: MH+ 534.

EXAMPLE 11

(R)-3-[(1-oxido-pyridine-3-carbonyl)amino]-3-(4-{3-methoxy-4-[3-(2-methylphenyl)ureido]-phenylacetylamino}phenyl)-propanoic acid A mixture of (R)-3-[(pyridine-3-carbonyl)amino]-3-(4-{3-methoxy-4-[3-(2-methylphenyl)ureido]-phenylacetylamino}phenyl)-propanoic acid [0.4 g, Example 5(e)], acetic acid (2.5 ml) and hydrogen peroxide (0.5 ml) was stirred at 80° C. for 6 hours. The reaction mixture was evaporated and the residue was triturated with water. The resulting solid was subjected to flash chromatography on silica gel eluting with a mixture of dichloromethane, methanol and acetic acid (9:1:0.5, v/v/v) to give the title compound as a light brown solid (50 mg), m.p. 190° C. (with decomposition). MS: MH+ 598.

EXAMPLE 12

(R)-3-(4-carboxybutanoyl-amino)-3-(4-{3-methoxy-4-[3-(2-methylphenyl)ureido]phenylacetyl-amino}-phenyl)-propanoic acid A mixture of (R)-3-amino-3-[4-(tert-butoxycarbonylamino)phenyl]-propanoic acid methyl ester [1.5 g, Reference Example 7(c)], mono-methyl glutarate (0.7 ml), O-(7-azabenzotriazol-1-yl)-1,1,3,3-tetramethyluronium hexafluorophosphate (2.05 g), diisopropylethylamine (1.8 ml) and dimethylformamide (40 ml) was stirred at ambient temperature for 18 hours. The reaction mixture was evaporated to dryness and diluted with water (75 ml) and the resultant mixture acidified to pH1.0 by addition of concentrated hydrochloric acid. The mixture was extracted twice with ethyl acetate (75 ml). The combined extracts were washed with water (75 ml) then dried over magnesium sulphate and then evaporated. The resulting waxy fawn solid (3.8 g) was dissolved in dichloromethane (20 ml), cooled to 0° C., and the solution treated with trifluoracetic acid (4 ml). After stirring at ambient temperature for 2 hours the reaction mixture was evaporated and the residue taken up in ethyl acetate (50 m). The resultant solution was treated with ice cold saturated aqueous potassium carbonate solution (20 ml) with stirring at ambient temperature for 5 minutes. The organic layer was separated, washed with water (30 ml), dried over magnesium sulphate, and then evaporated to give (R)3-(4-carboxybutanoyl-amino)-3-(4-aminophenyl)-propanoic acid methyl ester (1.32 g) as a yellow oil.

A solution of 3-methoxy-4-[3-(2-methylphenyl)ureido] phenylacetic acid (1.28 g, prepared as described in Reference Example 31) in anhydrous dimethylformamide (50 ml), under an atmosphere of argon, was treated sequentially with O-(7-azabenzotriazol-1-yl)-1,1,3,3-tetramethyluronium hexafluorophosphate (1.55 g), diisopropylethylamine (1.35 ml) and a solution of (R)-3-(4-carboxybutanoyl-amino)-3-(4-aminophenyl)-propanoic acid methyl ester (1.25 g, prepared as described immediately hereinabove) in dimethylformamide (5 ml). After stirring for 2 hours at ambient temperature the reaction mixture was evaporated. The residue was treated with hydrochloric acid (50 ml, 1M) and extracted with ethyl acetate (100 ml). The combined organic extracts were washed with water (5 ml) and saturated aqueous potassium carbonate solution (50 ml) before being dried over magnesium sulphate and concentrated to dryness. The residue was subjected to flash chromatography on silica gel eluting with a mixture of methanol and dichloromethane (1:29, v/v) to give (R)-3-(4-carboxybutanoyl-amino)-3-(4-{3-methoxy-4-[3-(2-methylphenyl)ureido]phenyl-acetylamino}phenyl)-propanoic acid methyl ester a fawn solid (1.32 g). A solution of this material in tetrahydrofuran (40 ml) was heated to reflux and then treated with aqueous sodium hydroxide solution (34 ml, 2M). After stirring at reflux for a further 2.5 hours, the reaction mixture was cooled and then evaporated. The residue was diluted with water and the mixture acidified to pH 1.0 by addition of concentrated hydrochloric acid. The resultant white solid was washed with water, then dried in vacuo, then recrystallised from a mixture of ethanol and water (9:1 v/v) gave the title compound as a white crystalline solid (3.2 g), m.p. 220–222° C. MS: MH+ 591. [Elemental analysis:—C, 63.1; H, 5.3; N, 9.3%. Calculated for $C_{31}H_{34}N_4O_8$:—C, 63.0; H, 5.8; N, 9.5%]. >99% ee by HPLC analysis on a CHIRAL- PAK AD F294 column eluting with heptane: isopropanol:ethanol:trifluoroacetic acid (200:25:25:1) at a rate of 0.7 ml/min.

Reference Example 1

Methyl 5-amino-(pyrid-2-yl)-thioacetate

A mixture of methyl 5-nitro-(pyrid-2-yl)-thioacetate (6.3 g, Reference Example 2) iron powder (12 g), ammonium chloride (1 g), ethanol (150 ml) and water (150 ml) was heated at reflux for 2 hours. The reaction mixture was cooled and then filtered through a pad of diatomaceous earth. The filtrate was evaporated and the residue was subjected to flash chromatography on silica gel eluting with a mixture of ethyl acetate and pentane (1:1, v/v) to give the title compound as a yellow oil (3.0 g).

Reference Example 2

Methyl 5-nitro-(pyrid-2-yl)-thioacetate

A mixture of methyl thioacetate (3 g), diisopropylethylamine (8.14 g), 2-chloro-5-nitropyridine (5 g) and dimethylformamide (50 ml) was heated at 80° C. for 18 hours. The reaction mixture was cooled and then poured into water (500 ml). After stirring for 1 hour at ambient temperature the mixture was filtered to give the title compound (2.03 g) as a brown solid.

Reference Example 3

(a) 3-(5-{3-Methoxy-4-[3-(2-methylphenyl)ureido]-phenylacetylamino}pyrid-2-yl)-propanoic acid ethyl ester A solution of 3-methoxy-4-[3-(2-methylphenyl)ureido] phenylacetic acid (0.7 g, Reference Example 31) in anhydrous dimethylformamide (25 ml) was treated sequentially with O-(7-azabenzotriazol-1-yl)-1,1,3,3-tetramethyluronium hexafluorophosphate (0.85 g), diisopropylethylamine (0.54 g) and a solution of 3-(5-amino-pyrid-2-yl)propanoic acid ethyl ester [0.42 g, Reference Example 4(a)] in dimethylformamide (5 ml). After stirring at room temperature for 5 hours and standing over night the reaction mixture was evaporated. The residue was treated with ethyl acetate and the resulting solution was washed three times with water, then with brine and then evaporated. The residue was subjected to flash chromatography on silica gel eluting with a mixture of dichloromethane and methanol (97:3, v/v) to give the title compound (0.68 g) as a white foam.

(b) By proceeding in a manner similar to Reference Example 3(a) above but using 3-(5-amino-pyrid-2-yl)-2-methylpropanoic acid ethyl ester [Reference Example 4(b)] there was prepared 3-(5-{3-methoxy-4-[3-(2-methylphenyl) ureido]-phenylacetylamino}pyrid-2-yl)-2-methylpropanoic acid ethyl ester.

(c) By proceeding in a manner similar to Reference Example 3(a) above but using 3-(6-amino-pyrid-3-yl) propanoic acid ethyl ester [Reference Example 4(c)] there was prepared 3-(6-{3-methoxy-4-[3-(2-methylphenyl) ureido]-phenylacetylamino}pyrid-3-yl)propanoic acid ethyl ester.

Reference Example 4

(a) 3-(5-Amino-pyrid-2-yl)propanoic acid ethyl ester

A mixture of 3-(5-nitro-pyrid-2-yl)propenoic acid ethyl ester [0.8 g Reference Example 5(a)], ethanol (30 ml) and 5% palladium on charcoal (0.13 g) was stirred at ambient temperature under an atmosphere of hydrogen for 7 hours, left to stand over night and then stirred for a further 24 hours. The reaction mixture was filtered through a short pad of diatomaceous earth. The filtrate was evaporated to give the title compound (0.7 g) as a green oil.

(b) By proceeding in a manner similar to Reference Example 4(a) above but using 3-(5-nitro-pyrid-2-yl)-2-methylpropenoic acid ethyl ester [Reference Example 5(b)] there was prepared 3-(5-amino-pyrid-2-yl)-2-methylpropanic acid ethyl ester.

(c) By proceeding in a manner similar to Reference Example 4(a) above but using 3-(6-amino-pyrid-3-yl) propenoic acid ethyl ester [Reference Example 5(c)] there was prepared 3-(6-amino-pyrid-3-yl)propanoic acid ethyl ester.

Reference Example 5

(a) 3-(5-Nitro-pyrid-2-yl)propenoic acid ethyl ester

A mixture of 5-nitro-2-pyridinecarbaldehyde (2.85 g prepared according the procedure described in J. Med. Chem. 1992, 35, 3675) and (carbethoxymethylene) triphenylphosphorane (6.0 g) in dry toluene (120 ml) under nitrogen was stirred and heated at reflux for 6 hours. After standing at room temperature overnight the reaction mixture was evaporated. The residue was subjected to flash chromatography on silica gel eluting with dichloromethane to give the title compound (0.8 g) as a yellow solid.

(b) By proceeding in a manner similar to Reference Example 5(a) above but using (carbethoxyethylidene) triphenylphosphorane there was prepared 3-(5-nitro-pyrid-2-yl)-2-methylpropenoic acid ethyl ester.

(c) By proceeding in a manner similar to Reference Example 5(a) above but using 6-amino-3-pyridinecarbaldehyde (prepared in a similar manner to that described in Dolk. Akad. Nauk. SSSR. 1949, 65, 843) there was prepared 3-(6-amino-pyrid-3-yl)propenoic acid ethyl ester.

Reference Example 6

(a) (R)-3-(4-{3-methoxy-4-[3-(2-methylphenyl) ureido]phenylacetylamino}phenyl)-3-(methanesulphonylamino)-propanoic acid tert-butyl ester A mixture of (R)-3-amino-3-(4-{3-methoxy-4-[3-(2-methylphenyl)ureido]phenylacetylamino}-phenyl)-propanoic acid tert-butyl ester [100 mg, Reference Example 7(a)], dichloromethane (10 ml) and triethylamine (38 mg) was stirred at ambient temperature and then treated with methanesulphonyl chloride (22 mg). After stirring for 1 hour, the reaction mixture was diluted with dichloromethane (20 ml) and then washed with hydrochloric acid (20 ml, 1M), then with saturated aqueous sodium bicarbonate solution (20 ml). The organic layer was dried over magnesium sulphate and then evaporated to give the title compound (55 mg) as a white solid.

(b) By proceeding in a manner similar to Reference Example 6(a) but using 3-amino-3-(4-{3-methoxy-4-[3-(2-methylphenyl)ureido]phenylacetylamino}phenyl)-propanoic acid tert-butyl ester [Reference Example 7(b)] and acetyl chloride instead of methanesulphonylchloride there was prepared 3-(acetylamino)-3-(4-{3-methoxy-4-[3-(2-methylphenyl)ureido]phenylacetylamino}-phenyl)-propanoic acid tert-butyl ester.

(c) By proceeding in a manner similar to Reference Example 6(a) but using 3-amino-3-(4-{3-methoxy-4-[3-(2-methylphenyl)ureido]phenylacetylamino}phenyl)-propanoic acid tert-butyl ester [Reference Example 7(b)] and benzoyl chloride instead of methanesulphonylchloride there was prepared 3-(benzoylamino)-3-(4-{3-methoxy-4-[3-(2-methylphenyl)ureido]phenylacetylamino}-phenyl)-propanoic acid tert-butyl ester.

(d) By proceeding in a manner similar to Reference Example 6(a) but using 3-amino-3-(4-{3-methoxy-4-[3-(2-methylphenyl)ureido]phenylacetylamino}phenyl)-propanoic acid tert-butyl ester [Reference Example 7(b)] and pyridine-3-carbonyl chloride instead of methanesulphonylchloride there was prepared 3-(4-{3-methoxy-4-[3-(2-methylphenyl)ureido]phenylacetylamino}phenyl)-3-(pyridine-3-carbonylamino)-propanoic acid tert-butyl ester.

Reference Example 7

(a) (R)-3-Amino-3-(4-{3-methoxy-4-[3-(2-methylphenyl)ureido]phenylacetylamino}phenyl)-propanoic acid tert-butyl ester A suspension of 3-(4-{3-methoxy-4-[3-(2-methylphenyl)ureido]phenylacetylamino}-phenyl)-propanoic acid tert-butyl ester (1.0 g, Reference Example 8) in anhydrous tetrahydrofuran (50 ml) was treated with sodium hydride (0.23 g, 60% dispersion in mineral oil) and then stirred under an atmosphere of nitrogen for 30 minutes to produce a yellow solution. This solution was added dropwise to a solution of (S)-N-benzyl-α-methylbenzylamine (0.82 g) in anhydrous tetrahydrofuran (50 ml) was cooled to −78° C., under an atmosphere of nitrogen, treated with a solution of n-butyl lithium in hexanes (1.55 ml, 2.5M). After stirring a further 15 minutes at −78° C. the reaction mixture was poured into a mixture of ethyl acetate (200 ml) and saturated aqueous ammonium chloride solution (200 ml). The organic layer was separated, then dried over magnesium sulphate and then evaporated. The residue was subjected to flash chromatography on silica gel eluting with a mixture of ethyl acetate and dichloromethane (1:4, v/v) to give a yellow foam (840 mg). This material was dissolved in ethanol (50 ml), then treated with formic acid (3 ml) with warming to 60° C., then treated with 10% palladium on carbon (0.5 g). The mixture was stirred at 60° C. for 15 minutes then filtered through a short pad of diatomaceous earth. The filtrate was evaporated to low volume and the residue was partitioned between dichloromethane (50 ml) and saturated aqueous sodium bicarbonate solution (50 ml). The organic phase was dried over magnesium sulphate and then evaporated to give the title compound (360 mg) as a white solid.

(b) By proceeding in a manner similar to Reference Example 7(a) but using N,N-dibenzylamine instead of (S)-N-benzyl-(α-methylbenzylamine there was prepared 3-amino-3-(4-{3-methoxy-4-[3-(2-methylphenyl)ureido]phenylacetylamino}phenyl)-propanoic acid tert-butyl ester.

(c) By proceeding in a manner similar to Reference Example 7(a) but using 3-[4-(tert-butoxy-carbonylamino)phenyl]-propenoic acid methyl ester (Reference Example 35) instead of 3-(4-{3-methoxy-4-[3-(2-methylphenyl)ureido]phenylacetylamino}phenyl)-propenoic acid tert-butyl ester there was prepared (R)-3-amino-3-[4-(tert-butoxycarbonylamino)phenyl]-propanoic acid methyl ester.

(d) By proceeding in a manner similar to Reference Example 7(a) but using 3-[4-(tert-butoxycarbonylamino)phenyl]-propenoic acid methyl ester (Reference Example 35) instead of 3-(4-{3-methoxy-4-[3-(2-methylphenyl)ureido]phenylacetylamino}phenyl)-propenoic acid tert-butyl ester and (S)-N,α-dimethylbenzylamine instead of (S)-N-benzyl-α-methylbenzylamine there was prepared (R)-3-methylamino-3-[4-(tert-butoxycarbonylamino)phenyl]-propanoic acid methyl ester.

Reference Example 8

3-(4-{3-Methoxy-4-[3-(2-methylphenyl)ureido]phenylacetylamino}phenyl)-propenoic acid tert-butyl ester A mixture of 4-{3-methoxy-4-[3-(2-methylphenyl)ureido]phenylacetylamino}-iodobenzene [4.0 g, Reference Example 9(a)], palladium acetate (50 mg), tri-(o-tolyl)phosphine (125 mg) and tributylamine (1.85 g) in anhydrous dimethylformamide (10 ml) was treated with tert-butyl acrylate (1.0 g). The reaction mixture was stirred at 100° C. under an atmosphere of nitrogen for 4 hours then cooled to room temperature and then poured into a mixture of ethyl acetate (50 ml) and hydrochloric acid (50 ml, 1M). The resultant solid was filtered and washed sequentially with 50 ml portions of saturated aqueous sodium bicarbonate solution, water and diethyl ether. The residue was dried under vacuum to give the title compound (3.6 g) as a white solid.

Reference Example 9

(a) 4-{3-Methoxy-4-[3-(2-methylphenyl)ureido]phenylacetylamino}-iodobenzene

A mixture of 3-methoxy-4-[3-(2-methylphenyl)ureido]phenylacetic acid (2.9 g, Reference Example 31), 1-hydroxybenzotriazole (2.13 g), 1-(3-dimethylaminopropyl)-3-ethylcarbodiimide (2.67 g) and diisopropylethylamine (3.6 g) in anhydrous dimethylformamide (30 ml) was treated with 4-iodoaniline (2.43 g). After stirring at ambient temperature for 18 hours the reaction mixture was poured into a mixture of ethyl acetate (50 ml) and hydrochloric acid (50 ml, 1M). The resultant solid was filtered and then washed sequentially with 50 ml portions of saturated aqueous sodium bicarbonate solution, water and diethyl ether. The residue was dried under vacuum to give the title compound (4.05 g) as a light brown solid, m.p. >200° C.

(b) By proceeding in a manner similar to Reference Example 9(a) but using 4-[3-(2-methylphenyl)ureido]phenylacetic acid (2.9 g, prepared as described in Example 21 of International Patent Application Publication No. WO 96/22966) instead of 3-methoxy-4-[3-(2-methylphenyl)ureido]phenylacetic acid, there was prepared 4-{4-[3-(2-methylphenyl)ureido]-phenylacetylamino}-iodobenzene.

Reference Example 10

(a) 3-(n-Butylamino)-3-(4-{3-methoxy-4-[3-(2-methylphenyl)ureido]phenylacetylamino}-phenyl)-propanoic acid tert-butyl ester A mixture of 3-amino-3-(4-{3-methoxy-4-[3-(2-methylphenyl)ureido]phenylacetylamino}phenyl)-propanoic acid tert-butyl ester [53 mg, Reference Example 7(b)], butyraldehyde (14 mg), sodium acetate (16 mg) and 4 Å molecular sieves (0.2 g) in methanol (5 ml) was stirred at ambient temperature under an atmosphere of nitrogen and then treated with sodium cyanoborohydride (13 mg). After stirring for 1 hour the reaction mixture was treated dropwise with hydrochloric acid (0.5 ml, 1M) then poured into 10% aqueous potassium carbonate solution (10 ml). The mixture was extracted with ethyl acetate (30 ml). The organic phase was dried over magnesium sulphate and then evaporated. The residue was subjected to flash chromatography on silica gel eluting with ethyl acetate to give the title compound (44 mg) as a yellow foam.

(b) By proceeding in a manner similar to Reference Example 10(a) but using benzaldehyde instead of butyraldehyde there was prepared 3-benzylamino-3-(4-{3-methoxy-4-[3-(2-methylphenyl)ureido]phenylacetylamino}phenyl)-propanoic acid tert-butyl ester.

(c) By proceeding in a manner similar to Reference Example 10(a) but using phenylacetaldehyde instead of butyraldehyde there was prepared 3-(4-{3-methoxy-4-[3-(2-methylphenyl)ureido]phenylacetylamino}phenyl)-3-(2-phenylethylamino)-propanoic acid tert-butyl ester.

Reference Example 11

(a) 3-(4-{3-Methoxy-4-[3-(2-methylphenyl)ureido]phenylacetylamino}phenyl)-3-(morpholin-4-yl)-propanoic acid tert-butyl ester A solution of morpholine (87 mg) in anhydrous tetrahydrofuran (10 ml), cooled to −78° C. and under an atmosphere of nitrogen, was treated with a solution of n-butyl lithium in hexanes (0.4 ml, 2.5M). After stirring at −78° C. for 15 minutes the mixture was treated dropwise with a solution produced from treating a stirred suspension of 3-(4-{3-methoxy-4-[3-(2-methylphenyl)ureido]-phenylacetylamino}phenyl)-propenoic acid tert-butyl ester (0.25 g, Reference Example 8) in anhydrous tetrahydrofuran (10 ml) with sodium hydride (58 mg of a 60% dispersion in mineral oil), under an atmosphere of nitrogen. The resulting mixture was stirred a further 30 minutes at −78° C. then poured into a mixture of ethyl acetate (50 ml) and saturated aqueous sodium chloride solution (50 ml). The organic layer was separated, then dried over magnesium sulphate and then evaporated. The residue was triturated with diethyl ether to give the title compound (165 mg) as a white solid.

(b) By proceeding in a manner similar to Reference Example 11(a) but using N-methylpiperazine instead of morpholine there was prepared 3-(4-{3-methoxy-4-[3-(2-methylphenyl)ureido]phenylacetylamino}phenyl)-3-(4-methylpiperazin-1-yl)-propanoic acid tert-butyl ester.

Reference Example 12

(a) (R)-3-benzoylamino-3-(4-{3-methoxy-4-[3-(2-methylphenyl)ureido]-phenylacetyl-amino}-phenyl)-propanoic acid methyl ester A solution of 3-methoxy-4-[3-(2-methylphenyl)ureido]phenylacetic acid (1.52 g, prepared as described in Reference Example 31) in anhydrous dimethylformamide (40 ml), under an atmosphere of argon, was treated sequentially with O-(7-azabenzotriazol-1-yl)-1,1,3,3-tetramethyluronium hexafluorophosphate (1.84 g), diisopropylethylamine (3.4 ml) and a solution of (R)-3-benzoylamino-3-(4-aminophenyl)-propanoic acid methyl ester [2.0 g, Reference Example 13(a)] in dimethylformamide (10 ml). After stirring for 45 minutes at ambient temperature the reaction mixture was evaporated. The residue was treated with water (150 ml) and hydrochloric acid (10 ml, 1M) was added to the aqueous slurry. The mixture was filtered and the insoluble material was washed three times with water (50 ml) then dried in vacuo to give the title compound as white solid (2.53 g).

(b) By proceeding in a manner similar to Reference Example 12(a) but using (R)-3-acetylamino-3-(4-aminophenyl)-propanoic acid methyl ester [Reference Example 13(b)] there was prepared (R)-3-acetylamino-3-(4-{3-methoxy-4-[3-(2-methylphenyl)ureido]phenyl-acetylamino}phenyl)-propanoic acid methyl ester.

(c) By proceeding in a manner similar to Reference Example 12(a) but using (R)-3-benzyloxycarbonylamino-3-(4-aminophenyl)-propanoic acid methyl ester [Reference Example 13(c)] there was prepared (R)-3-benzyloxycarbonylamino-3-(4-{3-methoxy-4-[3-(2-methylphenyl)ureido]-phenylacetylamino}phenyl)-propanoic acid methyl ester.

(d) By proceeding in a manner similar to Reference Example 12(a) but using (R)-3-phenylsulphonylamino-3-(4-aminophenyl)-propanoic acid methyl ester [Reference Example 13(d)] there was prepared (R)-3-phenylsulphonylamino-3-(4-{3-methoxy-4-[3-(2-methylphenyl)-ureido]-phenylacetylamino}phenyl)-propanoic acid methyl ester.

(e) By proceeding in a manner similar to Reference Example 12(a) but using (R)-3-(pyridine-3-carbonylamino)-3-(4-aminophenyl)-propanoic acid methyl ester [Reference Example 13(e)] there was prepared (R)-3-(pyridine-3-carbonylamino)-3-(4-{3-methoxy-4-[3-(2-methylphenyl)-ureido]phenylacetylamino}phenyl)-propanoic acid methyl ester.

(f) By proceeding in a manner similar to Reference Example 12(a) but using (R)-3-(pyridine-3-sulphonylamino)-3-(4-aminophenyl)-propanoic acid methyl ester [Reference Example 13(f)] there was prepared (R)-3-(pyridine-3-sulphonylamino)-3-(4-{3-methoxy-4-[3-(2-methylphenyl)-ureido]phenylacetylamino}phenyl)-propanoic acid methyl ester.

(g) By proceeding in a manner similar to Reference Example 12(a) but using (R)-3-(N-acetyl-methylamino)-3-(4-aminophenyl)-propanoic acid methyl ester [Reference Example 13(g)] there was prepared (R)-3-(N-acetyl-methylamino)-3-(4-{3-methoxy-4-[3-(2-methylphenyl)ureido]-phenylacetylamino}phenyl)-propanoic acid methyl ester.

(h) By proceeding in a manner similar to Reference Example 12(a) but using (R)-3-(N-methanesulphonyl-methylamino)-3-(4-aminophenyl)-propanoic acid methyl ester [Reference Example 13(h)] there was prepared (R)-3-(N-methanesulphonyl-methylamino)-3-(4-{3-methoxy-4-[3-(2-methylphenyl)ureido]phenylacetylamino}phenyl)-propanoic acid methyl ester.

(i) By proceeding in a manner similar to Reference Example 12(a) but using (R)-3-[(5-methyl-isoxazole-3-carbonyl)-amino]-3-(4-aminophenyl)-propanoic acid methyl ester [Reference Example 13(i)] there was prepared (R)-3-[(5-methyl-isoxazole-3-carbonyl)-amino]-3-(4-{3-methoxy-4-[3-(2-methylphenyl)-ureido]phenylacetylamino}phenyl)-propanoic acid methyl ester.

(j) By proceeding in a manner similar to Reference Example 12(a) but using (R)-3-[(thiophene-2-carbonyl)-amino]-3-(4-aminophenyl)-propanoic acid methyl ester [Reference Example 13(j)] there was prepared (R)-3-[(thiophene-2-carbonyl)-amino]-3-(4-{3-methoxy-4-[3-(2-methylphenyl)-ureido]phenylacetylamino}phenyl)-propanoic acid methyl ester.

(k) By proceeding in a manner similar to Reference Example 12(a) but using (R)-3-[(4-methoxycarbonylbenzoyl)-amino]-3-(4-aminophenyl)-propanoic acid methyl ester (Reference Example 13(k)]

there was prepared (R)-3-[(4-methoxycarbonylbenzoyl)-amino]-3-(4-{3-methoxy-4-[3-(2-methylphenyl)-ureido] phenylacetylamino}phenyl)-propanoic acid methyl ester.

(l) By proceeding in a manner similar to Reference Example 12(a) but using (R)-3-[(3,4-dimethoxybenzoyl)-amino]-3-(4-aminophenyl)-propanoic acid methyl ester [Reference Example 13(l)] there was prepared (R)-3-[(3,4-dimethoxybenzoyl)-amino]-3-(4-{3-methoxy-4-[3-(2-methylphenyl)-ureido]phenylacetylamino}phenyl)-propanoic acid methyl ester.

(m) By proceeding in a manner similar to Reference Example 12(a) but using (R)-3-acetylamino-3-(4-aminophenyl)-propanoic acid methyl ester [Reference Example 13(b)] and 3-methylthio-4-[3-(2-methylphenyl) ureido]phenylacetic acid (Reference Example 15) there was prepared (R)-3-acetylamino-3-(4-{3-methylthio-4-[3-(2-methylphenyl)ureido]phenyl-acetylamino}phenyl)-propanoic acid methyl ester.

(n) By proceeding in a manner similar to Reference Example 12(a) but using (R)-3-acetylamino-3-(4-aminophenyl)-propanoic acid methyl ester [Reference Example 13(b)] and 3-methylsulphinyl-4-[3-(2-methylphenyl)ureido]phenylacetic acid [Reference Example 16(a)] there was prepared (R)-3-acetylamino-3-(4-{3-methylsulphinyl-4-[3-(2-methylphenyl)ureido]-phenylacetylamino}phenyl)-propanoic acid methyl ester.

(o) By proceeding in a manner similar to Reference Example 12(a) but using (R)-3-acetylamino-3-(4-aminophenyl)-propanoic acid methyl ester [Reference Example 13(b)] and 3-methylsulphonyl-4-[3-(2-methylphenyl)ureido]phenylacetic acid [Reference Example 16(b)] there was prepared (R)-3-acetylamino-3-(4-{3-methylsulphonyl-4-[3-(2-methylphenyl)ureido]-phenylacetylamino}phenyl)-propanoic acid methyl ester.

(p) By proceeding in a manner similar to Reference Example 12(a) but using (R)-3-[2-(2-methoxyethoxy) acetylamino]-3-(4-aminophenyl)-propanoic acid methyl ester [Reference Example 17 (a)] there was prepared (R)-3-[2-(2-methoxyethoxy)acetylamino]-3-(4-{3-methoxy-4-[3-(2-methylphenyl)-ureido]phenylacetylamino}phenyl)-propanoic acid methyl ester.

(q) By proceeding in a manner similar to Reference Example 12(a) but using (R)-3-[(tetrahydropyran-4-carbonyl)amino]-3-(4-aminophenyl)-propanoic acid methyl ester [Reference Example 17(b)] there was prepared (R)-3-[(tetrahydropyran-4-carbonyl)amino]-3-(4-{3-methoxy-4-[3-(2-methylphenyl)-ureido]phenylacetylamino}phenyl)-propanoic acid methyl ester.

(r) By proceeding in a manner similar to Reference Example 12(a) but using (R)-3-[(pyridazin-3-carbonyl)-amino]-3-(4-aminophenyl)-propanoic acid methyl ester [Reference Example 17(c)] there was prepared (R)-3-[(pyridazin-3-carbonyl)-amino]-3-(4-{3-methoxy-4-[3-(2-methylphenyl)-ureido]phenylacetylamino}phenyl)-propanoic acid methyl ester.

(s) By proceeding in a manner similar to Reference Example 12(a) but using (R)-3-[(pyridazin-3-carbonyl)-amino]-3-(4-aminophenyl)-propanoic acid methyl ester [Reference Example 17(c)] and 4-[3-(2-methylphenylureido)]-phenyl acetic acid (prepared as described in Example 21 of International Patent Application Publication No. WO 96/22966) there was prepared (R)-3-[(pyridazin-3-carbonyl)-amino]-3-(4-{4-[3-(2-methylphenyl)ureido]phenylacetyl-amino}phenyl)-propanoic acid methyl ester.

(t) By proceeding in a manner similar to Reference Example 12(a) but using (R)-3-(benzoylamino)-3-(4-aminophenyl)-propanoic acid methyl ester [Reference Example 13(a)] and 4-[3-(2-methylphenylureido)]-phenyl acetic acid (prepared as described in Example 21 of International Patent Application Publication No. WO 96/22966) there was prepared (R)-3-(benzoylamino)-3-(4-{4-[3-(2-methylphenyl)ureido]phenylacetylamino}phenyl)-propanoic acid methyl ester.

(u) By proceeding in a manner similar to Reference Example 12(a) but using (R)-3-[(4-methoxycarbonylbutanoyl)amino]-3-(4-aminophenyl)-propanoic acid methyl ester [Reference Example 18] and 4-[3-(2-methylphenylureido)]-phenyl acetic acid (prepared as described in Example 21 of International Patent Application Publication No. WO 96/22966) there was prepared (R)-3-[(4-methoxycarbonylbutanoyl)amino]-3-(4-{4-[3-(2-methylphenyl)ureido]phenylacetyl-amino}-phenyl)-propanoic acid methyl ester.

(v) By proceeding in a manner similar to Reference Example 12(a) but using 4-(4-aminophenyl)-tetrahydropyran-2-one (Reference Example 20) there was prepared 4-(4-{3-methoxy-4-[3-(2-methylphenyl)ureido] phenylacetylamino}phenyl)-tetrahydropyran-2-one.

(w) By proceeding in a manner similar to Reference Example 12(a) but using ethyl 3-[4-(N-methylamino) phenyl]-butanoate (Reference Example 33) there was prepared 3-[4-({3-methoxy-4-[3-(2-methylphenyl)ureido] phenylacetyl}-N-methylamino)phenyl]-butanoic acid ethyl ester.

(x) By proceeding in a manner similar to Reference Example 12(a) but using 3-(4-aminophenyl)-pentanedioic acid di-ethyl ester [Reference Example 36] there was prepared 3-(4-{3-methoxy-4-[3-(2-methylphenyl)ureido] phenylacetylamino}phenyl)-pentanedioic acid di-ethyl ester.

(y) By proceeding in a manner similar to Reference Example 12(a) but using (R)-3-[(4-carboxypyridine-3-carbonyl)-amino]-3-(4-aminophenyl)-propanoic acid di-methyl ester [Reference Example 17(d)] there was prepared (R)-3-[(4-carboxypyridine-3-carbonyl)-amino]-3-(4-{3-methoxy-4-[3-(2-methylphenyl)ureido]phenyl-acetylamino}phenyl)-propanoic acid di-methyl ester.

(z) By proceeding in a manner similar to Reference Example 12(a) but using (R)-3-[2,2-di-(hydroxymethyl) propanoyl-amino]-3-(4-aminophenyl)-propanoic acid methyl ester [Reference Example 17(e)] there was prepared (R)-3-[2,2-di-(hydroxymethyl)propanoyl-amino]-3-(4-{3-methoxy-4-[3-(2-methylphenyl)ureido]-phenylacetylamino}phenyl)-propanoic acid methyl ester (aa) By proceeding in a manner similar to Reference Example 12(a) but using (R)-3-[2-(4-methyl-piperazin-1-yl)-acetylamino]-3-(4-aminophenyl)-propanoic acid methyl ester [Reference Example 17(f)] there was prepared (R)-3-[2-(4-methyl-piperazin-1-yl)-acetylamino]-3-(4-{3-methoxy-4-[3-(2-methylphenyl)ureido]-phenylacetylamino}phenyl)-propanoic acid methyl ester.

(ab) By proceeding in a manner similar to Reference Example 12(a) but using (R)-3-[2-(carboxymethyloxy)-acetylamino]-3-(4-aminophenyl)-propanoic acid methyl ester [Reference Example 17(g)] there was prepared (R)-3-[2-(carboxymethyloxy)-acetylamino]-3-(4-{3-methoxy-4-[3-(2-methylphenyl)ureido]phenyl-acetylamino}phenyl)-propanoic acid di-methyl ester.

Reference Example 13

(a) (R)-3-benzoylamino-3-(4-aminophenyl)-propanoic acid methyl ester

A solution of (R)-3-amino-3-[4-(tert-butoxycarbonylamino)phenyl]-propanoic acid methyl ester

[3.0 g, Reference Example 7(c)] in dimethylformamide (50 ml), was treated with benzoyl chloride (1.24 ml) and triethylamine (1.56 ml). After stirring at ambient temperature for 2.25 hours, the mixture was evaporated to dryness and the resultant solid washed with water before being fried in vacuo. The resulting white solid (3.8 g) was dissolved in dichloromethane (70 ml) and the solution was treated with trifluoracetic acid (20 ml). After stirring at ambient temperature for 45 minutes, the reaction mixture was evaporated. The residue was treated with toluene (70 ml), concentrated to dryness and the resultant material treated with dichloromethane (200 ml). The resultant suspension was treated with saturated aqueous potassium carbonate solution (20 ml) with stirring at ambient temperature for 5 minutes. The organic layer was separated, dried over magnesium sulphate, and then evaporated to give the title compound as a white foam (2.0 g).

(b) (R)-3-acetylamino-3-(4-aminophenyl)-propanoic acid methyl ester

A solution of (R)-3-amino-3-[4-(tert-butoxycarbonylamino)phenyl]-propanoic acid methyl ester [7.2 g, Reference Example 7(c)] in dimethylformamide (30 ml), was treated with acetic anhydride (2.4 ml) and diisopropylethylamine (4.6 ml). After stirring at ambient temperature for 10 minutes the mixture was poured into water (500 ml) and then extracted twice with ethyl acetate (200 ml). The combined organic extracts were washed with brine (200 ml) then dried over magnesium sulphate and then evaporated. The resulting white foam (8.5 g) was dissolved in dichloromethane (75 ml) and the solution was treated with trifluoracetic acid (17 ml). After stirring at ambient temperature for 3 hours the reaction mixture was evaporated. The residue was treated with toluene (70 ml), concentrated to dryness and the resultant material treated with dichloromethane (200 ml). The resultant suspension was treated with saturated aqueous potassium carbonate solution (20 ml) with stirring at ambient temperature for 5 minutes. The organic layer was separated, dried over magnesium sulphate, and then evaporated to give the title compound (4.1 g) as a white foam.

(c) By proceeding in a manner similar to Reference Example 13(b) but using N-(benzyloxycarbonyloxy)succinimide instead of acetic anhydride there was prepared (R)-3-benzyloxycarbonylamino-3-(4-aminophenyl)-propanoic acid methyl ester.

(d) By proceeding in a manner similar to Reference Example 13(a) but using phenylsulphonylchloride instead of benzoyl chloride there was prepared (R)-3-phenylsulphonylamino-3-(4-aminophenyl)-propanoic acid methyl ester.

(e) By proceeding in a manner similar to Reference Example 13(a) but using pyridine-3-carbonyl chloride instead of benzoyl chloride there was prepared (R)-3-(pyridine-3-carbonylamino)-3-(4-aminophenyl)-propanoic acid methyl ester.

(f) By proceeding in a manner similar to Reference Example 13(a) but using pyridine-3-sulphonyl chloride (Reference Example, 14) instead of benzoyl chloride there was prepared (R)-3-(pyridine-3-sulphonylamino)-3-(4-aminophenyl)-propanoic acid methyl ester.

(g) By proceeding in a manner similar to Reference Example 13(b) but using (R)-3-methylamino-3-[4-(tert-butoxycarbonylamino)phenyl]-propanoic acid methyl ester [Reference Example 7(d)] instead of 3-amino-3-[4-(tert-butoxycarbonylamino)phenyl]-propanoic acid methyl ester there was prepared (R)-3-(N-acetyl-methylamino)-3-(4-aminophenyl)-propanoic acid methyl ester.

(h) By proceeding in a manner similar to Reference Example 13(a) but using (R)-3-methylamino-3-[4-(tert-butoxycarbonylamino)phenyl]-propanoic acid methyl ester [Reference Example 7(d)] instead of 3-amino-3-[4-(tert-butoxycarbonylamino)phenyl]-propanoic acid methyl ester and methanesulphonyl chloride instead of acetic anhydride there was prepared (R)-3-(N-methanesulphonyl-methylamino)-3-(4-aminophenyl)-propanoic acid methyl ester (i) By proceeding in a manner similar to Reference Example 13(a) but using 5-methylisoxazole-3-carbonyl chloride instead of benzoyl chloride there was prepared (R)-3-(5-methylisoxazole-3-carbonyl)amino-3-(4-aminophenyl)-propanoic acid methyl ester.

(j) By proceeding in a manner similar to Reference Example 13(a) but using 2-thiophene-carbonyl chloride instead of benzoyl chloride there was prepared (R)-3-(thiophene-2-carbonyl)amino-3-(4-aminophenyl)-propanoic acid methyl ester.

(k) By proceeding in a manner similar to Reference Example 13(a) but using 4-chlorocarbonyl-benzoic acid methyl ester instead of benzoyl chloride there was prepared (R)3-(4-methoxycarbonylbenzoyl)amino-3-(4-aminophenyl)-propanoic acid methyl ester.

(l) By proceeding in a manner similar to Reference Example 13(a) but using 3,4-dimethoxybenzoyl chloride instead of benzoyl chloride there was prepared (R)-3-[(3,4-dimethoxybenzoyl)-amino]-3-(4-aminophenyl)-propanoic acid methyl ester.

Reference Example 14

Pyridine-3-sulphonyl chloride

A mixture of pyridine-3-sulphonic acid (5.0 g), phosphorous pentachloride (8.0 g), phosphorous oxychloride (30 ml) and chloroform (30 ml) was stirred at 120° C. for 18 hours. The reaction mixture was cooled to room temperature then diluted with chloroform (30 ml) and then filtered. Hydrogen chloride gas was bubbled through the filtrate for 15 minutes and the resultant precipitate collected. This material was dried in vacuo to give the title compound as a white solid.

Reference Example 15

3-Methylthio-4-[3-(2-methylphenyl)ureido]phenylacetic acid

A stirred suspension of potassium tert-butoxide (16 g) in dry dimethylformamide (50 ml) was cooled to 0° C. and treated dropwise over 2 hours with a solution of methyl dichloroacetate (12 ml) and 2-methylthio-nitrobenzene (10.5 g, prepared according to the procedure described in J. Org. Chem. 1993, 21, 5628) in dimethylformamide (50 ml). After stirring for a further 1 hour, the mixture was warmed to ambient temperature and then quenched by the addition of water (10 ml) and hydrochloric acid (10 ml, 1M). The mixture was partitioned between ethyl acetate (600 ml) and hydrochloric acid (100 ml, 1M). The organic phase was separated then dried over magnesium sulphate and then evaporated. The residue was subjected to flash chromatography on silica gel eluting with a mixture of pentane and ether (7:3, v/v) to give a yellow solid (7.55 g). This material was dissolved in acetic acid (100 ml) and the solution was treated portionwise with zinc powder (16 g) then heated at reflux for 90 minutes. After cooling the mixture was filtered through a pad of diatomaceous earth. The filtrate was evaporated and the residue was dissolved in ethyl acetate (500 ml). The solution was washed three times with saturated sodium bicarbonate solution (100 ml) then three times with hydrochloric acid (100 ml, 1M). The pH of the combined hydrochloric acid washings was adjusted to 10 by addition of sodium hydroxide (3M). The solution was extracted three times with ethyl acetate (200 ml). The combined organic extracts were washed with brine (200 ml) then dried over magnesium sulphate and then evaporated. The residue was subjected to flash chromatography on silica gel eluting with a mixture of pentane and ether (80:20 v/v) to give a yellow oil (1.35 g). This material was treated with a solution of 2-methylphenyl isocyanate (0.8 ml) in ethyl acetate (30 ml) and the mixture was heated at reflux for 2 hours. After cooling the resultant precipitate was filtered and then dissolved in dichloromethane (100 ml). This solution was washed with hydrochloric acid (20 ml, 1M) then with brine (20 ml), then dried over magnesium sulphate and then evaporated to give the title compound (1.2 g) as a white solid.

Reference Example 16

(a) 3-Methylsulphinyl-4-[3-(2-methylphenyl)ureido]phenylacetic acid

A mixture of 3-methylthio-4-[3-(2-methylphenyl)ureido]phenylacetic acid (0.2 g, Reference Example 15), meta-chloroperbenzoic acid (61 mg) and methanol (25 ml) was stirred at ambient temperature for 1 hour and then evaporated. The residue was triturated with ethyl acetate to give the title compound (0.17 g) as a white solid.

(b) By proceeding in a manner similar to Reference Example 16(a) but using 3-methylsulphinyl-4-[3-(2-methylphenyl)ureido]phenylacetic acid [Reference Example 16(a)] there was prepared 3-methylsulphonyl-4-[3-(2-methylphenyl)ureido]phenylacetic acid.

Reference Example 17

(a) (R)-3-(2-methoxyethoxy)acetylamino-3-(4-aminophenyl)-propanoic acid methyl ester A mixture of (R)-3-amino-3-[4-(tert-butoxycarbonylamino)phenyl]-propanoic acid methyl ester [0.75 g, Reference Example 7(c)], 2-(2-methoxyethoxy)acetic acid (0.3 ml), O-(7-azabenzotriazol-1-yl)-1,1,3,3-tetramethyluronium hexafluorophosphate (1.02 g), diisopropylethylamine (0.9 ml) and dimethylformamide (25 ml) was stirred at ambient temperature 2 hours. The reaction mixture was poured into water (150 ml) and the resultant solid collected. The resulting fawn solid (1.5 g) was dissolved in dichloromethane (15 ml) and the solution was treated with trifluoracetic acid (3 ml). After stirring at ambient temperature for 2 hours the reaction mixture was evaporated. The residue was treated with toluene (50 ml), concentrated to dryness and the resultant material treated with ethyl acetate (50 ml). The resultant suspension was treated with saturated aqueous potassium carbonate solution (20 ml) with stirring at ambient temperature for 5 minutes. The organic layer was separated, dried over magnesium sulphate, and then evaporated to give the title compound (0.5 g) as a yellow oil.

(b) By proceeding in a manner similar to Reference Example 17(a) but using tetrahydropyran-4-carboxylic acid (prepared according to the procedure described in J. Med. Chem. 1994, Vol. 37(26), 4538–4553) instead of 2-(2-methoxyethoxy)acetic acid there was prepared (R)-3-[(tetrahydropyran-4-carbonyl)amino]-3-(4-aminophenyl)-propanoic acid methyl ester.

(c) By proceeding in a manner similar to Reference Example 17(a) but using pyridazine-3-carboxylic acid (prepared according to the procedure described in J. Het. Chem. 1975, Vol. 12(5), 957–961) instead of 2-(2-methoxyethoxy)acetic acid there was prepared (R)-3-[(pyridazin-3-carbonyl)-amino]-3-(4-aminophenyl)-propanoic acid methyl ester.

(d) By proceeding in a manner similar to Reference Example 17(a) but using 2-methoxycarbonylpyridine-5-carboxylic acid (Reference Example 38) instead of 2-(2-methoxyethoxy)acetic acid there was prepared (R)-3-[(4-carboxypyridine-3-carbonyl)-amino]-3-(4-aminophenyl)-propanoic acid di-methyl ester.

(e) By proceeding in a manner similar to Reference Example 17(a) but using 2,2-bis(hydroxymethyl)propionic acid instead of 2-(2-methoxyethoxy)acetic acid there was prepared (R)-3-[2,2-di-(hydroxymethyl)propanoyl-amino]-3-(4-aminophenyl)-propanoic acid methyl ester.

(f) By proceeding in a manner similar to Reference Example 17(a) but using 2-(4-methyl-piperazin-1-yl)acetic acid (Reference Example 39) instead of 2-(2-methoxyethoxy)acetic acid there was prepared (R)-3-[2-(4-methyl-piperazin-1-yl)-acetylamino]-3-(4-aminophenyl)-propanoic acid methyl ester.

(g) By proceeding in a manner similar to Reference Example 17(a) but using diglycolic acid mono-methyl ester (prepared by refluxing diglycolic anhydride in methanol) instead of 2-(2-methoxyethoxy)acetic acid there was prepared (R)-3-[2-(carboxymethyloxy)-acetylamino]-3-(4-aminophenyl)-propanoic acid methyl ester.

Reference Example 18

(R)-3-[(4-Methoxycarbonylbutanoyl)amino]-3-(4-aminophenyl)propanoic acid methyl ester Concentrated nitric acid (50 ml) was cooled to −30° C. and treated portionwise with (R)-3-(4-carboxybutanoylamino)-3-phenyl-propanoic acid (27 g, Reference Example 19). The resultant mixture was stirred at −30° C. for 30 minutes and then poured onto excess ice. The resultant solid was filtered and dried to yield a white solid (13 g). A portion of this material (15 g) was dissolved in methanol (375 ml) and the solution was treated with concentrated sulphuric acid (7.5 ml) then heated at reflux for 90 minutes. After cooling to room temperature the mixture was evaporated. The residue was dissolved in ethyl acetate (250 ml) and the solution was washed with water (200 ml), saturated aqueous sodium bicarbonate (200 ml) and brine (200 ml). The organic layer was dried over magnesium sulphate and then evaporated to give a white solid (16 g). A solution of this material in ethyl acetate (450 ml) was treated with 10% palladium on charcoal (2.5 g) and then stirred at ambient temperature for 3 hours under an atmosphere of hydrogen. The reaction mixture was filtered through a short pad of diatomaceous earth and the filtrate evaporated to give the title compound (15 g) as a pale yellow oil.

Reference Example 19

(R)-3-(4-Carboxybutanoylamino)-3-phenyl-propanoic acid

A solution of methyl (R)-3-amino-3-phenylpropanoic acid (10 g, prepared in a similar manner to the procedure described in Tetrahedron Letters 1972, 27, 2789–92) in dichloromethane (150 ml) was treated with methyl 4-(chloroformyl)butyrate (7.9 ml) followed by triethylamine (8.6 ml). The reaction was stirred at ambient temperature for 90 minutes and quenched by the addition of water (50 ml). The organic layer was washed with hydrochloric acid (1M), dried over magnesium sulphate, and evaporated to leave a white solid (17 g). A solution of this material in methanol (50 ml) was treated with sodium hydroxide (90 ml, 1M) and heated at 40° C. for 1 hour. After this time, the reaction was cooled, concentrated to low volume and acidified to pH 1.0 with concentrated hydrochloric acid. The resultant solid was collected, washed with water and dried to afford the title compound (6 g) as a white solid Reference Example 20

4-(4-Aminophenyl)-tetrahydropyran-2-one 3-phenylglutaric acid (23.3 g) was added to concentrated sulphuric acid (90 ml), at 10° C., and then the stirred mixture was treated dropwise with fuming nitric acid (4.7 ml) over 20 minutes ensuring the temperature of the reaction did not exceed 10° C. The resultant solution was stirred at ambient temperature for 1 hour and then poured onto excess ice. The resultant solid was collected and recrystallised from a mixture of toluene and cyclohexane to yield a light brown solid (27.1 g). A portion of this material (13.0 g) was suspended in acetic anhydride (70 ml) and the mixture was warmed to 85° C. After stirring at 85° C. for 150 minutes the mixture was cooled to room temperature and then evaporated. The residue was treated with toluene (100 ml) and the mixture was evaporated to give 3-(4-nitrophenyl)glutaric acid anhydride as a light brown solid (14.2 g). A portion of this material (10 g) was dissolved in tetrahydrofuran (50 ml) and the solution was added dropwise to a stirred, cooled (0° C.) suspension of sodium borohydride (1.77 g) in tetrahydrofuran (50 ml). The reaction mixture was then stirred at 0° C. for 4 hours then quenched by the dropwise addition of hydrochloric acid (70 ml, 6M). The mixture was extracted three times with ethyl acetate (200 ml). The combined extracts were dried over magnesium sulphate and then evaporated. The residue was treated with toluene (500 ml), then with p-toluenesulphonic acid (600 mg). The mixture was heated at reflux for 18 hours, then cooled to room temperature, then washed with saturated aqueous sodium bicarbonate solution (200 ml), and then evaporated. The residue was subjected to flash chromatography on silica gel eluting with a mixture of cyclohexane and ethyl acetate (2:3, v/v) to give a white solid (3.0 g). This material was dissolved in ethyl acetate (200 ml) and the solution was treated with 10% palladium on charcoal (0.35 g) and stirred at ambient temperature under an atmosphere of hydrogen for 18 hours. The reaction mixture was filtered through a short pad of diatomaceous earth and the filtrate was evaporated to give the title compound (2.5 g) as a white solid.

Reference Example 21

(R)-3-[(N-Acetyl-N-methyl)amino]-3-(4-{4-[3-(2-methylphenyl)ureido]phenylacetyl-N-methylamino}phenyl)-propionic acid tert-butyl ester (R)-3-[4-(N-benzyloxycarbonyl-N-methyl)aminophenyl]-3-[(N-acetyl-N-methyl)amino}propionic acid tert-butyl ester (1 g, Reference Example 22) was dissolved in a mixture of trifluoroacetic acid in dichloromethane (40 ml, 5%) at room temperature. After 2 hours the mixture was partitioned between dichloromethane and aqueous sodium bicarbonate solution. The organic layer was separated, then dried over magnesium sulphate and then evaporated. The residue was dissolved in dimethylformamide (5 ml) and added to a previously prepared mixture of 4-[3-(2-methylphenyl)ureido]-phenylacetic acid (74 mg), O-(7-azabenzotriazol-1-yl)-1,1,3,3-tetramethyluronium hexafluorophosphate (1.0 g), and diisopropylethylamine (670 mg) in dimethylformamide (15 ml). After stirring for 4 hours, the mixture was partitioned between ethyl acetate and aqueous hydrochloric acid (1M). The organic phase was washed with aqueous sodium bicarbonate solution, then dried over magnesium sulphate, and then evaporated. The residue was purified by flash chromatography on silica eluting with ethyl acetate to give the title compound (650 mg) as a colourless oil.

Reference Example 22

(R)-3-[4-(N-benzyloxycarbonyl-N-methyl)aminophenyl]-3-[(N-acetyl-N-methyl)amino}propionic acid tert-butyl ester (R)-3-[4-(N-benzyloxycarbonyl-N-methyl)aminophenyl]-3-(N-methylamino6)propionic acid tert-butyl ester (6 g, Reference Example 23) dissolved in a mixture of tetrahydrofuran (100 ml) and triethylamine (5.4 g) was treated dropwise with acetyl chloride (2.12 g), producing an immediate precipitate. The mixture was stirred for 30 minutes, then partitioned between ethyl acetate and aqueous hydrochloric acid (1M). The organic phase was separated, then washed with aqueous sodium bicarbonate solution, then dried over magnesium sulphate and then evaporated to give the title compound (6 g) as a light yellow oil.

Reference Example 23

(R)-(3-[4-(N-benzyloxycarbonyl-N-methyl)aminophenyl]-3-N-methylamino)propionic acid tert-butyl ester A solution of (R)-3-[4-(N-benzyloxycarbonyl-N-methyl)aminophenyl]-3-[N-((S)-alpha-methylbenzyl)methylamino]-propionic acid tert-butyl ester (6.5 g, Reference Example 24) in ethanol (50 ml), was heated to 60° C., then treated successively with formic acid (4 ml) and 10% palladium on charcoal (2 g). The mixture was stirred at 60° C. for 1 hour then cooled to room temperature, then filtered through filter-aid to remove the spent catalyst, and then evaporated. The residue was partitioned between ethyl acetate and aqueous sodium bicarbonate solution. The organicphase was dried over magnesium sulphate and then evaporated to give the title compound (6 g) as a colourless oil.

Reference Example 24

(R)-3-[4-(N-Benzyloxycarbonyl-N-methyl)aminophenyl]-3-[N-((S)-alpha-methylbenzyl)methylamino]propionic acid tert-butyl ester A solution of (S)-N-(alpha-methylbenzyl)methylamine (3.8 g) in tetrahydrofuran (60 ml) was cooled to less than −70° C. under a blanket of nitrogen, then treated with a solution of butyllithium in hexanes (11.3 ml, 2.5 M), keeping the temperature at or below −60° C. Ten minutes after the addition was complete a solution of 3-[4-(N-benzyloxycarbonyl-N-methyl)aminophenyl]acrylic acid tert-butyl ester (4.7 g, Reference Example 25) in tetrahydrofuran (40 ml) was added slowly over 20 minutes. After a further 20 minutes at below −70° C. the cold reaction mixture was poured directly into a mixture of ethyl acetate and brine, then the layers were separated and the organic phase was dried over magnesium sulphate and then evaporated. The residue was subjected to flash chromatography on silica eluting with a mixture of ethyl acetate and cyclohexane mixture (3:7, v/v) to give the title compound (5.5 g) as a colourless oil.

Reference Example 25

3-[4-(N-Benzyloxycarbonyl-N-methyl)aminophenyl] acrylic acid tert-butyl ester

N-Benzyloxycarbonyl-N-methyl-4-iodoaniline (11 g, Reference Example 26), tert-butyl acrylate (8.4 g), tris-[(2-tolyl)phosphine] (0.5 g) and palladium acetate (0.15 g) were dissolved in a mixture of dimethylformamide (20 ml) and triethylamine (7.1 g) and stirred at 90° C. under nitrogen overnight. The reaction mixture was partitioned between ethyl acetate and aqueous hydrochloric acid (1M). The organic phase was washed with aqueous sodium bicarbonate solution (5%), then dried over magnesium sulphate, and then evaporated. The residue was recrystallised from cyclohexane to give the title compound (7.4 g) as an off-white solid.

Reference Example 26

N-Benzyloxycarbonyl-N-methyl-4-iodoaniline

A stirred solution of N-benzyloxycarbonyl-4-iodoaniline (11.5 g, Reference Example 27) in dimethylformamide (70 ml) was treated portionwise with sodium hydride (⅙ g of a 60% dispersion in oil), under nitrogen and at room temperature. When effervescence had ceased methyl iodide (6.3 g) was added and the mixture was stirred at room temperature for 2 hours, after which it was partitioned between ethyl acetate and water. The organic phase was separated, then dried over magnesium sulphate and then evaporated to give the title compound (11.5 g) as a pink oil.

Reference Example 27

N-Benzyloxycarbonyl-4-iodoaniline

A solution of 4-iodoaniline (10 g) in tetrahydrofuran (100 ml) was treated with benzyloxycarbonyl-anhydride (12 g) in one portion. The mixture was stirred at reflux overnight, then evaporated to low bulk. The residue was partitioned between ethyl acetate and aqueous hydrochloric acid (1M). The organic phase was washed with aqueous sodium bicarbonate solution (5%), then dried over magnesium sulphate, and then evaporated. The residue was recrystallised from cyclohexane to give the title compound (12.4 g) as light purple crystals.

Reference Example 28

(a) (R)-3-(4-Carboxybutanoylamino)-3-(4-{3-methoxy-4-[3-(2-methylphenyl)ureido] phenylacetylamino}phenyl)-propanoic acid methyl ester A stirred suspension of (R)-3-amino-3-(4-{3-methoxy-4-[3-(2-methylphenyl)ureido]-phenylacetylamino}phenyl)-propanoic acid methyl ester (0.75 g, Reference Example 30) in anhydrous tetrahydrofuran (25 ml), under an atmosphere of argon, was treated with glutaric anhydride (0.18 g). After stirring at ambient temperature for 4 hours the reaction mixture was evaporated to give the title compound (1.0 g) as a white solid.

(b) By proceeding in a manner similar to Reference Example 28(a) but using succinic anhydride instead of glutaric anhydride, there was prepared (R)-3-(3-carboxypropanoylamino)-3-(4-{3-methoxy-4-[3-(2-methylphenyl)ureido]phenylacetylamino}phenyl)-propanoic acid methyl ester.

(c) By proceeding in a manner similar to Reference Example 28(a) but using 3,3-dimethylglutaric anhydride instead of glutaric anhydride, there was prepared (R)-3-[(4-carboxy-3,3-dimethyl-butanoyl)amino]-3-(4-{3-methoxy-4-[3-(2-methylphenyl)ureido]-phenylacetylamino}phenyl)-propanoic acid methyl ester.

Reference Example 29

(a) (R)-3-(5-Dimethylamino-1-naphthalenesulphonylamino)-3-(4-{3-methoxy-4-[3-(2-methylphenyl)ureido] phenylacetylamino}phenyl)-propanoic acid methyl ester A mixture of (R)-3-amino-3-(4-{3-methoxy-4-[3-(2-methylphenyl)ureido]phenylacetylamino}-phenyl)-propanoic acid methyl ester (0.75 g, Reference Example 30), anhydrous tetrahydrofuran (25 ml), dansyl chloride (0.62 g) and triethylamine (1.0 ml) was placed under an atmosphere of argon and stirred at ambient temperature for 4 hours then heated to reflux for 2 hours. The reaction mixture was cooled then filtered. The filtrate was evaporated and the residue was subjected to flash chromatography on silica gel eluting with a mixture of dichloromethane and methanol (49: 1, v/v to give the title compound (0.89 g) as a yellow solid.

(b) By proceeding in a manner similar to Reference Example 29(a) but using 1-methylimidazole-4-sulphonyl chloride instead of dansyl chloride, there was prepared (R)-3-(1-methylimidazol-4-ylsulphonylamino)-3-(4-{3-methoxy-4-[3-(2-methylphenyl)ureido]-phenylacetylamino}phenyl)-propanoic acid methyl ester.

Reference Example 30

(R)-3-Amino-3-(4-{3-methoxy-4-[3-(2-methylphenyl)ureido]phenylacetylamino}phenyl)-propanoic acid methyl ester A mixture of (R)-3-benzyloxycarbonylamino-3-(4-{3-methoxy-4-[3-(2-methylphenyl)ureido]-phenylacetylamino}phenyl)-propanoic acid methyl ester (18.55 g), ethanol (750 ml) and formic acid (18 ml), under an atmosphere of hydrogen, was heated at reflux. The reaction was treated portionwise with 10% palladium on charcoal (3.0 g) over a period of 1 hour and then heated at reflux for a further 1 hour. The reaction mixture was filtered through a short pad of diatomaceous earth and the filter pad was washed three times with ethanol (75 ml) and water (75 ml). The combined filtrate and washings were evaporated. The residue was treated carefully with aqueous solution of sodium bicarbonate (600 ml, 0.6M) followed by stirring for 15 minutes. The resultant white solid was collected, washed twice with water (100 ml), then boiled in acetonitrile in the presence of activated charcoal (150 mg). The mixture was filtered through a short pad of diatomaceous earth while hot and the filtrate cooled in ice to yield the title compound (7.6 g) as a white solid m.p. 189–191° C.

Reference Example 31

3-Methoxy-4-[3-(2-methylphenyl)ureido] phenylacetic acid

A suspension of 3-methoxy-4-[3-(2-methylphenyl) ureido]phenylacetic acid methyl ester (19.43 g, Reference Example 32) in methanol (195 ml) was treated with sodium hydroxide solution (65 ml, 1N) and the mixture was heated at reflux for 1 hour giving a clear solution. The reaction mixture was cooled to room temperature and filtered. The filtrate was diluted to 390 ml with water, then heated to 50° C. and then acidified to pH 1 by the addition of hydrochloric acid (80 ml, 1N) over 1 hour. The resulting suspension was stirred for a further 30 minutes at 50° C., then allowed to cool to room temperature and then filtered. The solid was washed with twice with water (200 ml) then dried to give the title compound (15.72 g) as a white solid, m. p. 179–181° C. (with decomposition).

Reference Example 32

3-methoxy-4-[3-(2-methylphenyl)ureido] phenylacetic acid methyl ester

A suspension of potassium t-butoxide (1.44 kg) in dimethylformamide(6.61) cooled to −5° C. to −10° C., was treated with a mixture of 2-nitroanisole (690 g) and methyl dichloroacetate (915 g) over 4 hours, whilst maintaining the temperature below −5° C. The reaction mixture was then treated with acetic acid (770 ml) and then with water (6.61) and then e extracted three times with tert-butyl methyl ether (5.51). The combined extracts were washed with water (5.51), then with saturated sodium bicarbonate solution (5.51), then with saturated brine (5.51) and then dried over magnesium sulphate to give a solution of methyl α-chloro-3-methoxy-4-nitrophenylacetate.

This solution was concentrated to half volume under reduced pressure and then treated with tetrahydrofuran (21), followed by triethylamine (751 ml), followed by 10% palladium on charcoal (58.4 g) and the mixture was hydrogenated under a pressure of 50 psi hydrogen at 50° C. for 8 hours. The mixture was cooled to room temperature and filtered. The filtrate was dried over magnesium sulphate to give a solution of methyl 4-amino-3-methoxyphenylacetate which was heated to reflux then treated with o-tolyl isocyanate (598.5 g) over 30 minutes. After heating at reflux temperature for a further 3 hours, during which time a solid was deposited, the mixture was cooled to room temperature. The solid was collected, washed twice with tert-butyl methyl ether (41), then dried in a vacuum oven at 60° C. to give the title compound (764.8 g) as a white solid, m.p. 167–168° C.

Reference Example 33

Ethyl 3-[4-(N-methylamino)phenyl]-butanoate

A mixture of (E)-ethyl 3-methyl-3-(4-nitrophenyl)-propenoate (11.5 g, prepared in a similar manner to that described in J. Med Chem. 1968, 11, 672), ethanol (200 ml), acetic acid (200 ml) and 10% palladium on charcoal (1 g) was stirred at ambient temperature under an atmosphere of hydrogen (2 bar) for 6 hours. The reaction mixture was filtered through a short pad of diatomaceous earth. The filtrate was evaporated and the residue was subjected to flash chromatography on silica gel eluting with a mixture of pentane and ethyl acetate (4:1, v/v) to leave a yellow oil (6.5 g). A portion of this material (3.0 g) was dissolved in tetrahydrofuran (20 ml) and the solution was added dropwise to methanoic ethanoic anhydride [previously prepared by mixing 90% formic acid (2.4 g) and acetic anhydride (3.8 g) before heating the mixture to 55° C. and then cooling to ambient temperature). The mixture was stirred at ambient temperature for 18 hours and then evaporated to give an oil (3.5 g). A stirred solution of this oil in tetrahydrofuran (20 ml), under an atmosphere of nitrogen, was treated dropwise with a solution of borane dimethyl sulphide complex in tetrahydrofuran (3.7 ml, 1M) and then the mixture was heated at reflux for 90 minutes. The reaction mixture was cooled, treated with methanol (2 ml) and then stirred at ambient temperature for 30 minutes. The pH of the mixture was adjusted to 2.0 by addition of concentrated hydrochloric acid, then the mixture was heated at reflux for 1 hour. The reaction mixture was poured into 10% aqueous potassium carbonate solution (100 ml) and then extracted three times with ethyl acetate (100 ml). The combined extracts were dried over magnesium sulphate and then evaporated. The residue was subjected to flash chromatography on silica gel eluting with a mixture of pentane and ethyl acetate (4:1, v/v) to give the title compound as a white solid (0.15 g).

Reference Example 34

3-(4-{3-Methoxy-4-[3-(2-methylphenyl)ureido] phenylacetylamino}phenyl)-pentanedioic acid A mixture of 3-(4-{3-methoxy-4-[3-(2-methylphenyl)ureido]phenylacetylamino}phenyl)-pentanedioic acid di-ethyl ester [8.40 g, Reference Example 12(x)] and methanol (400 ml) was heated to 40° C. and then treated with 10% aqueous sodium hydroxide solution (110 ml). After stirring at 40° C. for 1 hour, the reaction mixture was cooled and then acidified to pH 1.0 by addition of hydrochloric acid (1M). The resultant white solid was collected, washed with water and then dried in vacuo. Recrystallisation from ethanol gave the title compound as a white crystalline solid (4.7 g), m.p. 218–220° C. [Elemental analysis:—C, 64.5; H, 5.6; N, 7.9%. Calculated for $C_{28}H_{29}N_3O_7$:—C, 64.7; H, 5.6; N, 8.1%].

Reference Example 35

(3)-[4-(tert-Butoxycarbonylamino)phenyl]-propenoic acid methyl ester

A solution of 4-amino-cinnamic acid hydrochloride (50 g) in water (800 ml) was treated with sodium carbonate (33.2 g) followed by a solution of di-(tert-butoxy)carbonate (77.5 ml) in tetrahydrofuran (300 ml). The reaction mixture was stirred at ambient temperature for 18 hours and concentrated to low volume (500 ml). This mixture was acidified to pH 2.0 by addition of concentrated hydrochloric acid and then extracted twice with ethyl acetate (500 ml). The combined organic extracts were washed twice with water (500 ml), then with brine (500 ml), then dried over magnesium sulphate and then evaporated. The residual white solid (47 g) was dissolved in dimethylformamide (240 ml) and the solution stirred then treated sequentially with potassium carbonate (24.8 g) and methyl iodide (11.2 ml). After stirring at ambient temperature for a further 2 hours the reaction mixture was evaporated. The residue was treated with water (500 ml) then filtered. The resultant solid was washed with water (200 ml), then with 10% aqueous potassium carbonate (200 ml), then with water (200 ml) and then dried in vacuo to give the title compound as a white solid (46.5 g).

Reference Example 36

3-(4-Aminophenyl)-pentanedioic acid di-methyl ester

Concentrated sulphuric acid (100 ml) was cooled to 10° C. and then treated with 3-phenylglutaric acid (24 g). The stirred mixture was then treated dropwise with fuming nitric acid (5 ml) over 20 minutes ensuring the temperature of the reaction did not exceed 10° C. The resultant solution was stirred at ambient temperature for 1.5 hours and then poured onto excess ice. The resultant solid was collected and washed with water. The residue was triturated with acetonitrile (100 ml) and dried in vacuo to leave a white solid (26.5 g). This material was dissolved in methanol (900 ml) and the solution was treated with concentrated sulphuric acid (1.0 ml) and then heated at reflux for 4 hours. After cooling to room temperature the mixture was evaporated to dryness. The residue was treated with saturated aqueous sodium bicarbonate (100 ml) and the resultant solid collected and washed with water. This was recrystallised from diisopropyl ether to leave a colourless solid (14 g). A solution of this material in ethyl acetate (550 ml) was treated with 10% palladium on charcoal (1.4 g) and then stirred at ambient temperature for 4 hours under an atmosphere of hydrogen. The reaction mixture was filtered through a short pad of diatomaceous earth and the filtrate evaporated to give the title compound as a colourless solid (2.33 g).

Reference Example 37

(a) (R)-3-[(morpholin-1yl)-acetylamino]-3-(4-{3-methoxy-4-[3-(2-methylphenyl)ureido]-phenyl-acetylamino}phenyl)-propanoic acid methyl ester A mixture of (R)-3-amino-3-(4-{3-methoxy-4-[3-(2-methylphenyl)ureido]-phenylacetylamino}phenyl)-propanoic acid methyl ester (1.0 g, Reference Example 30); (morpholin-1-yl)acetic acid (0.33 g, prepared according to the procedure described in Zh. Obshch. Khim 1953, 23, 794); O-(7-azabenzotriazol-1-yl)-1,1,3,3-tetramethyluronium hexafluorophosphate (0.76 g); diisopropylethylamine (1.1 ml) and dimethylformamide (6 ml) was stirred at ambient temperature for 2 hours. The reaction mixture was then poured into water (150 ml). The resulting solid was dried in vacuo to give the title compound as a green solid (1.31 g).

(b) By proceeding in a manner similar to Reference Example 37(a) but using N-(tert-butoxycarbonylmethyl)isonipecotic acid [prepared by sodium hydroxide hydrolysis of N-(tert-butoxycarbonylmethyl)isonipecotic acid ethyl ester (J. Med. Chem. 1982, Vol 25(3), 256)] instead of (morpholin-1-yl)acetic acid, there was prepared (R)-3-[(1-tert-butoxycarbonylmethyl-piperidin-4-carbonyl)-amino]-3-(4-{3-methoxy-4-[3-(2-methylphenyl)ureido]phenylacetyl-amino}phenyl)-propanoic acid methyl ester.

Reference Example 38

2-Methoxycarbonylpyridine-5-carboxylic acid

A mixture of pyridine-2,5-dicarboxylic acid (8.4 g), methanol (100 ml) and concentrated sulphuric acid (1.7 ml) was heated at reflux for 2 hours, cooled and poured into water (11). The resultant precipitate was collected and recrystallised from ethanol to give the title compound as a white solid, m.p. 222–223° C.

Reference Example 39

2-(4-Methyl-piperazin-1-yl)-acetic acid

A mixture of 1-methylpiperazine (10.7 g), benzylbromoacetate (24 g), triethylamine (28 ml) and dichloromethane (100 ml) was stirred at ambient temperature for 4 hours. The reaction was concentrated to dryness, taken up in tetrahydrofuran (100 ml), filtered, and the filtrate evaporated to dryness. The residue was taken up in methanol (100 ml), treated with aqueous sodium hydroxide solution (100 ml, 1M) and stirred at reflux for 24 hours. The reaction was concentrated to dryness, diluted with water (100 ml) and then acidified to pH6.0 by addition of concentrated hydrochloric acid. The mixture was evaporated.. A portion of the resulting brown oil (2.0 g) was taken up in water (100 ml), treated with Dowex 50WX8 resin (80 g) and stirred at ambient temperature for 10 minutes. The mixture was filtered and the resin washed with water until the washings were neutral. The resin was then stirred with 2.0M aqueous ammonia (3×100 ml) for 5 minutes and filtered. The combined ammonia washings were concentrated to leave the title compound as a white waxy solid (0.8 g).

IN VITRO AND IN VIVO TEST PROCEDURES

1. Inhibitory Effects of Compounds on VLA4 Dependent Cell Adhesion to Fibronectin and VCAM 1.1 Metabolic Labelling of RAMOS Cells RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 $\mu$Ci/100 mls of [$^3$H]-methionine (Amersham, UK) for 18 hours at 37° C.

1.2 96 Well Plate Preparation for Adhesion Assay

Cytostar plates (Amersham, UK) were coated with 50 $\mu$l/well of either 3 $\mu$g/ml human soluble VCAM-1 (R&D Systems Ltd, UK) or 28.8 $\mu$g/ml human tissue Fibronectin (Sigma, UK). In control non-specific binding wells 50 $\mu$l phosphate buffered saline was added. The plates were then left to dry in an incubator at 25° C., overnight. The next day the plates were blocked with 200 $\mu$l/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 $\mu$l/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 $\mu$l/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 $\mu$l/well of cells in 3.6% dimethyl sulphoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Particular compounds of the invention inhibit cell adhesion to fibronectin and VCAM-1 with IC50s in the range 100 micromolar to 0.01 nanomolar. Preferred compounds of the invention inhibit cell adhesion to fibronectin and VCAM-1 with $IC_{50}$s in the range 1.0 micromolar to 0.01 nanomolar. Especially preferred compounds of the invention inhibit cell adhesion to fibronectin and VCAM-1 with $IC_{50}$s in the range 10 nanomolar to 0.01 nanomolar.

2. Inhibition of Antigen-induced Airway Inflammation in the Mouse and Rat 2.1 Sensitization of the Animals Rats (Brown Norway, Harland Olac, UK) are sensitized on days 0, 12 and 21 with ovalbumin (100 μg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 μg, i.p.) administered with aluminium hydroxide adjuvant (20 mg, i.p.) in saline (0.2 ml, i.p.).

2.2 Antigen Challenge

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5 % methyl cellulose/0.2 % polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg, i.t.

2.4 Assessment of Airway Inflammation

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640 FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK)

2.5 Data Analysis

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where p<0.05 no statistical significance existed.

The inhibitors of the invention caused a statistically significant reduction in eosinophil and lymphocyte numbers in the BAL and airway tissue at doses within the range 100 mg/kg to 0.01 mg/kg.

3. Inhibition of Antigen Induced Airway Sensitivity in Allergic Sheep

The experiment was performed essentially as described in W. M. Abraham et al, J. Clin. Invest., (1994) Vol 93, 776–787. The experiment used allergic sheep which had been previously shown to develop early and late phase responses to inhaled challenge with Ascaris suum antigen. The inhibitors of the invention were delivered as an aerosol to the sheep and caused a statistically significant reduction of Ascaris suum induced airway responses.

What is claimed is:

1. A compound of formula (I):

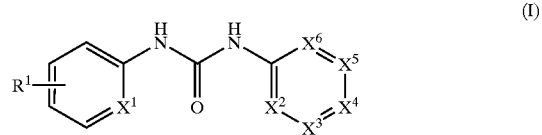

wherein:

$R^1$ is hydrogen, halogen, hydroxy, lower alkyl or lower alkoxy;

$X^1$, $X^2$ and $X^6$ independently represent N or $CR^{10}$; and one of $X^3$, $X^4$ and $X^5$ represents $CR^{11}$ and the others independently represents N or $CR^{10}$;

$R^{10}$ is hydrogen, amino, halogen, hydroxy, lower alkyl, lower alkoxy, lower alkylthio, lower alkylsulphinyl, lower alkylsulphonyl, nitro or trifluoromethyl;

$R^{11}$ represents a group —$L^1$—$Ar^1$—$L^2$—Y;

$L^1$ represents a —$R^2$—$R^3$— linkage;

$R^2$ is a straight or branched $C_{1-6}$alkylene chain, a straight or branched $C_{2-6}$alkenylene chain or a straight or branched $C_{2-6}$alkynylene chain;

$R^3$ is a direct bond, cycloalkylene, heterocycloalkylene, arylene, heteroaryldiyl, —C(=Z)—$NR^4$—, —$NR^4$—C(=Z)—, —$Z^1$—, —C(=O)—, —C(=$NOR^4$)—, —$NR^4$—C(=Z)—$NR^4$—, —$SO_2$—$NR^4$—, —$NR^4$—$SO_2$—, —O—C(=O)—, —C(=O)—O—, —$NR^4$—C(=O)—O— or —O—C(=O)—$NR^4$—;

$R^4$ is a hydrogen atom or a lower alkyl group;

Z is O or S;

$Z^1$ is O, $S(O)_n$ or $NR^4$;

n is zero or an integer 1 or 2;
provided that an oxygen, nitrogen or sulphur atom in $R^3$ is not attached directly to a carbon carbon multiple bond in $R^2$;
$Ar^1$ is arylene or heteroaryldiyl;
$L^2$ represents:
 (i) a direct bond;
 (ii) an alkylene, alkenylene, alkynylene, cycloalkenylene, cycloalkylene, heteroaryldiyl, heterocycloalkylene or arylene linkage each optionally substituted by (a) carboxy, $R^5$, —ZH, —$ZR^5$, —C(=O)—$R^5$, —N($R^{12}$)—C(=O)—$R^{13}$, —N($R^{12}$)—C(=O)—$OR^{13}$, —N($R^{12}$)—$SO_2$—$R^{13}$, —$NY^1Y^2$, or —[C(=O)—N($R^6$)—C($R^4$)($R^7$)]$_p$—C(=O)—$NY^1Y^2$, or by (b) alkyl substituted by carboxy, imidazolyl, —ZH, —$ZR^5$, —C(=O)—$NY^1Y^2$ or —$NY^1Y^2$;
 (iii) a —[C(=O)—N($R^6$)—C($R^4$)($R^7$)]$_p$— linkage;
 (iv) a —$Z^2$—$R^9$— linkage;
 (v) a —C(=O)—$CH_2$—C(=O)— linkage;
 (vi) a —$R^9$—$Z^2$—$R^9$— linkage; or
 (vii) a —C($R^4$)($R^8$)—[C(=O)—N($R^6$)—C($R^4$)($R^7$)]$_p$— linkage;
$R^5$ is alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl, or heterocycloalkylalkyl;
$R^6$ is hydrogen, $R^5$ or alkyl substituted with alkoxy, cycloalkyl, hydroxy, mercapto, alkylthio or —$NY^1Y^2$;
$R^7$ and $R^8$ are each independently selected from hydrogen or a group consisting amino acid side chains and corresponding protected derivatives, carboxy, $R^5$, —ZH, —$ZR^5$, —C(=O)—$R^5$, or —C(=O)—$NY^1Y^2$, or alkyl substituted by carboxy, —ZH, —$ZR^5$, —$NY^1Y^2$, —NH—C(=O)—$R^5$, —C(=O)—$R^2$—$NH_2$, —C(=O)—$Ar^1$—$NH_2$, —C(=O)—$R^2$—$CO_2H$, or —C(=O)—$NY^1Y^2$;
or $R^6$ and $R^7$ or $R^6$ and $R^8$ together with the atoms to which they attached form a 3- to 6-membered heterocycloalkyl ring;
$R^9$ is $C_{1-6}$alkylene, optionally substituted by $R^5$;
$R^{12}$ is hydrogen, alkyl, aryl, arylalkyl, cycloalkyl, cycloalkylalkyl, heteroaryl, heteroarylalkyl, heterocycloalkyl or heterocycloalkylalkyl;
$R^{13}$ is alkyl, aryl, cycloalkyl, heteroaryl or heterocycloalkyl, or alkyl substituted by aryl, carboxy, cycloalkyl, heteroaryl, heterocycloalkyl, —ZH, —$ZR^5$, —C(=O)—$NY^1Y^2$ or —$NY^1Y^2$;
$Y^1$ and $Y^2$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^1Y^2$, or one or more —$CO_2R^{12}$ or —C(=O)—$NY^1Y^2$ groups; or the group —$NY^1Y^2$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), $R^{13}$; (ii) may also contain a further heteroatom selected from O, S, $SO_2$, or $NY^3$; and (iii) may also be fused to additional aryl, heteroaryl, heterocycloalkyl or cycloalkyl rings to form a bicyclic or tricyclic ring system;
$Y^3$ is hydrogen, alkyl, aryl, arylalkyl, —C(=O)—$R^{14}$, —C(=O)—$OR^{14}$ or —$SO_2R^{14}$ (in which $R^{14}$ is alkyl, aryl, arylalkyl, cycloalkyl, cycloalkylalkyl, heteroaryl, heteroarylalkyl, heterocycloalkyl or heterocycloalkylalkyl;
$Z^2$ is O, S(O)$_n$, $NR^4$, $SONR^4$, C(=O)$NR^4$ or C(=O); and
p is zero or an integer 1 to 4; and
Y is carboxy, an acid bioisostere, or —C(=O)—$NY^1Y^2$;
and the corresponding N-oxides, and their ester prodrugs; and pharmaceutically acceptable salts and solvates of such compounds and their N-oxides and ester prodrugs; but excluding the compounds (2-{2-[4-(3-(2-methylphenyl)ureido)-phenyl]-acetylamino}-thiazol-4-yl)-acetic acid, 2-phenylacetylamino-3-{4-[4-(3-(2-methylphenyl)ureido)-benzyloxy]-phenyl}-propionic acid, 2-phenylacetylamino-3-(4{2-[4-(3-(2-methylphenyl)ureido)-phenyl]-ethoxy}-phenyl)-propionic acid, 2-benzylsulphonylamino-3-{4-[4-(3-(2-methylphenyl)ureido)-benzyloxy]-phenyl}-propionic acid, (butane-1-sulphonylamino)-{2-[4-(3-(2-methylphenyl)-ureido)-benzyl]-benzofuran-6-yl}-acetic acid, 3-(benzylaminocarbonyl)-(4{2-[4-(3-(2-methylphenyl)ureido)-phenyl]-ethoxy}-benzyl)-propionic acid and 2-benzyloxycarbonylamino-3-(5-{3-[4-(3-(2-methylphenyl)ureido)-phenyl]-propyl}-thiophene-2-yl)-propionic acid; and with the proviso that $L^1$ cannot represent $C_{1-6}$alkylene-C(=O)—NH— or $C_{1-6}$alkylene when $Ar^1$ represents optionally substituted phenylene, Y represents —$CO_2H$, —$SO_3H$, —$PO_4H_2$ or tetrazole, and $L^2$ represents (i) a direct bond, (ii) an alkylene or alkenylene linkage each optionally substituted by (a) alkyl, alkenyl, alkynyl, cycloalkyl, cycloalkenyl, aryl, arylalkyl, heteroaryl, heteroarylalkyl or heterocycloalkyl, or by (b) alkyl substituted by alkoxy, hydroxy, arylalkyoxy, heteroarylalkyloxy, alkylthio, carboxy, alkoxycarbonyl, or —C(=O)—$NH_2$, (iii) a —[C(=O)—N($R^6$)—C($R^4$)($R^7$)]$_p$— linkage in which $R^4$ is hydrogen or lower alkyl, $R^6$ is hydrogen, alkyl, alkenyl, alkynyl, cycloalkyl, cycloalkylalkyl, cycloalkenyl, cycloalkenylalkyl, aryl, arylalkyl, heteroaryl, heteroarylalkyl, heterocycloalkyl, heterocycloalkylalkyl or alkyl substituted by alkoxy, hydroxy or alkylthio, $R^7$ is hydrogen, alkyl, alkenyl, alkynyl, cycloalkyl, cycloalkylalkyl, cycloalkenyl, cycloalkenylalkyl, aryl, arylalkyl, heteroaryl, heteroarylalkyl, heterocycloalkyl, heterocycloalkylalkyl or alkyl substituted by alkenyl, alkynyl, alkoxy, hydroxy, arylalkyoxy, heteroarylalkyloxy, alkylthio, carboxy, alkoxycarbonyl or carboxamide, and p is one, (iv) a —$Z^2$—$R^9$— linkage in which $Z^2$ is O, S, $NR^4$, $SO_2NR^4$ or C(=O)$NR^4$ and $R^9$ is $C_{1-4}$alkylene, optionally substituted by alkyl, alkenyl, alkynyl, cycloalkyl, cycloalkylalkyl, cycloalkenyl, cycloalkenylalkyl, aryl, arylalkyl, heteroaryl, heteroarylalkyl, heterocycloalkyl or heterocycloalkylalkyl, or (v) a —$CH_2$—$Z^2$—$R^9$— linkage in which $Z^2$ is O, $NR^4$ or C(=O)$NR^4$ and $R^9$ is $C_{1-4}$alkylene, optionally substituted by alkyl, alkenyl, alkynyl, cycloalkyl, cycloalkylalkyl, cycloalkenyl, cycloalkenylalkyl, aryl, arylalkyl, heteroaryl, heteroarylalkyl, heterocycloalkyl or heterocycloalkylalkyl;
 wherein said acid bioisostere is selected from the group consisting of —C(=O)—NHOH, —C(=O)—$CH_2OH$, —C(=O)—$CH_2SH$, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl and heterocyclic phenols.

2. A compound according to claim 1 in which $R^1$ represents hydrogen, halogen, lower alkyl or lower alkoxy.

3. A compound according to claim 2 in which $R^1$ represents hydrogen.

4. A compound according to claim 1 in which $X^1$ represents C—$R^{10}$ where $R^{10}$ is lower alkyl, lower alkoxy, lower alkylthio, lower alkylsulphinyl or lower alkylsulphonyl.

5. A compound according to claim 4 in which $X^1$ represents $CR^{10}$ where $R^{10}$ is lower alkyl or lower alkoxy.

6. A compound according to claim 4 in which $X^1$ represents $CR^{10}$ where $R^{10}$ is methyl.

7. A compound according to claim 1 in which $X^2$ represents $CR^{10}$ where $R^{10}$ is hydrogen, lower alkyl, lower alkoxy, lower alkylthio, lower alkylsulphinyl or lower alkylsulphonyl.

8. A compound according to claim 7 in which $R^{10}$ is lower alkoxy.

9. A compound according to claim 1 in which $X^3$ and $X^6$ represent CH.

10. A compound according to claim 1 in which one of $X^4$ and $X^5$ represents $CR^{11}$ and the other represents CH.

11. A compound according to claim 10 in which within $R^{11}$ the moiety $L^1$ represents a —$R^2$—$R^3$— linkage wherein $R^2$ represents a straight or branched $C_{1-6}$alkylene chain and $R^3$ represents —C(=O)—$NR^4$— where $R^4$ is hydrogen or $C_{1-4}$alkyl.

12. A compound according to claim 10 in which within $R^{11}$ the moiety $L^1$ represents —$CH_2$—C(=O)—$NR^4$— where $R^4$ is hydrogen or methyl.

13. A compound according to claim 10 in which within $R^{11}$ the moiety $Ar^1$ represents optionally substituted p-phenylene or optionally substituted p-pyridindiyl.

14. A compound according to claim 13 in which $Ar^1$ represents unsubstituted p-phenylene.

15. A compound according to claim 13 in which $Ar^1$ represents unsubstituted p-pyridindiyl.

16. A compound according to claim 10 in which within $R^{11}$ the moiety $L^2$ represents (a) a direct bond (b) an optionally substituted straight or branched alkylene linkage (c) an unsubstituted straight or branched alkenylene linkage or (d) a —$Z^2$—$R^9$— linkage.

17. A compound according to claim 16 in which $L^2$ represents a substituted straight or branched $C_{1-4}$alkylene linkage.

18. A compound according to claim 17 in which $L^2$ represents a substituted ethylene linkage.

19. A compound according to claim 17 in which the alkylene substituent is selected from lower alkyl, aryl, heteroaryl, —N($R^{12}$)—C(=O)—$R^{13}$, —N($R^{12}$)—C(=O)—$OR^{13}$, —N($R^{12}$)—$SO_2$—$R^{13}$, —$NY^1Y^2$ and —[C(=O)—N($R^6$)—C($R^4$)($R^7$)]$_p$—C(=O)—$NY^1Y^2$.

20. A compound according to claim 16 in which $L^2$ represents a group $$-\underset{\underset{R^{15}}{|}}{\overset{\overset{R^4}{|}}{C}}-CH_2-,$$

where $R^4$ is hydrogen or lower alkyl and $R^{15}$ represents lower alkyl, or where $R^4$ is hydrogen and $R^{15}$ represents aryl, heteroaryl, —N($R^{12}$)—C(=O)—$R^{13}$, —N($R^{12}$)—C(=O)—$OR^{13}$, —N($R^{12}$)—$SO_2$—$R^{13}$, —$NY^1Y^2$ or —[C(=O)—N($R^6$)—C($R^4$)($R^7$)]$_p$—C(=O)—$NY^1Y^2$.

21. A compound according to claim 16 in which $L^2$ represents a group $$-\underset{\underset{R^{15}}{|}}{CH}-CH_2-$$

where $R^{15}$ represents —N($R^{12}$)—C(=O)—$R^{13}$, —N($R^{12}$)—C(=O)—$OR^{13}$, —N($R^{12}$)—$SO_2$—$R^{13}$ or —$NY^1Y^2$.

22. A compound according to claim 16 in which $L^2$ represents a group $$-\underset{\underset{R^{15}}{|}}{C}-CH_2-$$

where $R^{15}$ represents —N($R^{12}$)—C(=O)—$R^{13}$, —N($R^{12}$)—C(=O)—$OR^{13}$, —N($R^{12}$)—$SO_2$—$R^{13}$ or —$NY^1Y^2$.

23. A compound according to claim 10 in which within $R^{11}$ the moiety Y represents carboxy or an acid bioisostere.

24. A compound according to claim 23 in which Y represents carboxy.

25. A compound according to claim 1 having the formula (Ia):

(Ia)

in which $R^1$, $R^2$, $L^2$, $X^1$, $X^2$, $X^3$ and Y are as defined in claim 1, $Ar^1$ is arylene and —$R^2$—C(=O)—NH—$Ar^1$—$L^2$—Y is attached at the ring 3 or 4 position, and their ester prodrugs and pharmaceutically acceptable salts, and solvates of compounds of formula (Ia) and their ester prodrugs.

26. A compound according to claim 1 having the formula (Ib):

(Ib)

in which $R^1$, $R^2$, $L^2$, $X^1$, $X^2$, $X^3$ and Y are as defined in claim 1, $Ar^1$ is heteroaryldiyl and —$R^2$—C(=O)—NH—$Ar^1$—$L^2$—Y is attached at the ring 3 or 4 position, and their ester prodrugs and pharmaceutically acceptable salts, and solvates of compounds of formula (Ib) and their ester prodrugs.

27. A compound according to claim 25 in which $R^1$ represents hydrogen.

28. A compound according to claim 25 in which $R^2$ represents a straight or branched $C_{1-6}$alkylene chain.

29. A compound according to claim 28 in which $R^2$ represents methylene.

30. A compound according to claim 25 in which $Ar^1$ represents optionally substituted p-phenylene.

31. A compound according to claim 30 in which $Ar^1$ represents unsubstituted p-phenylene.

32. A compound according to claim 27 in which $Ar^1$ represents optionally substituted p-pyridindiyl.

33. A compound according to claim 32 in which $Ar^1$ represents unsubstituted p-pyridindiyl.

34. A compound according to claim 25 in which $L^2$ represents a substituted straight or branched $C_{1-4}$alkylene linkage.

35. A compound according to claim 34 in which $L^2$ represents a substituted ethylene linkage.

36. A compound according to claim 34 in which the alkylene substituent is selected from lower alkyl, aryl, heteroaryl, $-N(R^{12})-C(=O)-R^{13}$, $-N(R^{12})-C(=O)-OR^{13}$, $-N(R^{12})-SO_2-R^{13}$, $-NY^1Y^2$ or $-[C(=O)-N(R^6)-C(R^4)(R^7)]_p-C(=O)-NY^1Y^2$.

37. A compound according to claim 25 in which $L^2$ represents a

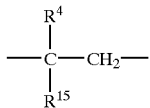

linkage, where $R^4$ is hydrogen or lower alkyl and $R^{15}$ represents lower alkyl, or where $R^4$ is hydrogen and $R^{15}$ represents aryl, heteroaryl, $-N(R^{12})-C(=O)-R^{13}$, $-N(R^{12})-C(=O)-OR^{13}$, $-N(R^{12})-SO_2-R^{13}$, $-NY^1Y^2$ or $-[C(=O)-N(R^6)-C(R^4)(R^7)]_p-C(=O)-NY^1Y^2$.

38. A compound according to claim 37 in which $L^2$ represents a

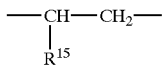

linkage, where $R^{15}$ represents $-N(R^{12})-C(=O)-R^{13}$, $-N(R^{12})-C(=O)-OR^{13}$, $-N(R^{12})-SO_2-R^{13}$ or $-NY^1Y^2$.

39. A compound according to claim 37 in which $L^2$ represents a

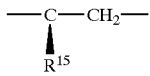

linkage, where $R^{15}$ represents $-N(R^{12})-C(=O)-R^{13}$, $-N(R^{12})-C(=O)-OR^{13}$, $-N(R^{12})-SO_2-R^{13}$ or $-NY^1Y^2$.

40. A compound according to claim 24 in which $X^1$ represents $CR^{10}$ where $R^{10}$ is lower alkyl or lower alkoxy.

41. A compound according to claim 40 in which $R^{10}$ is methyl.

42. A compound according to claim 25 in which $X^2$ represents $CR^{10}$ where $R^{10}$ is lower alkyl, lower alkoxy, lower alkylthio, lower alkylsulphinyl or lower alkylsulphonyl.

43. A compound according to claim 42 in which $R^{10}$ is lower alkoxy.

44. A compound according to claim 25 in $X^3$ represents CH.

45. A compound according to claim 25 in which Y represents carboxy.

46. A compound according to claim 25 in which the group $-R^2-C(=O)-NH-Ar^1-L^2-Y$ is attached at the ring 4 position.

47. A compound according to claim 25 in which $X^1$ represents $CR^{10}$ where $R^{10}$ is lower alkyl or lower alkoxy.

48. A compound according to claim 47 in which $R^{10}$ is methyl.

49. A compound according to claim 25 in which $X^1$ is C-methyl, $X^2$ is C-methoxy and $X^3$ is CH.

50. A compound according to claim 26 in which $R^1$ represents hydrogen.

51. A compound according to claim 26 in which $R^2$ represents a straight or branched $C_{1-6}$alkylene chain.

52. A compound according to claim 51 in which $R^2$ represents methylene.

53. A compound according to claim 26 in which $Ar^1$ represents optionally substituted p-pyridindiyl.

54. A compound according to claim 53 in which $Ar^1$ represents unsubstituted p-pyridindiyl.

55. A compound according to claim 26 in which $L^2$ represents a substituted straight or branched $C_{1-4}$alkylene linkage.

56. A compound according to claim 55 in which $L^2$ represents a substituted ethylene linkage.

57. A compound according to claim 55 in which the alkylene substituent is selected from lower alkyl, aryl, heteroaryl, $-N(R^{12})-C(=O)-R^{13}$, $-N(R^{12})-C(=O)-OR^{13}$, $-N(R^{12})-SO_2-R^{13}$, $-NY^1Y^2$ or $-[C(=O)-N(R^6)-C(R^4)(R^7)]_p-C(=O)-NY^1Y^2$.

58. A compound according to claim 26 in which $L^2$ represents is a

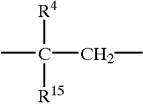

linkage, where $R^4$ is hydrogen or lower alkyl and $R^{15}$ represents lower alkyl, or where $R^4$ is hydrogen and $R^{15}$ represents aryl, heteroaryl, $-N(R^{12})-C(=O)-R^{13}$, $-N(R^{12})-C(=O)-OR^{13}$, $-N(R^{12})-SO_2-R^{13}$, $-NY^1Y^2$ or $-[C(=O)-N(R^6)-C(R^4)(R^7)]_p-C(=O)-NY^1Y^2$.

59. A compound according to claim 58 in which $L^2$ represents a

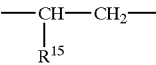

linkage, where $R^{15}$ represents $-N(R^{12})-C(=O)-R^{13}$, $-N(R^{12})-C(=O)-OR^{13}$, $-N(R^{12})-SO_2-R^{13}$ or $-NY^1Y^2$.

60. A compound according to claim 58 in which $L^2$ represents a

linkage, where $R^{15}$ represents $-N(R^{12})-C(=O)-R^{13}$, $-N(R^{12})-C(=O)-OR^{13}$, $-N(R^{12})-SO_2-R^{13}$ or $-NY^1Y^2$.

61. A compound according to claim 26 in which $X^1$ represents $CR^{10}$ where $R^{10}$ is lower alkyl or lower alkoxy.

62. A compound according to claim 61 in which $R^{10}$ is methyl.

63. A compound according to claim 26 in which $X^2$ represents $CR^{10}$ where $R^{10}$ is lower alkyl, lower alkoxy, lower alkylthio, lower alkylsulphinyl or lower alkylsulphonyl.

64. A compound according to claim 63 in which $R^{10}$ is lower alkoxy.

65. A compound according to claim 26 in $X^3$ represents CH.

66. A compound according to claim 26 in which Y represents carboxy.

67. A compound according to claim 26 in which the group —$R^2$—C(=O)—NH—$Ar^1$—$L^2$—Y is attached at the ring 4 position.

68. A compound according to claim 26 in which $X^1$ is C-methyl, $X^2$ is C-methoxy and $X^3$ is CH.

69. A compound selected from the following:

(R)-3-acetylamino-3-(4-{3-methoxy-4-[3-(2-methylphenyl) ureido]phenyl-acetylamino}phenyl)-propanoic acid;

(R)-3-(4-carboxybutanoylamino)-3-(4-{3-methoxy-4-[3-(2-methylphenyl)ureido]phenyl-acetylamino}phenyl)-propanoic acid;

(R)-3-(3-carboxypropanoylamino)-3-(4-{3-methoxy-4-[3-(2-methylphenyl)ureido]phenyl-acetylamino}phenyl)-propanoic acid;

(R)-3-(pyridine-3-carbonylamino)-3-(4-{3-methoxy-4-[3-(2-methylphenyl)ureido]phenyl-acetylamino}phenyl)-propanoic acid;

(R)-3-benzoylamino-3-(4-{3-methoxy-4-[3-(2-methylphenyl)ureido]phenylacetylamino}phenyl)-propanoic acid;

(R)-3-[2-(2-methoxyethoxy)acetylamino]-3-(4-{3-methoxy-4-[3-(2-methylphenyl)ureido]phenyl-acetylamino}phenyl)-propanoic acid;

(R)-3-[(tetrahydropyran-4-carbonyl)amino]-3-(4-{3-methoxy-4-[3-(2-methylphenyl)ureido]-phenylacetylamino}phenyl)-propanoic acid;

(R)-3-[(5-methyl-isoxazole-3-carbonyl)-amino]-3-(4-{3-methoxy-4-[3-(2-methylphenyl)ureido]-phenylacetylamino}phenyl)-propanoic acid;

(R)-3-[(thiophene-2-carbonyl)-amino]-3-(4-{3-methoxy-4-[3-(2-methylphenyl)ureido]phenyl-acetylamino}phenyl)-propanoic acid;

(R)-3-[(4-carboxybenzoyl)-amino]-3-(4-{3-methoxy-4-[3-(2-methylphenyl)ureido]phenyl-acetylamino}phenyl)-propanoic acid;

(R)-3-[(pyridazin-3-carbonyl)-amino]-3-(4-{3-methoxy-4-[3-(2-methylphenyl)ureido]phenyl-acetylamino}phenyl)-propanoic acid;

(R)-3-[(3,4-dimethoxybenzoyl)-amino]-3-(4-{3-methoxy-4-[3-(2-methylphenyl)ureido]phenyl-acetylamino}phenyl)-propanoic acid;

(R)-3-[(pyridazin-3-carbonyl)-amino]-3-(4-{4-[3-(2-methylphenyl)ureido]phenylacetylamino}-phenyl)-propanoic acid;

(R)-3-(4-carboxy-3,3-dimethyl-butanoylamino)-3-(4-{3-methoxy-4-[3-(2-methylphenyl)ureido]-phenylacetylamino}-phenyl)-propanoic acid;

(R)-3-(benzoylamino)-3-(4-{4-[3-(2-methylphenyl)ureido] phenylacetylamino}phenyl)-propanoic acid;

(R)-3-(4-carboxybutanoylamino)-3-(4-{4-[3-(2-methylphenyl)ureido]phenylacetylamino}-phenyl)-propanoic acid;

and the corresponding N-oxides, and their ester prodrugs; and pharmaceutically acceptable salts and solvates of such compounds and their N-oxides and ester prodrugs.

70. (R)-3-(4-Carboxybutanoylamino)-3-(4-{3-methoxy-4-[3-(2-methylphenyl)ureido]phenyl-acetylamino}phenyl)-propanoic acid, and the corresponding N-oxide, and its ester prodrugs; and pharmaceutically acceptable salts and solvates of this compound and its N-oxide and ester prodrugs.

71. (R)-3-Benzoylamino-3-(4-{3-methoxy-4-[3-(2-methylphenyl)ureido]phenylacetylamino}-phenyl) propanoic acid, and the corresponding N-oxide, and its ester prodrugs; and pharmaceutically acceptable salts and solvates of this compound and its N-oxide and ester prodrugs.

72. A compound according to claim 1 wherein:

$R^1$ is hydrogen, halogen, lower alkyl or lower alkoxy;

$X^1$, $X^2$ and $X^6$ independently represent N or $CR^{10}$; and one of $X^3$, $X^4$ and $X^5$ represents $CR^{11}$ and the others independently represents N or $CR^{10}$;

$R^{10}$ is hydrogen, halogen, lower alkyl or lower alkoxy;

$R^{11}$ represents a group —$L^1$—$Ar^1$—$L^2$—Y;

$L^1$ represents a —$R^2$—$R^3$— linkage;

$R^2$ is a straight or branched $C_{1-6}$alkylene chain, a straight or branched $C_{2-6}$alkenylene chain or a straight or branched $C_{2-6}$alkynylene chain;

$R^3$ is a direct bond, cycloalkylene, heterocycloalkylene, arylene, heteroaryldiyl, —C(=Z)—$NR^4$—, —$NR^4$—C(=Z)—, —$Z^1$—, —C(=O)—, —C(=$NOR^4$)—, —$NR^4$—C(=Z)—$NR^4$—, —$SO_2$—$NR^4$—, —$NR^4$—$SO_2$—, —O—C(=O)—, —C(=O)—O—, —$NR^4$—C(=O)—O— or —O—C(=O)—$NR^4$—;

$R^4$ is a hydrogen atom or a lower alkyl group;

Z is O or S;

$Z^1$ is O, $S(O)_n$ or $NR^4$;

n is zero or an integer 1 or 2;

provided that an oxygen, nitrogen or sulphur atom in $R^3$ is not attached directly to a carbon carbon multiple bond in $R^2$;

$Ar^1$ is arylene or heteroaryldiyl;

$L^2$ represents:

(i) a direct bond;

(ii) an alkylene, alkenylene, alkynylene, cycloalkenylene, cycloalkylene, heteroaryldiyl, heterocycloalkylene or arylene linkage each optionally substituted by (a), $R^5$, —ZH, —$ZR^5$, —C(=O)—$R^5$, —NH—C(=O)—$R^5$, —$NY^1Y^2$, or —[C(=O)—N($R^6$)—C($R^4$)($R^7$)]$_p$—C(=O)—$NY^1Y^2$, or by (b) alkyl substituted by carboxy, imidazolyl, —ZH, —$ZR^5$ or —$NY^1Y^2$;

(iii) a —[C(=O)—N($R^6$)—C($R^4$)($R^7$)]$_p$— linkage;

(iv) a —$Z^2$—$R^9$— linkage;

(v) a —C(=O)—$CH_2$—C(=O)— linkage;

(vi) a —$R^9$—$Z^2$—$R^9$— linkage; or (vii) a —C($R^4$)($R^8$)—[C(=O)—N($R^6$)—C($R^4$)($R^7$)]$_p$— linkage;

$R^5$ is alkyl, alkenyl,, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl, or heterocycloalkylalkyl;

$R^6$ is hydrogen, $R^5$ or alkyl substituted with alkoxy, cycloalkyl, hydroxy, mercapto, alkylthio or —$NY^1Y^2$;

$R^7$ and $R^8$ are each independently selected from hydrogen or a group consisting amino acid side chains and corresponding protected derivatives, carboxy, $R^5$, —ZH, —$ZR^5$, —C(=O)—$R^5$, or —C(=O)—$NY^1Y^2$, or alkyl substituted by carboxy, imidazolyl, —ZH, —$ZR^5$, —$NY^1Y^2$, —NH—C(=O)—$R^5$, —C(=O)—$R^2$—$NH_2$, —C(=O)—$Ar^1$—$NH_2$, —C(=O)—$R^2$—$CO_2H$, or —C(=O)—$NY^1Y^2$;

or $R^6$ and $R^7$ or $R^6$ and $R^8$ together with the atoms to which they attached form a 3- to 6-membered heterocycloalkyl ring;

$R^9$ is $C_{1-6}$alkylene, optionally substituted by $R^5$;

$Y^1$ and $Y^2$ are independently hydrogen, alkyl (optionally substituted with hydroxy, heterocycloalkyl, or one or more carboxy or —C(=O)—$NHR^4$ groups), aryl, heteroaryl or heterocycloalkyl; or the group —NY$^1$Y$^2$ may form a 5- to 7-membered cyclic amine which (i) may be optionally substituted with one or more substituents selected from carboxamido, carboxy, hydroxy, oxo, or alkyl optionally substituted by carboxy or carboxamido; (ii) may also contain a further heteroatom selected from O, S, SO$_2$, or NH; and (iii) may also be fused to additional aryl, heteroaryl, heterocycloalkyl or cycloalkyl rings to form a bicyclic or tricyclic ring system;

Z$^2$ is O, S(O)$_n$, NR$^4$, SONR$^4$, C(=O)NR$^4$ or C(=O); and p is zero or an integer 1 to 4; and Y is carboxy, an acid bioisostere, or —C(=O)—NY$^1$Y$^2$;

and their ester prodrugs; and pharmaceutically acceptable salts and solvates of such compounds and their ester prodrugs.

73. A resin selected from the group consisting of:

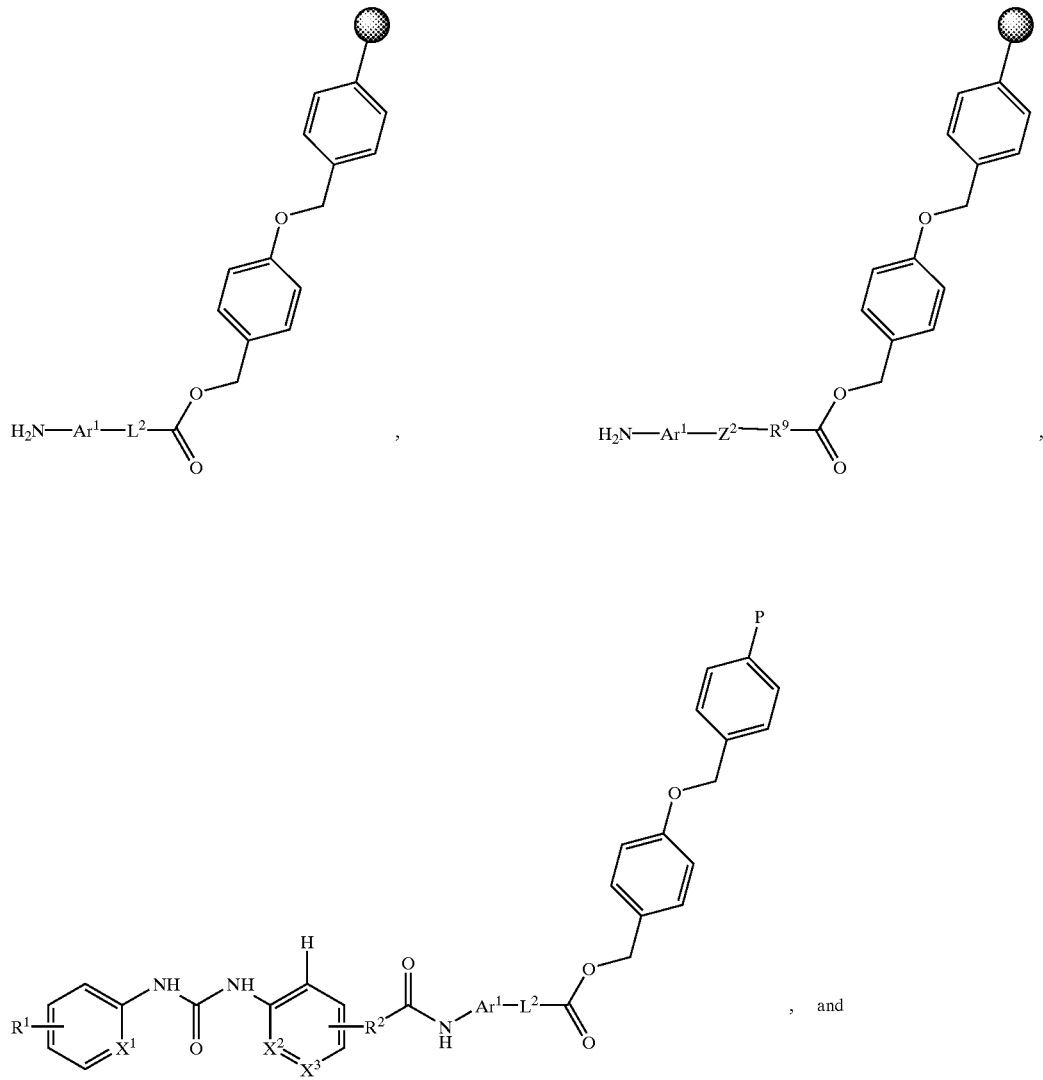

-continued

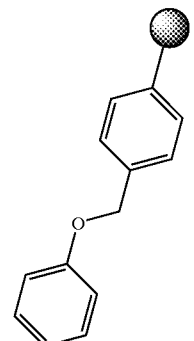
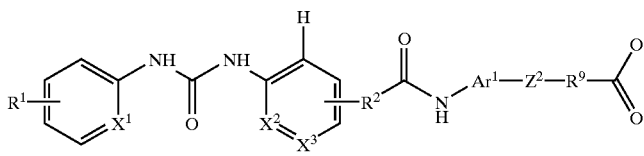

74. A pharmaceutical composition comprising an effective amount of a compound according to claim 1 or a corresponding N-oxide, or an ester prodrug thereof; or a pharmaceutically acceptable salt or solvate of such a compound or its N-oxide or an ester prodrug thereof, in association with a pharmaceutically acceptable carrier or excipient.

75. A composition according to claim 74 for use in the treatment of asthma.

76. A method of treating a patient suffering from, or subject to, asthma comprising administering to said patient a pharmaceutically effective amount of a compound according to claim 1, or a corresponding N-oxide, or an ester prodrug thereof; or a pharmaceutically acceptable salt or solvate of such a compound or its N-oxide or an ester prodrug thereof.

77. A method of treating a patient suffering from, or subject to, joint inflammation comprising administering to said patient a pharmaceutically effective amount of a compound according to claim 1, or a corresponding N-oxide, or an ester prodrug thereof; or a pharmaceutically acceptable salt or solvate of such a compound or its N-oxide or an ester prodrug thereof.

78. A method of treating a patient suffering from, or subject to, asthma comprising administering to said patient a pharmaceutically effective amount of a composition according to claim 74.

79. A method of treating a patient suffering from, or subject to, joint inflammation comprising administering to said patient a pharmaceutically effective amount of a composition according to claim 74.

80. A method of treating a patient suffering from, or subject to, inflammatory bowel disease comprising administering to said patient a pharmaceutically effective amount of a compound according to claim 1, or a corresponding N-oxide, or an ester prodrug thereof; or a pharmaceutically acceptable salt or solvate of such a compound or its N-oxide or an ester prodrug thereof.

81. A method of treating a patient suffering from, or subject to, inflammatory bowel disease comprising administering to said patient a pharmaceutically effective amount of a composition according to claim 74.

* * * * *